US009233931B2

(12) United States Patent
Tazi et al.

(10) Patent No.: US 9,233,931 B2
(45) Date of Patent: Jan. 12, 2016

(54) CHEMICAL MOLECULES THAT INHIBIT THE SLICING MECHANISM FOR TREATING DISEASES RESULTING FROM SPLICING ANOMALIES

(71) Applicants: CENTRE NATIONAL DE RECHERCHE SCIENTIFIQUE, Paris (FR); INSTITUT CURIE, Paris (FR); UNIVERSITE MONTPELLIER 2 SCIENCES ET TECHNIQUES, Montpellier (FR)

(72) Inventors: Jamal Tazi, Clapiers (FR); David Grierson, Vancouver, CA (US); Florence Mahuteau-Betzer, Saint-Remy-Les-Chevreuse (FR); Pierre Roux, Saint Gely du Fesc (FR)

(73) Assignees: CENTRE NATIONALE DE RECHERCHE SCIENTIFIQUE, Paris (FR); INSTITUT CURIE, Paris (FR); UNIVERSITE MONTPELLIER 2 SCIENCES ET TECHNIQUES, Montpellier (FR)

( * ) Notice: Subject to any disclaimer, the term of this patent is extended or adjusted under 35 U.S.C. 154(b) by 8 days.

(21) Appl. No.: 14/070,799

(22) Filed: Nov. 4, 2013

(65) Prior Publication Data

US 2014/0155436 A1 Jun. 5, 2014

Related U.S. Application Data

(62) Division of application No. 12/811,931, filed as application No. PCT/EP2009/050280 on Jan. 12, 2009, now Pat. No. 8,604,063.

(30) Foreign Application Priority Data

Jan. 10, 2008 (FR) ..................................... 08 50144

(51) Int. Cl.

| C07D 233/64 | (2006.01) |
| C07D 213/38 | (2006.01) |
| C07D 213/56 | (2006.01) |
| C07D 213/74 | (2006.01) |
| C07D 213/75 | (2006.01) |
| C07D 213/82 | (2006.01) |
| C07D 233/61 | (2006.01) |
| C07D 249/06 | (2006.01) |
| C07D 401/12 | (2006.01) |
| C07D 401/14 | (2006.01) |
| C07C 237/30 | (2006.01) |

(52) U.S. Cl.

CPC ............ *C07D 233/64* (2013.01); *C07C 237/30* (2013.01); *C07D 213/38* (2013.01); *C07D 213/56* (2013.01); *C07D 213/74* (2013.01); *C07D 213/75* (2013.01); *C07D 213/82* (2013.01); *C07D 233/61* (2013.01); *C07D 249/06* (2013.01); *C07D 401/12* (2013.01); *C07D 401/14* (2013.01)

(58) Field of Classification Search

CPC ...................................................... C07D 233/64
See application file for complete search history.

(56) References Cited

U.S. PATENT DOCUMENTS

| 2,671,805 | A | 3/1954 | Krimmel |
| 3,409,668 | A | 11/1968 | Palazzo et al. |
| 4,001,416 | A | 1/1977 | Pommer et al. |
| 4,434,290 | A | 2/1984 | Bisagni et al. |
| 4,855,308 | A | 8/1989 | Kester et al. |
| 5,079,363 | A | 1/1992 | Bouisset et al. |
| 5,579,033 | A | 11/1996 | Rutledge et al. |
| 6,419,710 | B1 | 7/2002 | Demeulenaere et al. |
| 2004/0054114 | A1 | 3/2004 | Mayorga et al. |
| 2004/0171833 | A1 | 9/2004 | Buchwald et al. |
| 2005/0154232 | A1* | 7/2005 | Lardy et al. .................. 564/112 |
| 2007/0054905 | A1 | 3/2007 | Tazi et al. |
| 2007/0072915 | A1 | 3/2007 | Lardy et al. |
| 2011/0053975 | A1 | 3/2011 | Tazi et al. |

FOREIGN PATENT DOCUMENTS

| CN | 1281694 A | 1/2001 |
| CN | 1331669 A | 1/2002 |
| CN | 1590390 A | 3/2005 |
| CN | 1639126 A | 7/2005 |
| CN | 1938261 A | 3/2007 |
| DE | 374 291 C | 4/1923 |
| FR | 2 089 546 A5 | 1/1972 |
| FR | 2 859 474 A1 | 3/2005 |
| FR | 2 859 475 A1 | 3/2005 |
| GB | 995 039 A | 6/1965 |
| GB | 2 327 675 A | 2/1999 |
| JP | A-50-95285 | 7/1975 |
| JP | A-62-158252 | 7/1987 |

(Continued)

OTHER PUBLICATIONS

V. Peesapati et al., "Convenient Synthesis of Some Styrylpyridinium Dyes Containing Aminobis[benzenamine] Moiety," Indian Journal of Chemistry, vol. 35B, Mar. 1996, pp. 207-212.

(Continued)

*Primary Examiner* — Paul Zarek

(74) *Attorney, Agent, or Firm* — Oliff PLC

(57) ABSTRACT

The present invention relates to a compound of one of the formulas I to XXI; a pharmaceutical composition comprising at least one such compound; and the use of at least one such compound in preparing a drug to treat, in a subject, a genetic disease resulting from at least one splicing anomaly.

2 Claims, 2 Drawing Sheets

(56) References Cited

FOREIGN PATENT DOCUMENTS

| JP | A-11-147874 | 6/1999 |
|---|---|---|
| NL | 6511104 | 3/1966 |
| WO | WO 00/37412 A1 | 6/2000 |
| WO | WO 03/076406 A1 | 9/2003 |
| WO | WO 2005/023255 A2 | 3/2005 |
| WO | WO 2005/092832 A1 | 10/2005 |
| WO | WO 2006/133848 A1 | 12/2006 |
| WO | WO 2007/096647 A2 | 8/2007 |
| WO | WO 2009/087238 A2 | 7/2009 |

OTHER PUBLICATIONS

Von Adolf Emil Siegrist, "Preparation of Styryl and Stilbenyl Derivatives of 1 H-Benzotriazoles," Helvetica Chimica Acta, vol. 64, 1981, No. 68, pp. 662-680 (with English-language Summary).
Jye-Shane Yang et al., "Origin of the N-methyl and N-phenyl Substituent Effects on the Fluorescence Vibronic Structures of *trans*-4-aminostilbene and its Derivatives in Hexane," Photochem. Photobiol. Sci., 2003, vol. 2, pp. 1225-1231.
Nayak et al; "p53-Induced Apoptosis and Inhibitors of p53;" Current Medicinal Chemistry; 2009; vol. 16; No. 21 pp. 2627-2640.
Hardcastle; "Inhibitors of the MDM2-p53 interaction as anticancer drugs;" Drugs of the Future; 2007; vol. 32; No. 10; pp. 883-896.
Aug. 3, 2011 Search Report issued in European Patent Application No. EP 11 30 5385.
Sep. 28, 2012 Search Report issued in International Patent Application No. PCT/IB2012/051603.
Sep. 28, 2012 Written Opinion issued in International Patent Application No. PCT/IB2012/051603.
Lourenco et al; "Evaluation of anti-tubercular activity of nicotinic and isoniazid analogues;" ARKIVOC; 2007; pp. 181-191.
Park et al; "Photoreaction of 2-Halo-N-pyridinylbenzamide: Intramolecular Cyclization Mechanism of Phenyl Radical Assisted with n-Complexation of Chlorine Radical;" J. Org. Chem. 2001; vol. 66; pp. 2197-2206.
Sep. 5, 2013 Office Action issued in Japanese Patent Application No. 2010-541800 (with translation).
Sorenson; "Selective N-Arylation of Aminobenzanilides under Mild Conditions Using Triarylbismuthanes;" J. Org. Chem.; 2000; vol. 65; pp. 7747-7749.
Coyne et al; "3,4-Dihydro-2(1H)-quinazolinones;" Journal of Medicincal Chemistry; 1968; vol. 11; No. 6; pp. 1208-1218.
Huang et al; "Expanding Pd-Catalyzed C-N Bond-Forming Processes: The First Amidation of Aryl Sulfonates, Aqueous Amination, and Complementarity with Cu-Catalyzed Reactions;" J. Am. Chem. Soc.; 2003; vol. 125; No. 22; pp. 6653-6655.
Shankaran et al; "Silicon in Benzamide Directed Ortho Metalation, Formation and Reactions of Benzamide Benynes;" Tetrahedron Letters; 1984; vol. 25; No. 27; pp. 2827-2830.
Peet et al; "A Novel Oxamide Rearrangement;" J. Heterocyclic Chem.; 1980; vol. 17; pp. 1513-1518.
Ward et al; "Solid Phase Synthesis of Aryl Amines Palladium Catalyzed Amination of Resin-Bound Aromatic Bromides;" Tetrahedron Letters; 1996; vol. 37; No. 39; pp. 6993-6996.
Elter et al; "Über das 9-Methyl-3-carbolin and das 6-Methly-3-carbolin;" Monatshefte Fuer Chemie; 1950; vol. 81; pp. 404-413.
Gennarro; "Pyrido[3,2-b][1,4]benzothiazine (1-Azaphenothiazine);" J. Org. Chem.; 1959; vol. 24; pp. 1156-1157.
Chemical Abstracts Service; "Aminopyridines;" XP-002499122; 1966.
Tazi et al; "The spliceosome: a novel multi-faceted target for therapy;" TRENDS in Biochemical Sciences; Aug. 2005; vol. 30; No. 8; pp. 494-478.
Jul. 26, 2010 Written Opinion issued in International Patent Application No. PCT/EP2009/050280.
Jul. 26, 2010 Search Report issued in International Patent Application No. PCT/EP2009/050280.

Ito et al; "A medium-term rat liver bioassay for rapid in vivo detection of carcinogenic potential of chemicals;" Cancer Sci; Jan. 2003; vol. 94; No. 1; pp. 3-8.
Yang et al; "Photoinduced Single—versus Double-Bond Torsion in Donor-Accepted-Substituted *trans*-Stilbenes;" J. Phys. Chem. A; 2006; vol. 110; pp. 8003-8010.
Aug. 24, 2012 Office Action issued in U.S. Appl. No. 12/811,931.
Jan. 1, 2013 Office Action issued in U.S. Appl. No. 12/811,931.
Aug. 5, 2013 Notice of Allowance issued in U.S. Appl. No. 12/811,931.
Jul. 10, 2013 Office Action issued in Chinese Patent Application No. 20098010636.1 (English-language translation only).
U.S. Appl. No. 14/009,283, filed Oct. 1, 2013.
Chesnokov, et al., "Synthesis and Biological Activity of Substituted Amides of 2-Aminonicotinic Acid," Perm Pharmaceutical Institute, Translated from Khimiko-Farmatsevticheskii Zhurnal, vol. 7, No. 11, pp. 20-23, Nov. 1973.
Cuffini, et al., "Nine N-aryl-2-choloronicotinamides: supramolecular structures in one, two and three dimensions,"Acta Crystallographica Section B, B62 pp. 651-665, 2006.
Jozwiak, et al., "Behaviour of N-Pyridylbenzamides versus Benzanilides in the *ortho*-Directed Lithiation of Masked Aromatic Carboxylic Acids," Eur. J. Org. Chem., pp. 3254-3261, 2004.
Kumar, et al., "Exploring hydrogen-bond capable backbone and ligating topologies: Co(II) coordination polymers derived from mixed ligand systems," Journal of Molecular Structure, 796, pp. 139-145, 2006.
Lam, et al., "α-Nitrogen activating effect in the room temperature copper-promoted N-arylation of heteroarylcarboxamides with phenyl siloxane or *p*-toluylboronic acid," Tetrahedron Letters 42, pp. 2427-2429, 2001.
Singha, et al., "$^1$H and $^{13}$C NMR spectral studies of conformation of some N-(2-pyridinyl)-3-pyridinecarboxamides," Journal of Molecular Structure, 449, pp. 91-98, 1998.
Sigova, et al., "Synthesis and Biological Activity of Arylamides of 2-Methylnicotinic and 2-Phenylindolizine-8-Carboxylic Acids," Perm Pharmaceutical Institute, Translated from Khimiko-Farmatsevticheskii Zhurnal, vol. 19, No. 3, pp. 159-163, Mar. 1985.
Prashad, et al., "A new reaction of N-aryl-2-pyrimidinamines with triphosgene," Tetrahedron Letters, 48, pp. 2087-2089, 2007.
Sep. 10, 2013 Search Report issued in French Patent Application No. FR 1350599 (with English translation).
Sep. 5, 2013 Search Report issued in French Patent Application No. 1350600 (with English Translation).
Okumura et al., "4-Oxo-1,2,3,4-Tetrahydroquinazolines. 11. Synthesis of 1-Alkyl- and 1-[2-(Disubstituted amino)ethyl]-2-methyl-3-aryl-4-oxo-1,2,3,4-tetrahydroquinazolines," Chemical Research Laboratory, vol. 11, pp. 788-792, Jul. 1968.
Okumura et al., "4-Oxo-1,2,3,4-tetrahydroquinazolines. 1. Syntheses and Pharmacological Properties of 2-Methyl-3-aryl-4-oxo-1,2,3,4-tetrahydroquinazolines and Their 1-Acyl Derivatives," Chemical Research Laboratory, vol. 11, pp. 348-352, Mar. 1968.
Correa et al, "Novel Alternative for the N-N Bond Formation through a PIFA-Mediated Oxidative Cyclization and Its Application to the Synthesis of Indazol-3-Ones," J. Org. Chem., vol. 71, pp. 3501-3505, 2006.
Katritsky et al., "Carbon Dioxide: A Reagent for the Simultaneous Protection of Nucleophilic Centres and Activation of Alternative Locations to Electrophilic Attack. Part III. A New Synthetic Method for the Ortho-Substitution of N-Monoalkylanilines," Department of Chemistry, University of Florida, May 1986.
Yamada et al., "4-Oxo-1,2,3,4-Tetrahydroquinazolines. V. Ring Expansion Reaction of 1-Methyl-3-phenyl-4-oxo-3-4-dihydroquinazolinium Bromide with Diazoalkanes," Bulletin of the Chemical Society of Japan, vol. 47, No. 2, pp. 339-340, 1974.
Pakrashi et al., "Studies on 4-Quinazolinones. V. Reductive Ring Cleavage by Metal Hydrides," J. Org. Chem., vol. 37, No. 20, pp. 3143-3147, 1972.
Gatta et al., "Su Alcune Reazioni Con Antranilammidi," II Farmaco—Ed. Sc., vol. 25, No. 11, pp. 830-841, 1970, with English-language Abstract.

\* cited by examiner

CHEMICAL MOLECULES THAT INHIBIT THE SLICING MECHANISM FOR TREATING DISEASES RESULTING FROM SPLICING ANOMALIES

This is a Divisional of application Ser. No. 12/811,931 filed Aug. 30, 2010, which is a 371 of International Application No. PCT/EP2009/050280 filed Jan. 12, 2009. This patent application claims the priority of French patent application FR08/50144 filed on Jan. 10, 2008 which is herein incorporated by reference.

BACKGROUND

Certain indole derivative compounds such as ellipticine derivatives and aza-ellipticine derivatives are already known as intercalating molecules for correcting dysfunctions in gene expression, notably in DNA replication. They have been more specifically described for treating diseases such as cancer, leukemia or AIDS (see in particular patents FR 2,627,493, FR 2,645,861, FR 2,436,786).

Concerning current treatments for AIDS, the various approaches aimed at reducing viral load in patients infected by HIV utilize molecules intended to inhibit the enzymatic activity of viral reverse transcriptase or of the protease involved in virus protein maturation. Regarding reverse transcriptase inhibitors, these can be nucleosidic (NRTIs), non-nucleosidic (NNRTIs) or nucleotidic in nature. The purpose of using these compounds is to prevent a DNA copy of the retroviral genome from being produced and, consequently, from being integrated into the genome of the host cell. Protease inhibitors (PIs) interfere with the proper maturation of viral proteins and cause the production of incomplete particles with altered infectious capacities. There is another type of anti-retroviral compound used for its ability to prevent viruses from entering the cell. These entry inhibitors can be either peptides that interfere with the fusion of viral glycoproteins gp41 or gp120 with the membrane of CD4 cells or molecules that target HIV cellular co-receptors CCR5 and CXCR4. The absence of cellular proteins resembling HIV integrase has also been exploited to develop novel anti-HIV molecules that inhibit this enzymatic activity. Although a number of integrase inhibitors are in the clinical trial phase, no molecule is yet available on the market.

Concerning cancers, more than 90% originate from the malignant transformation of epithelial cells and, in most cases, cancer patient mortality is not due to the primary tumor but to metastases that derive from it. This malignant progression leading to metastases and their subsequent invasion initially involves the loss of cellular adhesion and an increase in motility, thus allowing invasive cells to escape from the initial site and to colonize target tissues. In a great number of cases, it appears that the tumor progression mechanism is associated with aberrant slicing that leads to the formation of isoforms with proto-oncogenic activity. Currently, no molecule with anti-invasive functionality exists. This underlines the lack of a genuinely powerful means of fighting metastases. The current absence of this type of molecule on the market confers on them an economic potential of the highest order.

Duchenne muscular dystrophy (DMD) is a serious illness resulting from mutations in the dystrophin gene. The absence of this protein leads to degeneration of skeletal and cardiac muscles. Several therapeutic strategies are currently envisaged, including so-called exon skipping, whose principle is to cut from dystrophin the internal exon carrying the mutation, thus allowing the production of a shorter but functional dystrophin.

Laminopathies are disorders that lead to an unsatisfactory quality of life, require expensive care and, in many cases, can lead to premature death (i.e., laminopathies of striated muscle tissues and laminopathies characterized by premature aging). Laminopathies are caused by functional changes in lamins, ubiquitous proteins located in the cell nucleus, and in their molecular partners. Most cases of progeria, or early-aging syndrome, are caused by a recurring de novo point mutation (c.1824C>T, "G608G") occurring in exon 11, i.e., in the part of the gene specifically coding for lamin A. It has been shown that this mutation alters splicing mechanisms and leads to the production of a truncated lamin A precursor ("progerin", LaminΔ50, p.V607_Q656del), exerting a dominant negative effect on residual wild proteins.

In all these pathologies, the splicing process plays a key role. This intracellular splicing process consists of eliminating introns in pre-messenger RNAs to produce mature messenger RNAs that can be used by the translation mechanism of the cell (SHARP, Cell, vol. 77, p. 805-815, 1994). In the case of alternative splicing, the same precursor can be the source of messenger RNAs coding for proteins with distinct functions (BLACK, Annu. Rev. Biochem. vol. 72, p. 291-336, 2003). The precise selection of 5' and 3' splicing sites is thus a mechanism that generates diversity and that can lead to the regulation of gene expression according to the type of tissue or during the development of an organism. The factors involved in this selection include a family of proteins called SR, characterized by the presence of one or two RNA recognition motifs (RRM) and a domain rich in arginine and serine residues called an RS domain (MANLEY & TACKE, Genes Dev., vol. 10, p. 1569-1579, 1996). By binding to short exon or intron sequences of the pre-mRNA, called ESE (exonic splicing enhancer) or ISE (intronic splicing enhancer), SR proteins are able to activate, in a dose-dependant manner, sub-optimal splicing sites and to enable the inclusion of exons (GRAVELEY, RNA, vol. 6, p. 1197-1211, 2000). The activity of an SR protein in alternative splicing is specific insofar as the inactivation of the corresponding gene is lethal (WANG et al., Mol. Cell, vol. 7, p. 331-342, 2001).

Sequencing of the human genome and analysis of EST (expressed sequence tag) banks has revealed that 65% of genes are expressed in the form of alternatively spliced variants (EWING & GREEN, Nat. Genet., vol. 25, p. 232-234, 2000; JOHNSON et al., Science, vol. 302, p. 2141-2144, 2003). This mechanism is thus a favored target of modifications that can affect the factors involved in regulating splicing and of mutations that affect the sequences necessary for this regulation. At present, it is estimated that roughly 50% of the point mutations responsible for genetic diseases induce aberrant splicing. These mutations can interfere with splicing by inactivating or creating splicing sites, but also by modifying or generating regulating elements such as splicing enhancers or splicing silencers in a particular gene (CARTEGNI et al., Nat. Rev. Genet., vol. 3, p. 285-298, 2002; TAZI et al., TIBS, vol. 40, p. 469-478, 2005).

The strategies currently developed to correct these splicing defects rest on the use of various types of molecules (TAZI et al., cited above, 2005).

One strategy aimed at developing novel molecules to correct or eliminate abnormal splicing, for example, rests on the overexpression of proteins that interfere with this type of splicing (NISSIM-RAFINIA et al., Hum. Mol. Genet., vol. 9, p. 1771-1778, 2000; HOFINANN et al., Proc. Natl. Acad. Sci. U.S.A., vol. 97, p. 9618-9623, 2000).

Other strategies rest on the use of antisense oligonucleotides (SAZANI et al., Nat. Biotechnol., vol. 20, p. 1228-1233, 2002; SAZANI & KOLE, Prog. Subcell. Biol., vol. 31, p. 217-239, 2003) or of PNA (CARTEGNI et al., *Nat. Struct. Biol.*, vol. 10, p. 120-125, 2003) enabling, respectively, the inhibition or activation of a splicing event.

Yet another strategy rests on the identification of compounds that influence the splicing efficiency of the pre-mRNA of interest (ANDREASSI et al., *Hum. Mol. Genet.*, vol. 10, p. 2841-2849, 2001).

Lastly, a strategy based on the use of trans-splicing to replace mutant exons has been described (LIU et al., *Nat. Biotechnol.*, vol. 20, p. 47-52, 2002).

One of the disadvantages of the developed strategies cited above to correct or eliminate abnormal splicing is their production cost. Indeed, the cost of producing antisense oligonucleotides that must be modified to improve their stability, and that of PNA molecules, is high.

Another disadvantage of the developed strategies cited above is that they require the use of expression vectors, such as, for example, for the strategy based on the use of trans-splicing.

International application WO05023255, under French priority of requests FR0310460 and FR0400973, filed by the Applicant, disclosed the use of indole derivatives to treat diseases related to the pre-messenger RNA splicing process in the cell.

Thus it was recently shown that certain indole derivatives prove particularly effective in treating metastatic cancer and in treating AIDS (BAKKOUR et al., *PLoS Pathogens*, vol. 3, p. 1530-1539, 2007).

However, the compounds described have a flat structure with four rings that have the disadvantage of intercalating between DNA bases and can thus lead to cellular toxicity.

SUMMARY

In order to minimize the risk that these indole derivatives intercalate between DNA bases, the inventors developed novel compounds that are particularly effective in treating diseases related to the splicing process, but which, in a surprising manner, have a cellular toxicity that is clearly less than the indole derivatives of the prior art. In addition, these compounds are able to selectively inhibit certain splicing events.

Thus, the invention relates to novel indole derivative compounds for the preparation of compositions useful for the treatment of diseases resulting from changes in splicing processes.

DETAILED DESCRIPTION OF EMBODIMENTS

Figure 1:
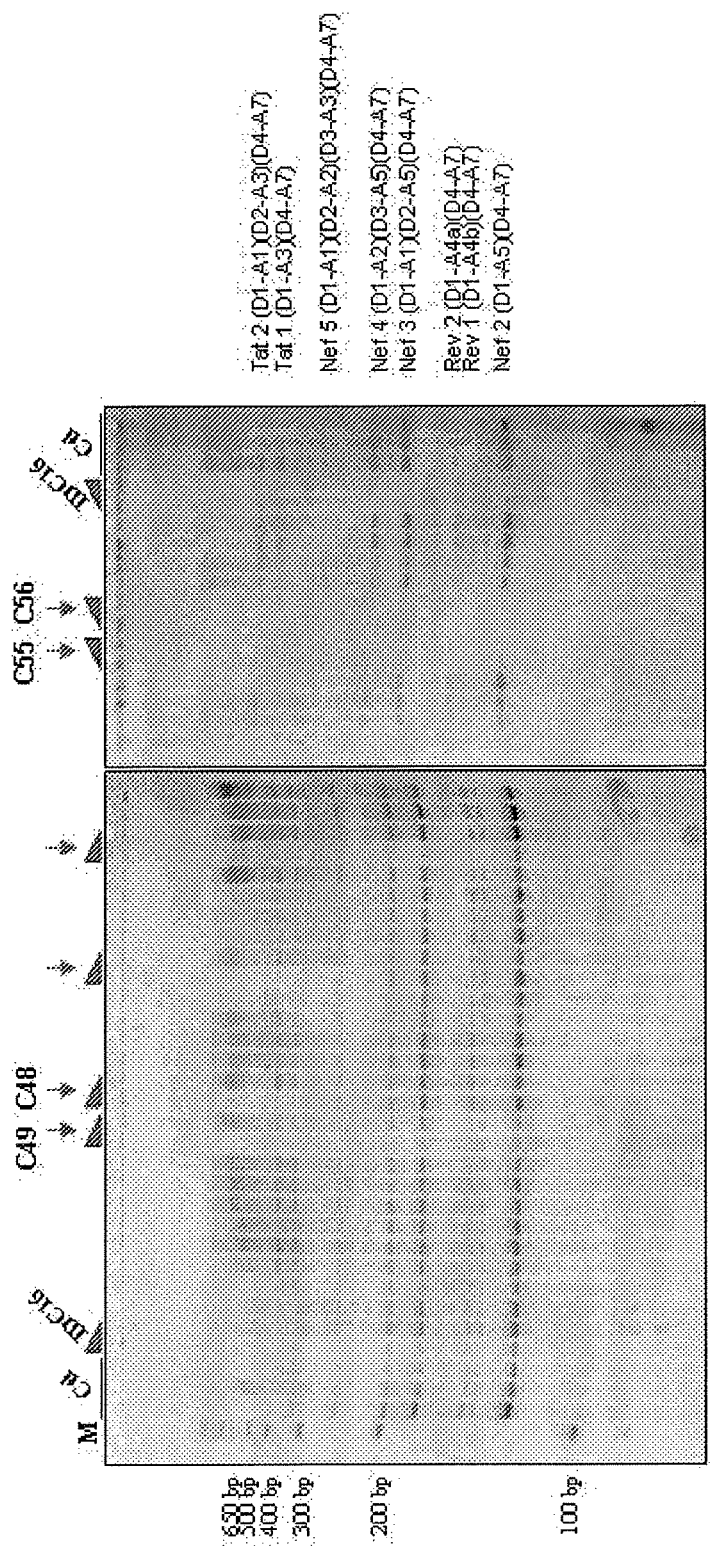
FIG. 1 shows the detail of a polyacrylamide gel obtained presenting the various isoforms obtained (Nef2, Rev1, Rev2, Nef3, Nef4, Nef5, Tat1 and Tat2) for the untreated cells (Clt) or treated with the compounds IDC16, C48, C49, C55 or C56.

A first object of the invention thus relates to a compound of one of the following formulas (I) to (XXI):

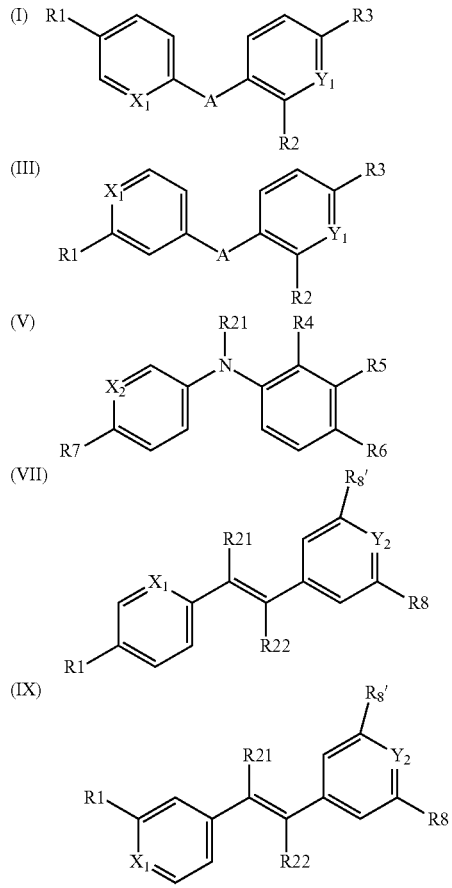
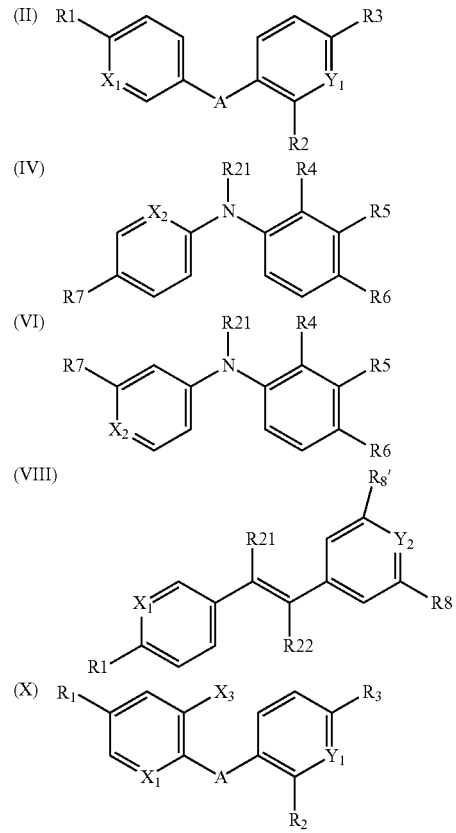

-continued
(XI) When X1 = N—R11
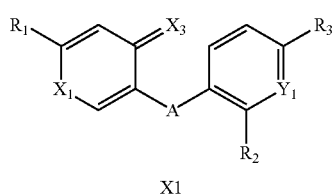
X1
When X1 = Nitrogen
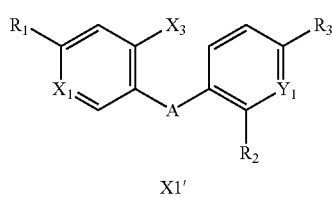
X1'
(XII) 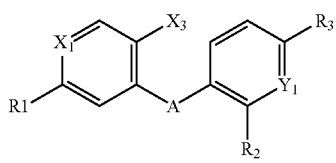
(XIII) 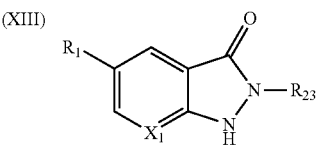
(XIV) 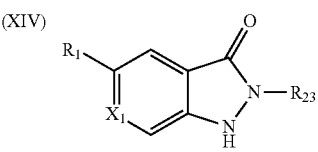
(XV) When X1 = N—R11
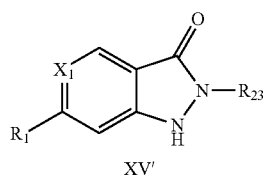
XV
When X1 = Nitrogen
XV'
(XVI) 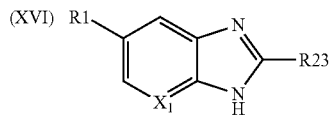
(XVII) 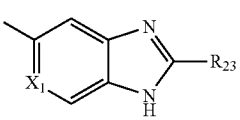
(XVIII) When X1 = N—R11
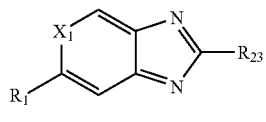
XVIII
When X1 = Nitrogen
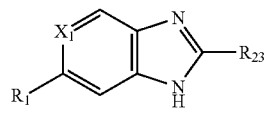
XVIII'
(XIX) 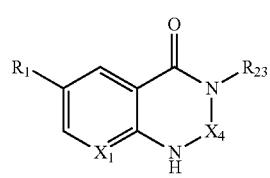
(XX) 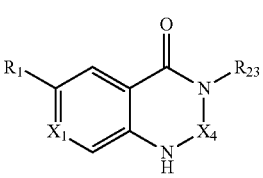
(XXI) When X1 = N—R11
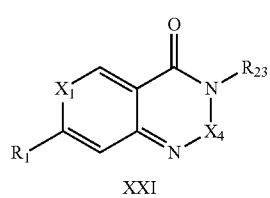
XXI
When X1 = Nitrogen
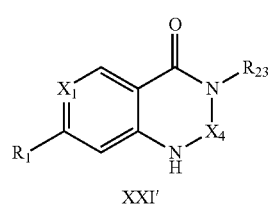
XXI' wherein,

X1 represents a nitrogen atom, a NR11 group or a CR10 group with R10 chosen among the group comprising a hydrogen atom or an NR11R12 or OR11 group with R11 and R12 representing independently of the other a hydrogen atom, a C1 to C3 alkyl group, preferably a methyl or trifluoromethyl group;

with X1 corresponds to NR11 in compounds with formulas XI, XV, XVIII and XXI, and to the chemically distinct isomeric forms XI', XV', XVIII' and XXI' when X1 corresponds to a nitrogen atom;

R1 represents a hydrogen atom, an NR11R12 or OR12 group with R11 and R12 as defined above, with X1 representing a CH group when R1 represents an NR11R12 or OR12 group, preferably R1 represents an OR12 group and more specifically an OCH₃ group;

A represents a

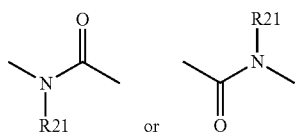

amide group or a

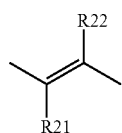

alcene group;

Y1 represents a nitrogen atom or a CR13 group with R13 chosen among the group comprising a hydrogen atom or a

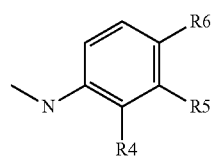

group, preferably a

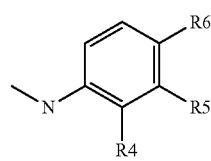

group;

R2 represents a hydrogen, halogen or oxygen atom, in order to form a carbonyl group, or a C1 to C3 alkyl group, preferably a methyl or trifluoromethyl group, an NR14R15 group, an SO2R14R15 group or a C(=O)NR14R15 group with R14 and R15 representing independently of the other:

a hydrogen atom, or a linear or branched C1 to C10 alkyl group, preferably C1 to C6 alkyl group, and most preferably C1 to C3 alkyl group, wherein one or more carbon atoms can be substituted by a nitrogen atom, said alkyl group optionally being substituted by one or more —OH and/or =O groups and/or by a group, substituted or unsubstituted, such as:

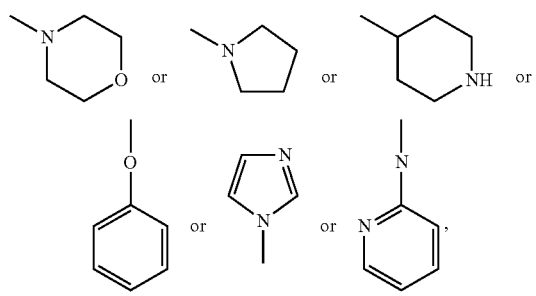

preferably

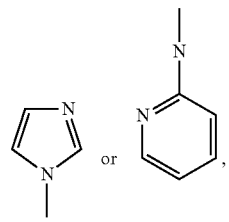

with R2 representing a hydrogen atom when Y1 represents a CR13 group with R13 representing a

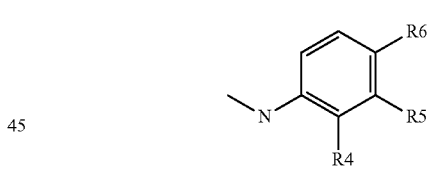

group;

R3 represents a hydrogen atom or an oxygen atom, in order to form a carbonyl group, or a C1 to C3 alkyl group, preferably a methyl or trifluoromethyl group, or an NR14R15 group, an SO2R14R15 or C(=O)NR14R15 group as defined above with R3 representing a hydrogen atom when R2 represents a halogen atom, an NR14R15, SO2R14R15 or C(=O)NR14R15 group and when Y1 represents a CR13 group with R13 representing a

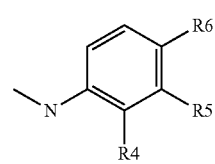

group;
X2 represents a nitrogen atom or a CR16 group with R16 chosen among the group comprising a hydrogen atom or a

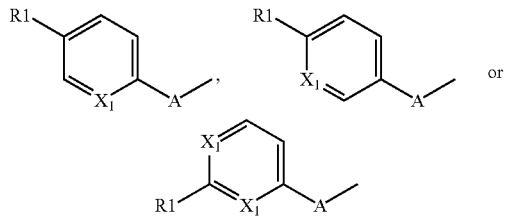

group;
R4 represents a hydrogen atom or a C1 to C3 alkyl group (preferably a methyl group) or a C(=O)NR14R15 group with R4 representing a hydrogen atom or a C1 to C3 alkyl group when R5 or R6 is different than a hydrogen atom;
R5 represents a hydrogen atom, a C(=O)NR14R15 group or a

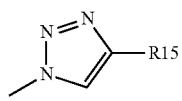

group with R5 representing a hydrogen atom, when R4 or R6 is different than a hydrogen atom;
R6 represents a hydrogen atom, or a C(=O)NR14R15 group or a

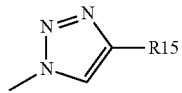

group, preferably R6 represents a C(=O)NR14R15 group, and with R6 representing a hydrogen atom when R5 is different than a hydrogen atom or when R4 is different than a hydrogen atom or a C1 to C3 alkyl group;
R7 represents a hydrogen atom, an NR11R12 or OR12 group with R11 and R12 as defined above, preferably R7 represents a hydrogen atom, and with X2 representing a CH group when R7 represents an NR11R12 or OR12 group;
Y2 represents a nitrogen atom or a CR11 group with R11 chosen among the group comprising a hydrogen atom, a

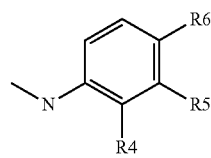

group or a

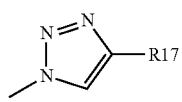

group where R17 represents:
a hydrogen atom, or
a linear or branched C1 to C13 alkyl group, wherein one or more carbon atoms can be substituted by a nitrogen atom, said alkyl group optionally being substituted by one or more —OH and/or =O groups;
with Y2 representing a nitrogen atom or a CR11 group with R11 being a hydrogen atom, when R8 or R8' is different than a nitrogen atom or a CH group and when R8' is different than a hydrogen or halogen atom
R8 and R8' represents a hydrogen or halogen atom, a

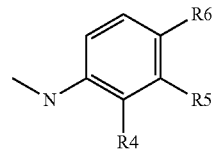

or a C(=O)NR18R19 group with R18 and R19 representing independently of the other:
a hydrogen atom, or
a linear or branched C1 to C13 alkyl group, wherein one or more carbon atoms can be substituted by a nitrogen atom, said alkyl group optionally being substituted by one or more —OH and/or =O groups and/or by a group, substituted or unsubstituted, such as:

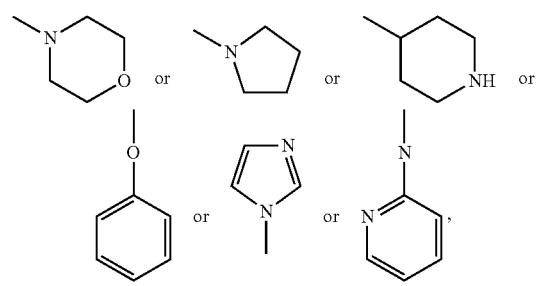

preferably

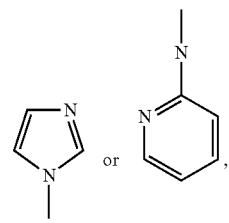

with R8 representing a hydrogen or halogen atom, when Y2 is different than a nitrogen atom or a CH group and when R8' is different than a hydrogen or halogen atom; and
with R8' representing a hydrogen or halogen atom, when Y2 is different than a nitrogen atom or a CH group and when R8 is different than a hydrogen or halogen atom;
X3 represents an oxygen atom, an NOR20 or NNHR20 group with R20 representing a hydrogen atom or a C1 to C6 alkyl group;
X4 represents a CH2 or CO group;
R21 and R22 represent independently of the other a hydrogen atom or a methyl group, preferably a hydrogen atom;

R23 represents a

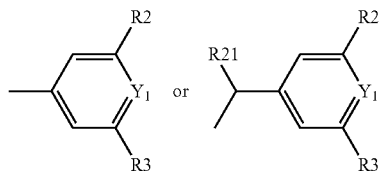

group;
pharmaceutically acceptable salts of said compounds, isomers thereof and/or mixtures of same.

"Halogen atom" means the group comprised of F, Cl, Br and I, preferably said halogen atom is a chlorine atom.

All the compounds disclosed in the examples are in the scope of the present invention.

According to a preferred embodiment, the inventive compound has formula (I).

According to a particular embodiment of said preferred embodiment, the inventive compound has formula (Ia) as follows:

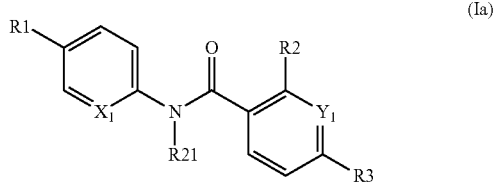

Preferably, said compound is selected among the group comprising:
N-(4-Methoxy-phenyl)-2-[6-(N'-(4-Methoxy-phenylnicotinamido)-pyridin-2-ylamino)-hexylamino]-nicotinamide;
2-(2-Dimethylamino-ethylamino)-N-(4-trifluoromethoxy-phenyl)-nicotinamide;
2-(3-Dimethylamino-propylamino)-N-(4-trifluoromethoxy-phenyl)-nicotinamide;
2-(3-Diethylamino-propylamino)-N-(4-trifluoromethoxy-phenyl)-nicotinamide;
2-(4-Hydroxy-butylamino)-N-(4-trifluoromethoxy-phenyl)-nicotinamide;
N-(4-Trifluoromethoxy-phenyl)-2-[(6-(N'-(4-Trifluoromethoxy-phenylnicotinamido)-pyridin-2-ylamino)-hexylamino]-nicotinamide;
N-(3-Diethylamino-propyl)-3-[3-(3-methoxybenzamido)-phenylamino]-benzamide;
N-(3-Methyl-butyl)-3-methyl-4-[3-(4-methoxybenzamido)-phenylamino]-benzamide; and
(N-Diethylamino)-3-(1-{3-[4(4-methoxybenzamido)-phenylamino]-phenyl}-1H-1,2,3-triazol-4-yl)-methylamine;
2-Bromo-N-(4-dimethylamino-phenyl)-benzamide;
2-Chloro-N-(4-dimethylamino-phenyl)-nicotinamide;
2-(2-Dimethylamino-ethylamino)-N-(4-methoxy-phenyl)-nicotinamide;
2-(2-Dimethylamino-ethylamino)-N-(4-methoxy-phenyl)-benzamide;
2-(3-Diethylamino-ethylamino)-N-(4-methoxy-phenyl)-benzamide;
2-(3-Dimethylamino-propylamino)-N-(4-methoxy-phenyl)-benzamide;
2-(4-Hydroxy-butylamino)-N-(4-methoxy-phenyl)-benzamide;
2-(3-Imidazol-1-yl-propylamino)-N-(4-methoxy-phenyl)-benzamide;
2-Chloro-N-(4-trifluoromethoxy-phenyl)-nicotinamide;
2-Bromo-N-(4-trifluoromethoxy-phenyl)-benzamide;
2-(3-Imidazol-1-yl-propylamino)-N-(4-trifluoromethoxy-phenyl)-nicotinamide;
2-(2-Diethylamino-ethylamino)-N-(4-trifluoromethoxy-phenyl)-benzamide;
2-(3-Dimethylamino-propylamino)-N-(4-trifluoromethoxy-phenyl)-benzamide;
2-(3-Diethylamino-propylamino)-N-(4-trifluoromethoxy-phenyl)-benzamide;
2-(4-Hydroxy-butylamino)-N-(4-trifluoromethoxy-phenyl)-benzamide;
2-(6-Amino-hexylamino)-N-(4-trifluoromethoxy-phenyl)-benzamide;
2-(3-Imidazol-1-yl-propylamino)-N-(4-trifluoromethoxy-phenyl)-benzamide; and
2-(4-Diethylamino-1-methyl-butylamino)-N-(4-trifluoromethoxy-phenyl)-benzamide.

In a particularly preferred manner, the compound is selected among:
2-(2-Dimethylamino-ethylamino)-N-(4-methoxy-phenyl)-nicotinamide;
2-(2-Dimethylamino-ethylamino)-N-(4-methoxy-phenyl)-benzamide;
2-(3-Imidazol-1-yl-propylamino)-N-(4-trifluoromethoxy-phenyl)-benzamide.

According to another particular embodiment of said preferred embodiment, the inventive compound has formula (Ib) as follows:

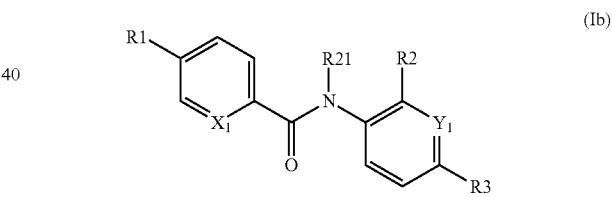

Preferably, said compound is selected among the group comprising:
4-Benzoylamino-N-(2-diethylamino-ethyl)-benzamide;
N-(3-Methyl-butyl)-3-[3-(4-methoxy-benzoylamino)-phenylamino]-benzamide;
N-{3-[(3-(4-Diethylaminomethyl-[1,2,3]triazol-1-yl)-phenylamino]-phenyl}-4-methoxy-benzamide;
N-(3-{4-[4-(3-Hydroxy-propyl)-[1,2,3]triazol-1-yl]-phenylamino}-phenyl)-4-methoxy-benzamide; and
N-(3-Methyl-butyl)-4-[3-(4-methoxybenzamido)-phenylamino]-benzamide.

In a particularly preferred manner, the compound is N-(3-Methyl-butyl)-3-[3-(4-methoxy-benzoylamino)-phenylamino]-benzamide or N-(3-{4-[4-(3-Hydroxy-propyl)-[1,2,3]triazol-1-yl]-phenylamino}-phenyl)-4-methoxy-benzamide.

According to a second preferred embodiment, the inventive compound has formula (II), preferably formula (IIa) as follows:

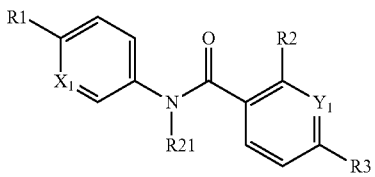

(IIa)

Preferably, said compound is selected among the group comprising:
2-(3-Dimethylamino-propylamino)-N-pyridin-3-yl-benzamide;
2-(3-Imidazol-1-yl-propylamino)-N-pyridin-3-yl-benzamide;
2-(2-Dimethylamino-ethylamino)-N-pyridin-3-yl-nicotinamide;
2-(2-Diethylamino-ethylamino)-N-pyridin-3yl-nicotinamide;
2-(3-Dimethylamino-propylamino)-N-pyridin-3-yl-nicotinamide;
2-(3-Diethylamino-propylamino)-N-pyridin-3-yl-nicotinamide;
2-(3-Imidazol-1-yl-propylamino)-N-pyridin-3-yl-nicotinamide;
2-Bromo-N-pyridin-3-yl-benzamide;
2-Bromo-N-(4-methoxy-phenyl)-benzamide;
2-Chloro-N-(4-methoxy-phenyl)-nicotinamide;
2-Chloro-N-pyridin-3-yl-nicotinamide; and
2-(3-Diethylamino-propylamino)-N-pyridin-3-yl-benzamide.

In a particularly preferred manner, the compound is 2-Bromo-N-(4-methoxy-phenyl)-benzamide or 2-Chloro-N-(4-methoxy-phenyl)-nicotinamide.

According to a third preferred embodiment, the inventive compound has formula (III), preferably formula (IIIa) as follows:

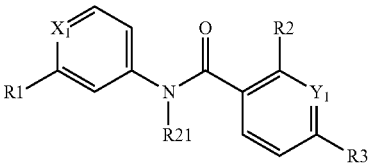

(IIIa)

Preferably, said compound is selected among the group comprising:
N-(4-pyridyl)-2-[6-(N'-(4-pyridylbenzamido)-phenylamino)-1-hydroxybutylamino]-benzamide;
2-(3-Diethylamino-propylamino)-N-pyridin-4-yl-nicotinamide;
2-(3-Imidazol-1-yl-propylamino)-N-pyridin-4-yl-nicotinamide;
N-(3-Diethylamino-propyl)-3-[3-(3-methoxybenzamido)-phenylamino]-benzamide;
3-(1-{3-[3-methoxybenzamido]-phenylamino]-phenyl}-1H-1,2,3-triazol-4-yl)-propan-1-ol;
N-(3-Diethylamino-propyl)-3-methyl-4-[3-(3-methoxybenzamido)-phenylamino]-benzamide;
N-(3-Methyl-butyl)-4-[3-(3-methoxybenzamido)-phenylamino]-benzamide;
3-(1-{4-[3-methoxybenzamido]-phenylamino]-phenyl}-1H-1,2,3-triazol-4-yl)-propan-1-ol;
(N-Diethylamino)-3-(1-{3-[3-methoxybenzamido]-phenylamino]-phenyl}-1H-1,2,3-triazol-4-yl)-methylamine;
3-(1-{(4-[(3-methoxybenzamido)-phenylamino]-phenyl}-1H-1,2,3-triazol-4-yl)-propan-1-ol;
N-(3-Diethylamino-propyl)-4-[4-(3-methoxybenzamido)-phenylamino]-benzamide;
N-(3-Diethylamino-propyl)-3-methyl-4-[4-(3-methoxybenzamido)-phenylamino]-benzamide;
N-(3-methyl-butyl)-3-methyl-4-[4-(3-methoxybenzamido)-phenylamino]-benzamide;
(N-Diethylamino)-3-(1-{4-[4-(3-methoxybenzamido)-phenylamino]-phenyl}-1H-1,2,3-triazol-4-yl)-methylamine;
3-(1-{(4-[3-methoxybenzamido)-phenylamino]-phenyl}-1H-1,2,3-triazol-4-yl)-propan-1-ol;
N-(3-Diethylamino-propyl)-3-[4-(3-methoxybenzamido)-phenylamino]-benzamide;
N-(3-methyl-butyl)-3-[4-(3-methoxybenzamido)-phenylamino]-benzamide;
2-Chloro-N-(3-methoxy-phenyl)-nicotinamide;
2-(3-Dimethylamino-propylamino)-N-(3-methoxy-phenyl)-nicotinamide;
2-Bromo-N-pyridin-4-yl-benzamide;
2-Bromo-N-(3-methoxy-phenyl)-benzamide;
2-Chloro-N-pyridin-4-yl-nicotinamide;
2-(2-Dimethylamino-ethylamino)-N-(3-methoxy-phenyl)-nicotinamide;
2-(2-Diethylamino-ethylamino)-N-(3-methoxy-phenyl)-nicotinamide;
2-(3-Diethylamino-propylamino)-N-(3-methoxy-phenyl)-nicotinamide;
2-(4-Hydroxy-butylamino)-N-(3-methoxy-phenyl)-nicotinamide;
2-(5-Hydroxy-pentyllamino)-N-(3-methoxy-phenyl)-nicotinamide;
2-(6-Amino-hexylamino)-N-(3-methoxy-phenyl)-nicotinamide;
2-(3-Imidazol-1-yl-propylamino)-N-(3-methoxy-phenyl)-nicotinamide;
2-(2-Dimethylamino-ethylamino)-N-(3-methoxy-phenyl)-benzamide;
2-(2-Diethylamino-ethylamino)-N-(3-methoxy-phenyl)-benzamide;
2-(4-Hydroxy-butylamino)-N-(3-methoxy-phenyl)-benzamide;
2-(4-Diethylamino-1-methyl-butylamino)-N-(3-methoxy-phenyl)-benzamide;
2-(2-Diethylamino-ethylamino)-N-pyridin-4-yl-benzamide;
2-(2-Diethylamino-ethylamino)-N-pyridin-4-yl-benzamide;
2-(3-Diethylamino-propylamino)-N-pyridin-4-yl-benzamide;
2-(3-Imidazol-1-yl-propylamino)-N-pyridin-4-yl-benzamide;
2-(2-Diethylamino-ethylamino)-N-pyridin-4-yl-nicotinamide; and
2-(3-Dimethylamino-propylamino)-N-pyridin-4-yl-nicotinamide.

In a particularly preferred manner, the compound is selected among:
N-(3-Diethylamino-propyl)-3-methyl-4-[3-(3-methoxybenzamido)-phenylamino]-benzamide;
N-(3-Methyl-butyl)-4-[3-(3-methoxybenzamido)-phenylamino]-benzamide;
2-Bromo-N-(3-methoxy-phenyl)-benzamide;
2-(6-Amino-hexylamino)-N-(3-methoxy-phenyl)-nicotinamide; and
2-(3-Imidazol-1-yl-propylamino)-N-(3-methoxy-phenyl)-nicotinamide.

According to a fourth preferred embodiment, the inventive compound has formula (IV).

Preferably, said compound is selected among the group comprising:

N-(3-Dimethylamino-propyl)-3-(4-trifluoromethoxy-phenylamino)-benzamide;
4-(4-Methoxy-phenylamino)-3-methyl-N-(3-methyl-butyl)-benzamide;
3-Methyl-N-(3-methyl-butyl)-4-(4-trifluoromethoxy-phenylamino)-benzamide;
N-(2-Dimethylamino-ethyl)-2-(4-trifluoromethoxy-phenylamino)-benzamide;
N-(2-Diethylamino-ethyl)-2-(4-trifluoromethoxyphenylamino)-benzamide;
N-(2-Diethylamino-propyl)-2-(4-trifluoromethoxy-phenylamino)-benzamide;
(N-Diethylamino)-{1-[4-(4-Methoxy-phenylamino)-phenyl]-1H-1,2,3-triazol-4-yl}-methylamine;
(N-Diethylamino)-{1-[4-(4-trifluoromethoxyphenylamino)-phenyl]-1H-1,2,3-triazol-4-yl}-methylamine;
(N-Diethylamino)-{1-[4-(4-N-dimethylamino-phenylamino)-phenyl]-1H-1,2,3-triazol-4-yl}-methylamine;
N-(3-Imidazol-1-yl-propyl)-2-(4-methoxy-phenylamino)-benzamide;
N-(3-Imidazol-1-yl-propyl)-2-(4-trifluoromethoxy-phenylamino)-benzamide;
2-(4-Dimethylamino-phenylamino)-N-(3-imidazol-1-yl-propyl)-benzamide;
N-(4-Diethylamino-1-methyl-butyl)-2-(4-dimethylaminophenylamino)-benzamide;
N-(2-Dimethylamino-ethyl)-4-(4-trifluoromethoxy-phenylamino)-benzamide;
N-(2-Dimethylamino-ethyl)-4-(4-dimethylamino-phenylamino)-benzamide;
N-(2-Dimethylamino-ethyl)-4-(4-methoxy-phenylamino)-3-methyl-benzamide;
N-(3-Diethylamino-propyl)-4-(4-methoxy-phenylamino)-benzamide;
N-(3-Diethylamino-propyl)-4-(4-methoxy-phenylamino)-3-methyl-benzamide;
N-(3-Diethylamino-propyl)-3-methyl-4-(4-trifluoromethoxy-phenylamino)-benzamide;
N-(3-Diethylamino-propyl)-4-(4-dimethylamino-phenylamino)-3-methyl-benzamide;
N-(2-Dimethylamino-ethyl)-3-methyl-4-(4-trifluoromethoxy-phenylamino)-benzamide;
3-{1-[4-(4-Methoxy-phenylamino)-phenyl]-1H-1,2,3-triazol-4-yl}-propan-1-ol;
(N-diethylamino)-{1-[3-(4-Methoxy-phenylamino)-phenyl]-1H-1,2,3-triazol-4-yl}-methylamine;
[4-(5-Chloro-1H-imidazol-2-yl)-2-methyl-phenyl]-(4-methoxy-phenyl)-amine;
N-(2-Diethylamino-ethyl)-4-(4-methoxy-phenylamino)-benzamide;
N-(2-Dimethylamino-ethyl)-2-(4-methoxy-phenylamino)-benzamide;
4-(4-Methoxy-phenylamino)-N-(3-methyl-butyl)-benzamide;
N-(3-Imidazol-1-yl-propyl)-4-(4-trifluoromethoxy-phenylamino)-benzamide;
[3-(4-Diethylaminomethyl-[1,2,3]triazol-1-yl)-phenyl]-(4-dimethylamino)-phenylamine;
N-(2-Diethylamino-ethyl)-2-(4-methoxy-phenylamino)-benzamide;
3-{(1-[3-(4-Trifluoromethoxy-phenylamino)-phenyl]-1H-[1,2,3]triazol-4-yl}-propan-1-ol; and
3-{1-[3-(4-Dimethylamino-phenylamino)-phenyl]-1H-[1,2,3]triazol-4-yl}-propan-1-ol In a particularly preferred way, the compound is selected among N-(2-Dimethylamino-ethyl)-4-(4-trifluoromethoxyphenylamino)-benzamide; [4-(5-Chloro-1H-imidazol-2-yl)-2-methyl-phenyl]-(4-methoxy-phenyl)-amine; and 4-(4-Methoxy-phenylamino)-N-(3-methyl-butyl)-benzamide.

According to a fifth preferred embodiment, the inventive compound has formula (V).

Preferably, said compound is selected among the group comprising:

N-(3-Dimethylamino-propyl)-3-(pyridin-3-ylamino)-benzamide;
3-Methyl-N-(3-methyl-butyl)-4-(pyridin-3-ylamino)-benzamide;
N-(3-Methyl-butyl)-4-(pyridin-3-ylamino)-benzamide;
(N-Diethylamino)-{1-[4-(pyridin-3-ylamino)-phenyl]-1H-1,2,3-triazol-4-yl}-methylamine;
N-(3-Imidazol-1-yl-propyl)-2-(pyridin-3-ylamino)-benzamide;
N-(2-Dimethylamino-ethyl)-4-(pyridin-3-ylamino)-benzamide;
N-(3-Diethylamino-propyl)-3-[3-(3-methoxybenzamido)-phenylamino]-benzamide;
3-(1-{(3-[(3-methoxybenzamido)-phenylamino]-phenyl}-1H-1,2,3-triazol-4-yl)-propan-1-ol;
N-(3-Diethylamino-propyl)-3-methyl-4-[3-(3-methoxybenzamido)-phenylamino]-benzamide;
N-(3-Methyl-butyl)-4-[3-(3-methoxybenzamido)-phenylamino]-benzamide;
3-(1-{4-[3-methoxybenzamido)-phenylamino]-phenyl}-1H-1,2,3-triazol-4-yl)-propan-1-ol;
(N-diethylamino)-3-(1-{3-[3-methoxybenzamido)-phenylamino]-phenyl}-1H-1,2,3-triazol-4-yl)-methylamine;
N-(3-Diethylamino-propyl)-3-methyl-4-(pyridin-3-ylamino)-benzamide;
N-(3-Diethylamino-propyl)-3-[3-(3-methoxybenzamido)-phenylamino]-benzamide;
N-(3-Methyl-butyl)-3-methyl-4-[3-(4-methoxybenzamido)-phenylamino]-benzamide;
(N-Diethylamino)-3-(1-{3-[4(4-methoxybenzamido)-phenylamino]-phenyl}-1H-1,2,3-triazol-4-yl)-methylamine;
4-Methyl-N-(3-methyl-butyl)-3-[(3-((E)-2-pyridin-4-yl-vinyl)-phenylamino]-benzamide;
N-(3-Diethylamino-propyl)-3-[(3-((E)-2-pyridin-4-yl-vinyl)-phenylamino]-benzamide;
N-(3-Methyl-butyl)-3-[3-((E)-2-pyridin-4-yl-vinyl)-phenylamino]-benzamide;
(N-diethylamino)-3-(1-{3-[3-((E)-2-Pyridin-4-yl-vinyl)-phenylamino]-phenyl}-1H-1,2,3-triazol-4-yl)-methylamine;
3-(1-{3-[3-((E)-2-Pyridin-4-yl-vinyl)-phenylamino]-phenyl}-1H-1,2,3-triazol-4-yl)-propan-1-ol;
N-(2-Dimethylamino-ethyl)-4-(4-trifluoromethoxyphenylamino)-benzamide;
N-(3-Diethylamino-propyl)-3-methyl-4-[3-((E)-2-pyridin-4-yl-vinyl)-phenylamino]-benzamide;
N-(3-Methyl-butyl)-4-[3-((E)-2-pyridin-4-yl-vinyl)-phenylamino]-benzamide;
N-(3-Dimethylamino-propyl)-4-(4-methoxy-phenylamino)-benzamide;
N-(2-Dimethylamino-ethyl)-2-(pyridin-3-ylamino)-benzamide;
N-(3-Diethylamino-propyl)-2-(pyridin-3-ylamino)-benzamide;
N-{3-[3-(3-Diethylamino-propylcarbamoyl)-phenylamino]-phenyl}-nicotinamide;

N-(3-Diethylamino-propyl)-3-[3-(pyridoyl)-phenylamino]-benzamide;
N-{3-[3-(3-Methyl-butylcarbamoyl)-phenylamino]-phenyl}-nicotinamide;
N-{3-[3-(4-Diethylaminomethyl-[1,2,3]triazol-1-yl)-phenylamino]-phenyl}-nicotinamide;
N-{3-[4-(3-Diethylamino-propylcarbamoyl)-phenylamino]-phenyl}-nicotinamide;
N-(3-Dimethylamino propyl)-2-(4-methoxy-phenylamino)-benzamide; and
N-(3-Dimethylamino propyl)-2-(pyridin-3-ylamino)benzamide.

In a particularly preferred manner, said compound is selected among the group comprising:
N-(2-Dimethylamino-ethyl)-4-(4-trifluoromethoxyphenylamino)-benzamide;
N-(2-Dimethylamino-ethyl)-4-(pyridin-3-ylamino)-benzamide;
N-(3-Diethylamino-propyl)-3-methyl-4-[3-(3-methoxybenzamido)-phenylamino]-benzamide; and
N-(3-Methyl-butyl)-4-[3-(3-methoxybenzamido)-phenylamino]-benzamide.

According to a sixth preferred embodiment, the inventive compound has formula (VI).

Preferably, said compound is selected among the group comprising:
N-(2-Dimethylamino-ethyl)-2-(pyridin-4-ylamino)-benzamide;
N-(3-Dimethylamino-propyl)-3-(3-methoxy-phenylamino)-benzamide;
N-(3-Dimethylamino-propyl)-3-(4-methoxy-phenylamino)-benzamide;
4-(3-Methoxy-phenylamino)-3-methyl-N-(3-methyl-butyl)-benzamide;
3-Methyl-N-(3-methyl-butyl)-4-(pyridin-4-ylamino)-benzamide;
N-(3-Methyl-butyl)-4-(pyridin-4-ylamino)-benzamide;
(N-Diethylamino)-{1-[4-(3-Methoxy-phenylamino)-phenyl]-1H-1,2,3-triazol-4-yl}-methylamine;
N-(2-Dimethylamino-ethyl)-3-(3-methoxy-phenylamino)-benzamide;
N-(3-Imidazol-1-yl-propyl)-2-(3-methoxy-phenylamino)-benzamide;
N-(2-Dimethylamino-ethyl)-4-(3-methoxy-phenylamino)-benzamide;
N-(3-Diethylamino-propyl)-4-(3-methoxy-phenylamino)-3-methyl-benzamide;
3-{1-[4-(3-Methoxy-phenylamino)-phenyl]-1H-1,2,3-triazol-4-yl}-propan-1-ol;
N-(3-Diethylamino-propyl)-3-[4-((E)-2-pyridin-4-yl-vinyl)-phenylamino]-benzamide;
N-(3-Methyl-butyl)-3-[4-((E)-2-pyridin-4-yl-vinyl)-phenylamino]-benzamide;
(N-Diethylamino)-3-(1-{3-[4-((E)-2-Pyridin-4-yl-vinyl)-phenylamino]-phenyl}-1H-1,2,3-triazol-4-yl)-methylamine;
3-(1-{3-[4-((E)-2-Pyridin-4-yl-vinyl)-phenylamino]-phenyl}-1H-1,2,3-triazol-4-yl)-propan-1-ol;
N-(3-Diethylamino-propyl)-3-methyl-4-[4-((E)-2-pyridin-4-yl-vinyl)-phenylamino]-benzamide;
3-Methyl-N-(3-methyl-butyl)-4-[4-((E)-2-pyridin-4-yl-vinyl)-phenylamino]-benzamide;
3-(1-{4-[4-((E)-2-Pyridin-4-yl-vinyl)-phenylamino]-phenyl}-1H-1,2,3-triazol-4-yl)-propan-1-ol;
3-(1-{4-[3-methoxybenzamido)-phenylamino]-phenyl}-1H-1,2,3-triazol-4-yl)-propan-1-ol;
N-(3-Diethylamino-propyl)-4-[4-(3-methoxybenzamido)-phenylamino]-benzamide;
N-(3-Diethylamino-propyl)-3-methyl-4-[4-(3-methoxybenzamido)-phenylamino]-benzamide;
N-(3-methyl-butyl)-3-methyl-4-[4-(3-methoxybenzamido)-phenylamino]-benzamide;
(N-Diethylamino)-3-(1-{4-[4-(3-methoxybenzamido)-phenylamino]-phenyl}-1H-1,2,3-triazol-4-yl)-methylamine;
3-(1-{4-[3-methoxybenzamido)-phenylamino]-phenyl}-1H-1,2,3-triazol-4-yl)-propan-1-ol;
N-(3-Diethylamino-propyl)-3-[4-(3-methoxybenzamido)-phenylamino]-benzamide;
N-(3-methyl-butyl)-3-[4-(3-methoxybenzamido)-phenylamino]-benzamide;
4-(3-Methoxy-phenylamino)-N-(3-methyl-butyl)-benzamide;
[3-(4-Diethylaminomethyl-[1,2,3]triazol-1-yl)-phenyl]-(3-methoxy)-phenylamine;
N-(3-Diethylamino-propyl)-3-[4-(4-methoxy-benzoylamino)-phenylamino]-3-methyl-benzamide;
N-(3-Methyl-butyl)-3-[4-(4-methoxy-benzoylamino)-phenylamino]-benzamide;
(N-Diethylamino)-3-(1-{4-[(4-methoxybenzamido)-phenylamino]-phenyl}-1H-1,2,3-triazol-4-yl)-methylamine;
3-(1-{4-[(4-methoxybenzamido)-phenylamino]-phenyl}-1H-1,2,3-triazol-4-yl)-propan-1-ol;
N-(3-Diethylamino-propyl)-4-[4-(4-methoxy-benzoylamino)-phenylamino]-3-methyl-benzamide;
N-(3-Methyl-butyl)-4-[4-(4-methoxy-benzoylamino)-phenylamino]-benzamide; and
N-{4-[3-(3-Methyl-butylcarbamoyl)-phenylamino]-phenyl}-nicotinamide.

In a particularly preferred manner, said compound is selected among the group comprising:
N-(3-Diethylamino-propyl)-3-[4-(4-methoxy-benzoylamino)-phenylamino]-3-methyl-benzamide;
N-(3-Methyl-butyl)-3-[4-(4-methoxy-benzoylamino)-phenylamino]-benzamide;
3-(1-{4-[(4-methoxybenzamido)-phenylamino]-phenyl}-1H-1,2,3-triazol-4-yl)-propan-1-ol;
N-(3-Diethylamino-propyl)-4-[4-(4-methoxy-benzoylamino)-phenylamino]-3-methyl-benzamide; and
N-(3-Methyl-butyl)-4-[4-(4-methoxy-benzoylamino)-phenylamino]-benzamide.

According to a seventh preferred embodiment, the inventive compound has formula (VII).

Preferably, said compound is selected among the group comprising:
N-(4-Hydroxy-butyl)-3-((E)-2-pyridin-2-yl-vinyl)-benzamide;
2-(1-{(4-[(E)-2-(4-Methoxy-phenyl)-vinyl]-phenyl}-1H-1,2,3-triazol-4-yl)-propan-2-ol;
N-(4-Hydroxy-butyl)-3-[2-(4-methoxy-phenyl)-vinyl]-benzamide;
N-(3-Diethylamino-propyl)-3-[4-((E)-2-pyridin-2-yl-vinyl)-phenylamino]-benzamide;
N-(3-Methyl-butyl)-3-[4-((E)-2-pyridin-2-yl-vinyl)-phenylamino]-benzamide;
N-(3-Diethylamino-propyl)-4-[4-((E)-2-pyridin-2-yl-vinyl)-phenylamino]-benzamide;
N-(3-Methyl-butyl)-4-[4-((E)-2-pyridin-2-yl-vinyl)-phenylamino]-benzamide; and
3-(1-{3-[4-((E)-2-Pyridin-2-ylvinyl)-phenylamino]-phenyl}-1H-1,2,3-triazol-4-yl)-propan-1-ol.

In a particularly preferred manner, said compound is N-(3-Methyl-butyl)-4-[4-((E)-2-pyridin-2-yl-vinyl)-phenylamino]-benzamide.

According to an eighth preferred embodiment, the inventive compound has formula (IX).

Preferably, said compound is selected among the group comprising:

N-(3-Diethylamino-propyl)-3-[4-((E)-2-pyridin-4-yl-vinyl)-phenylamino]-benzamide;
N-(3-Methyl-butyl)-3-[4-((E)-2-pyridin-4-yl-vinyl)-phenylamino]-benzamide;
(N-Diethylamino)-3-(1-{3-[4-((E)-2-Pyridin-4-yl-vinyl)-phenylamino]-phenyl}-1H-1,2,3-triazol-4-yl)-methylamine;
3-(1-{3-[4-((E)-2-Pyridin-4-yl-vinyl)-phenylamino]-phenyl}-1H-1,2,3-triazol-4-yl)-propan-1-ol;
N-(3-Diethylamino-propyl)-3-methyl-4-[4-((E)-2-pyridin-4-yl-vinyl)-phenylamino]-benzamide;
3-Methyl-N-(3-methyl-butyl)-4-[4-((E)-2-pyridin-4-yl-vinyl)-phenylamino]-benzamide;
3-(1-{4-[4-((E)-2-Pyridin-4-yl-vinyl)-phenylamino]-phenyl}-1H-1,2,3-triazol-4-yl)-propan-1-ol;
4-Methyl-N-(3-methyl-butyl)-3-[(3-((E)-2-pyridin-4-yl-vinyl)-phenylamino]-benzamide;
N-(3-Diethylamino-propyl)-3-[3-((E)-2-pyridin-4-yl-vinyl)-phenylamino]-benzamide;
N-(3-Methyl-butyl)-3-[3-((E)-2-pyridin-4-yl-vinyl)-phenylamino]-benzamide;
(N-diethylamino)-3-(1-{3-[3-((E)-2-Pyridin-4-yl-vinyl)-phenylamino]-phenyl}-1H-1,2,3-triazol-4-yl)-methylamine;
3-(1-{3-[3-((E)-2-Pyridin-4-yl-vinyl)-phenylamino]-phenyl}-1H-1,2,3-triazol-4-yl)-propan-1-ol;
N-(3-Diethylamino-propyl)-3-methyl-4-[3-((E)-2-pyridin-4-yl-vinyl)-phenylamino]-benzamide;
N-(3-Methyl-butyl)-4-[3-((E)-2-pyridin-4-yl-vinyl)-phenylamino]-benzamide;
N-(3-Diethylaminol-propyl)-3-[3-((E)-(4-methoxy-styryl)-phenylamino]-benzamide;
N-(3-Methyl-butyl)-3-[3-((E)-(4-methoxy-styryl)-phenylamino]-benzamide;
N-(3-Diethylaminol-propyl)-3-methyl-4-[3-((E)-(4-methoxy-styryl)-phenylamino]-benzamide;
N-(3-Methyl-butyl)-3-methyl-4-[(3-((E)-(4-methoxy-styryl)-phenylamino]-benzamide;
N-(3-Methyl-butyl)-4-[3-((E)-(4-methoxy-styryl)-phenylamino]-benzamide;
N-(3-Diethylamino-propyl)-3-[3-((E)-2-pyridin-2-yl-vinyl)-phenylamino]-benzamide;
N-(3-Methyl-butyl)-3-[3-((E)-2-pyridin-2-yl-vinyl)-phenylamino]-benzamide;
3-(1-{3-[4-((E)-2-Pyridin-4-ylvinyl)-phenylamino]-phenyl}-1H-1,2,3-triazol-4-yl)-propan-1-ol;
N-(3-Diethylamino-propyl)-4-[3-((E)-2-pyridin-2-yl-vinyl)-phenylamino]-benzamide;
N-(3-Methyl-butyl)-3-methyl-4-[3-((E)-2-pyridin-2-yl-vinyl)-phenylamino]-benzamide; and
3-(1-{3-[3-((E)-2-Pyridin-2-ylvinyl)-phenylamino]-phenyl}-1H-1,2,3-triazol-4-yl)-propan-1-ol.

A second object of the invention consists of a pharmaceutical composition comprising at least one compound as described above and, optionally, a pharmaceutically acceptable support.

As examples of pharmaceutically acceptable supports, the composition can include emulsions, microemulsions, oil in water emulsions, anhydrous lipids and water in oil emulsions or other types of emulsions.

The inventive composition can further include one or more additives such as diluents, excipients, stabilizers and preservatives. Such additives are well known to those skilled in the art and are described notably in "*Ullmann's Encyclopedia of Industrial Chemistry, 6th Ed.*" (various editors, 1989-1998, Marcel Dekker) and in "*Pharmaceutical Dosage Forms and Drug Delivery Systems*" (ANSEL et al., 1994, WILLIAMS & WILKINS).

A third object consists of the use of at least one compound as described above in preparing a drug to treat, in a subject, a disease resulting from at least one splicing anomaly.

As used in the present application, the term "subject" refers to a mammal such as a rodent, cat, dog, primate or human, preferably said subject is a human.

Preferably, the inventive compounds have the ability to inhibit pre-messenger RNA splicing processes that are either constitutive or, more specifically, dependent on regulating sequences known as an ESE (exonic splicing enhancer), ISE (intronic splicing enhancer), ESS (exonic splicing silencer) and ISS (intronic splicing silencer).

In a particularly preferred way, splicing processes are either constitutive and/or or dependent on ESE regulating sequences.

Diseases related to the splicing process include genetic diseases resulting from the alteration of splicing processes, most notably Frasier syndrome, frontotemporal dementia related to chromosome 17 (a form of Parkinson's), Leigh syndrome (a type of encephalopathy), atypical cystic fibrosis, certain neuropathologies including most notably Alzheimer's related to a mutation of the Tau protein, amyotrophy which affects the SMN (survival motor neuron) gene, depression related to dysregulation of serotonin splicing, and certain metastatic cancers in which the overall splicing process is affected (most notably in epithelial cancer including breast cancer, colon cancer, pancreas cancer, liver cancer, prostate cancer, uterus cancer and certain lymphomas).

In a particular embodiment, the use of the at least one compound of the invention is for preparing a drug to treat, in a subject, a cancer, most preferably a metastatic cancer, which cancer is selected in the group comprising breast cancer, colon cancer, pancreas cancer, liver cancer, prostate cancer, uterus cancer.

In light of recent results, it appears that many splicing process anomalies appear with aging.

Additionally, it is thus highly probable that said anomalies play a role in the appearance of pathologies with aging. Examples of diseases that appear with aging and that are likely related to the splicing process include atherosclerosis, insulin resistant type II diabetes, cataracts, osteoporosis and aging of the skin Diseases related to the splicing process also include diseases of viral origin for which ESE sequences are identified for splicing. An example of such diseases of viral origin is AIDS.

In another particular embodiment, the use of the at least one compound of the invention is for preparing a drug to treat, in a subject, diseases of viral origin for which ESE sequences are identified for splicing, preferably AIDS.

Other pathologies associated with gene mutations, and which can be treated can exon skipping may also be treated by the compounds of the invention. As an example of such pathologies, one may cite Duchenne muscular dystrophy (DMD).

In still another particular embodiment, the use of the at least one compound of the invention is for preparing a drug to treat, in a subject, diseases associated with gene mutations which may be treated by exon skipping, preferably Duchenne muscular dystrophy (DMD).

Preferentially, the disease related to a splicing anomaly is selected among the group comprising AIDS, cancer, Leigh syndrome characterized by a mitochondrial defect, early-aging syndrome (progeria) and Duchenne muscular dystrophy.

A fourth object of the invention relates to a therapeutic method for treating a subject for a genetic disease resulting from splicing anomalies comprising the administration of a therapeutically effective quantity of a pharmaceutical composition as described above.

A "therapeutically effective quantity" means a quantity that induces inhibition of the splicing of the pre-mRNAs of interest. Those skilled in the art will be able to determine said therapeutically effective quantity based on their general knowledge and on the methods described in the examples.

The compounds can be administered by any mode of administration such as, for example, by intramuscular, intravenous or oral route, etc.

In one embodiment according to the invention, said composition further includes an excipient making it possible to formulate the inventive compounds in such a way that said composition is provided in solid or liquid form to be prepared and administered by intravenous route.

The inventive compounds preferably will be administered by intravenous route at a concentration of 80-100 mg/m$^2$. The concentration will be chosen by those skilled in the art according to the organ or tissue to be treated, the state of advancement of the disease and the targeting mode used.

EXAMPLES

The following examples are provided as illustrations and in no way limit the scope of this invention.

Example 1

Development of IDC16 Derivative Compounds

The inventors have shown that compound IDC16 (BAKKOUR et al., cited above, 2007) interacts functionally with the SF2/ASF complex and thus contributes to blocking alternative splicing during HIV replication, leading to the termination of the production of Tat protein.

Accordingly, the family of polycyclic indoles, to which compound IDC16 belongs, is known to exhibit the properties of DNA intercalating agents. Such compounds thus present a risk in terms of undesirable side effects.

The inventors thus sought to develop novel molecules exhibiting activity comparable to IDC16, in terms of activity inhibiting HIV splicing, but while not exhibiting the characteristics of DNA intercalating agents.

In their initial hypothesis, the inventors considered that the two polar heterocycles at the two ends of compound IDC16 were associated with its activity and that the two median rings were of less importance.

Based on this hypothesis, the inventors considered that:
the nitrogen of the indoline and of the D ring of IDC16 might act as acceptors of hydrogen bonds;
the N-methylated 4-pyridinone motif might be preserved in the analogues;
the flat tetracyclic geometry was not optimal and it might be wise to replace the B and C rings by other motifs to limit DNA intercalating properties.

Example 2

Method for Synthesizing the Compounds of the Present Invention

[A1.] The list of the compounds used in the present study is provided in table I below.

TABLE I

| Compound | Structure | MW | Structure | Compound |
|---|---|---|---|---|
| C1 | 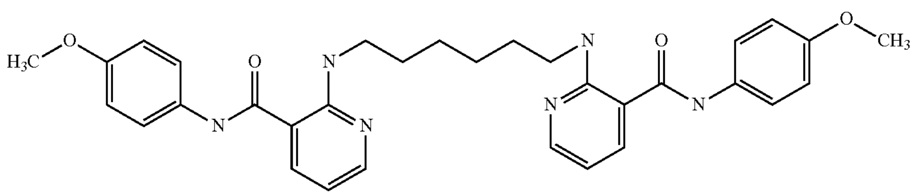 | 568.6815 | C32H36N6O4 | N-(4-Methoxy-phenyl)-2-[6-(N'-(4-Methoxyphenylnicotinamido)-pyridin-2-ylamino)-hexylamino]-nicotinamide |
| C2 | 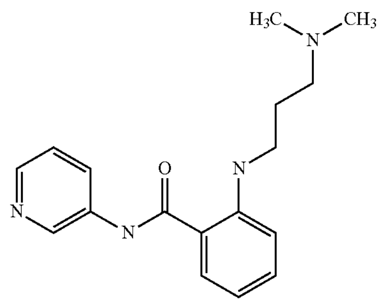 [SMILES: CN(C)CCCNc1ccccc1C(=O)Nc1cccnc1] | 298.3911 | C17H22N4O | 2-(3-Dimethylaminopropylamino)-N-pyridin-3-ylbenzamide |
| C3 | 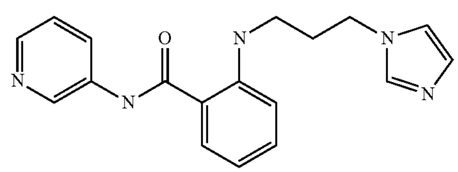 [SMILES: O=C(Nc1cccnc1)c1ccccc1NCCCn1ccnc1] | 321.385 | C18H19N5O | 2-(3-Imidazol-1-ylpropylamino)-N-pyridin-3-ylbenzamide |
| C4 | 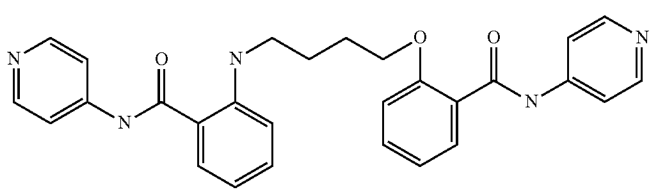 [SMILES: O=C(Nc1ccncc1)c1ccccc1NCCCCOc1ccccc1C(=O)Nc1ccncc1] | 481.5591 | C28H27N5O3 | N-(4-pyridyl)-2-[6-(N'-(4-pyridylbenzamido)-phenylamino)-1-hydroxybutylamino]-benzamide |

TABLE 1-continued

| Compound | Structure | MW | Structure | Compound |
|---|---|---|---|---|
| C5 | 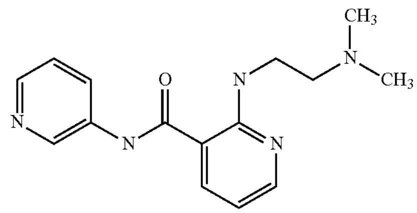 [SMILES: CN(C)CCNc1ncccc1C(=O)Nc1cccnc1] | 285.3516 | C15H19N5O | 2-(2-Dimethylaminoethylamino)-N-pyridin-3-ylnicotinamide |
| C6 | 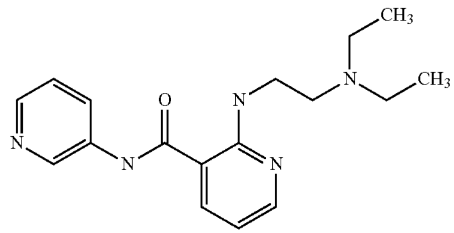 [SMILES: CCN(CC)CCNc1ncccc1C(=O)Nc1cccnc1] | 313.4058 | C17H23N5O | 2-(2-Diethylaminoethylamino)-N-pyridiyl-ylnicotinamide |
| C7 | 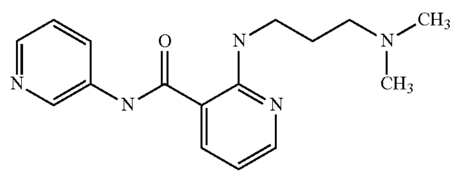 | 299.3787 | C16H21N5O | 2-(3-Dimethylaminopropylamino)-N-pyridin-3-ylnicotinamide |
| C8 | 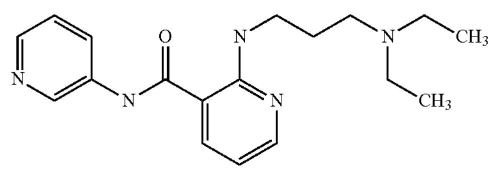 [SMILES: CCN(CC)CCCNc1ncccc1C(=O)Nc1cccnc1] | 327.4329 | C18H25N5O | 2-(3-Diethylaminopropylamino)-N-pyridiyl-ylnicotinamide |
| C9 | 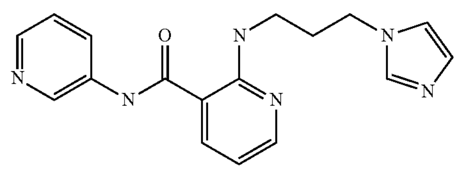 [SMILES: O=C(Nc1cccnc1)c1cccnc1NCCCn1ccnc1] | 322.3726 | C17H18N6O | 2-(3-Imidazol-1-ylpropylamino)-N-pyridin-3-ylnicotinamide |

TABLE 1-continued

| Compound | Structure | MW | Structure | Compound |
|---|---|---|---|---|
| C10 | 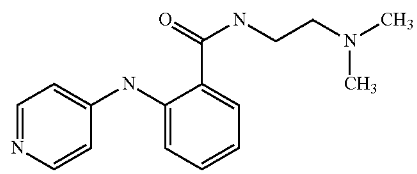 [SMILES: CN(C)CCNC(=O)c1ccccc1Nc1ccncc1] | 284.364 | C16H20N4O | N-(2-Dimethylamino-ethyl)-2-(pyridin-y4-ylamino)-benzamide |
| C11 | 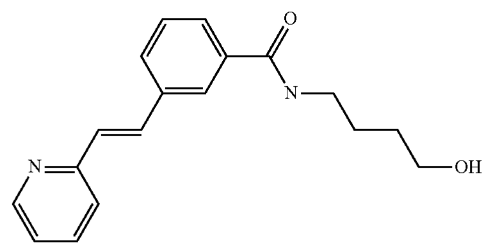 [SMILES: O=C(NCCCCO)c1cccc(/C=C/c2ccccn2)c1] | 296.3723 | C18H20N2O2 | N-(4-Hydroxy-butyl)-3-((E)-2-pyridin-2-yl-vinyl)-benzamide |
| C12 | 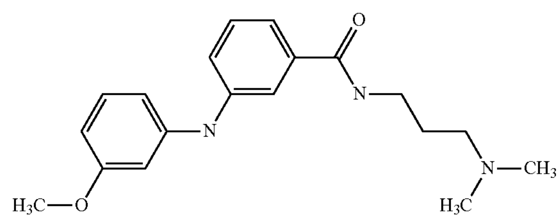 | 327.43 | C19H25N3O2 | N-(3-Dimethylamino-propyl)-3-(3-methoxy-phenylamino)-benzamide |
| C13 | 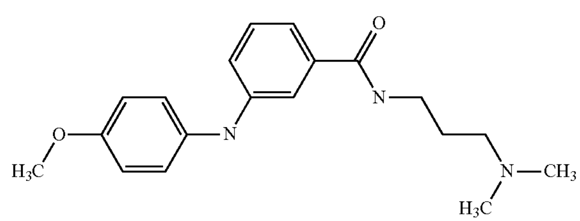 | 327.43 | C19H25N3O2 | N-(3-Dimethylamino-propyl)-3-(4-methoxy-phenylamino)-benzamide |

TABLE 1-continued

| Compound | Structure | MW | Structure | Compound |
|---|---|---|---|---|
| C14 | 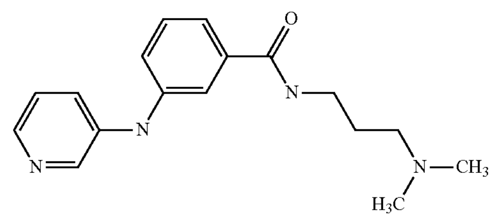 | 298.3911 | C17H22N4O | N-(3-Dimethylamino-propyl)-3-(pyridin-3-ylamino)-benzamide |
| C15 | 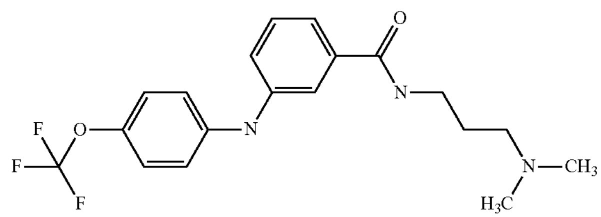 | 381.4013 | C19H22F3N3O2 | N-(3-Dimethylamino-propyl)-3-(4-trifluoromethoxyphenylamino)-benzamide |
| C16 | 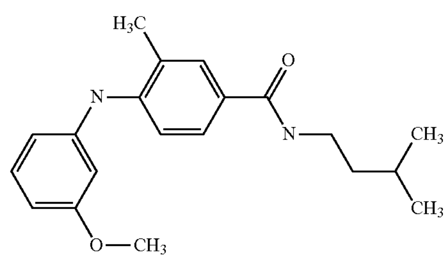 | 326.4424 | C20H26N2O2 | 4-(3-Methoxy-phenylamino)-3-methyl-N-(3-methyl-butyl)-benzamide |
| C17 | 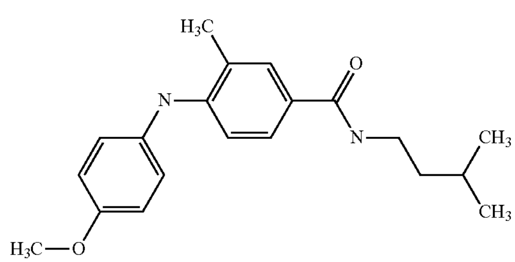 | 326.4424 | C20H26N2O2 | 4-(4-Methoxy-phenylamino)-3-methyl-N-(3-methyl-butyl)-benzamide |

TABLE 1-continued
| Compound | Structure | MW | Structure | Compound |
|---|---|---|---|---|
| C18 | 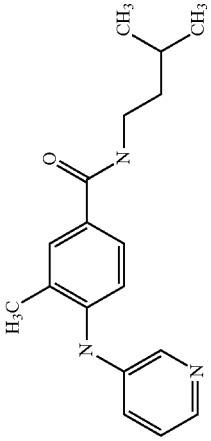 | 297.4035 | C18H23N3O | 3-Methyl-N-(3-methyl-butyl)-4-(pyridin-3-ylamino)-benzamide |
| C19 | 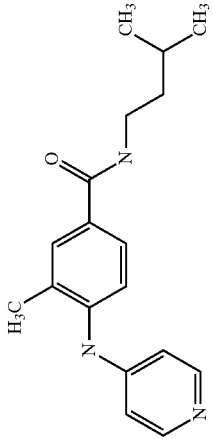 | 297.4035 | C18H23N3O | 3-Methyl-N-(3-methyl-butyl)-4-(pyridin-4-ylamino)-benzamide |
| C20 | 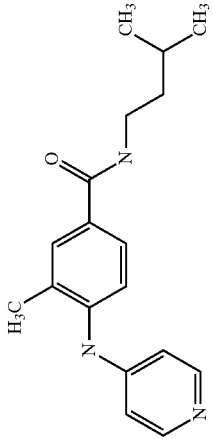 | 380.4137 | C20H23F3N2O2 | 3-Meethyl-N-(3-methyl-butyl)-4-(4-trifluoromethoxyphenylamino)-benzamide |
| C21 | 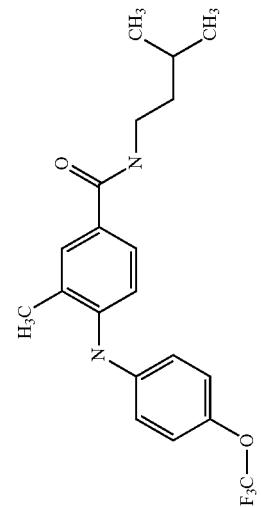 | 283.3764 | C17H21N3O | N-(3-Methyl-butyl)-4-(pyriidn-3-ylamino)-benzamide |

TABLE 1-continued

| Compound | Structure | MW | Structure | Compound |
|---|---|---|---|---|
| C22 | 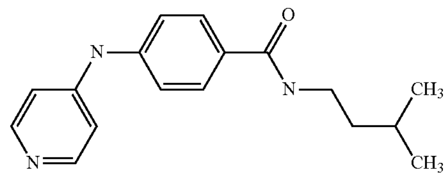 | 283.3764 | C17H21N3O | N-(3-Methyl-butyl)-4-(pyridin-4-ylamino)-benzamide |
| C23 | 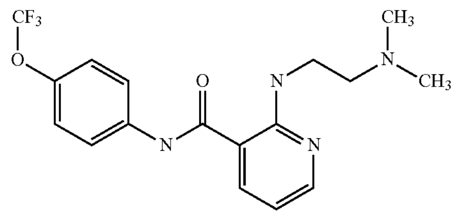 [SMILES: CN(C)CCNc1ncccc1C(=O)Nc1ccc(OC(F)(F)F)cc1] | 368.3618 | C17H19F3N4O2 | 2-(2-Dimethylaminoethylamino)-N-(4-trifluoromethoxy-phenyl)-nicotinamide |
| C24 | 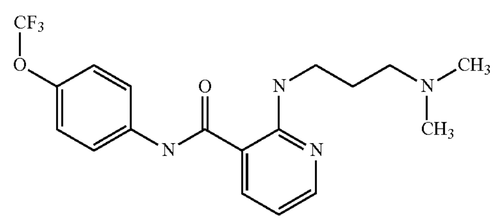 [SMILES: CN(C)CCCNc1ncccc1C(=O)Nc1ccc(OC(F)(F)F)cc1] | 382.3889 | C18H21F3N4O2 | 2-(3-Dimethylaminopropylamino)-N-(4-trifluoromethoxy-phenyl)-nicotinamide |
| C25 | 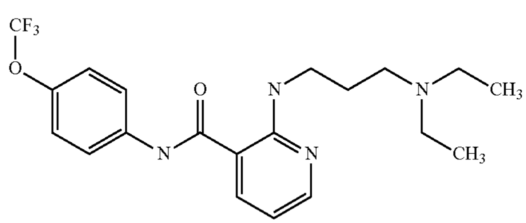 [SMILES: CCN(CC)CCCNc1ncccc1C(=O)Nc1ccc(OC(F)(F)F)cc1] | 410.4431 | C20H25F3N4O2 | 2-(3-Diethylaminopropylamino)-N-(4-trifluoromethoxy-phenyl)-nicotinamide |

TABLE I-continued

| Compound | Structure | MW | Structure | Compound |
|---|---|---|---|---|
| C26 | 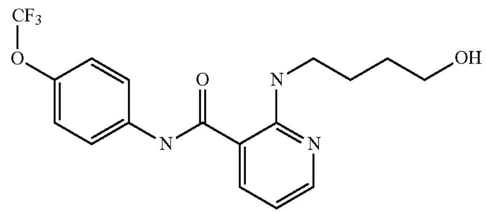 [SMILES: O=C(Nc1ccc(OC(F)(F)F)cc1)c1cccnc1NCCCCO] | 369.3465 | C17H18F3N3O3 | 2-(4-Hydroxy-butylamino)-N-(4-trifluoromethoxy-phenyl)-nicotinamide |
| C27 | 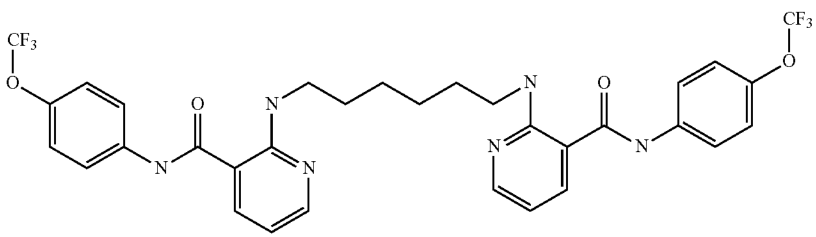 [SMILES: O=C(Nc1ccc(OC(F)(F)F)cc1)c1cccnc1NCCCCCCNc1ncccc1C(=O)Nc1ccc(OC(F)(F)F)cc1] | 676.6241 | C32H30F6N6O4 | N-(4-Trifluoromethoxyphenyl)-2-(N'-(4-Trifluoromethoxyphenylnicotinamido)-pyridin-2-ylamino)-hexylamino]-nicotinamide |
| C28 | 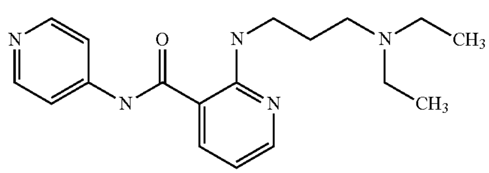 [SMILES: CCN(CC)CCCNc1ncccc1C(=O)Nc1ccncc1] | 327.4329 | C18H25N5O | 2-(3-Diethylaminopropylamino)-N-pyridin-ylnicotinamide |
| C29 | 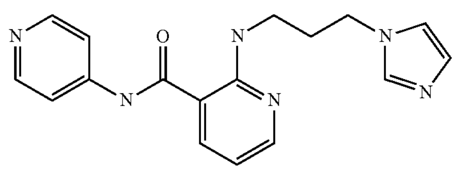 [SMILES: O=C(Nc1ccncc1)c1cccnc1NCCCn1ccnc1] | 322.3726 | C17H18N6O | 2-(3-Imidazol-1-ylpropylamino)-N-pyridin-ylnicotinamide |

TABLE 1-continued

| Compound | Structure | MW | Structure | Compound |
|---|---|---|---|---|
| C30 | 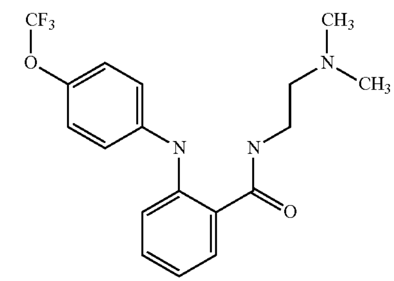 [SMILES: CN(C)CCNC(=O)c1ccccc1Nc1ccc(OC(F)(F)F)cc1] | 367.3742 | C18H20F3N3O2 | N-(2-Dimethylamino-ethyl)-2-(4-trifluoromethoxyphenylamino)-benzamide |
| C31 | 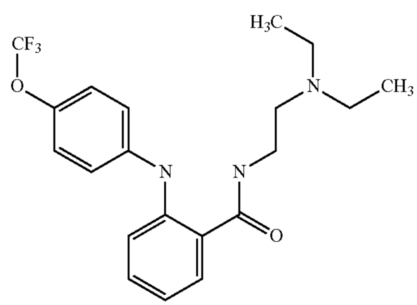 [SMILES: CCN(CC)CCNC(=O)c1ccccc1Nc1ccc(OC(F)(F)F)cc1] | 395.4284 | C20H24F3N3O2 | N-(2-Diethylamino-ethyl)-2-(4-trifluoromethoxyphenylamino)-benzamide |
| C32 | 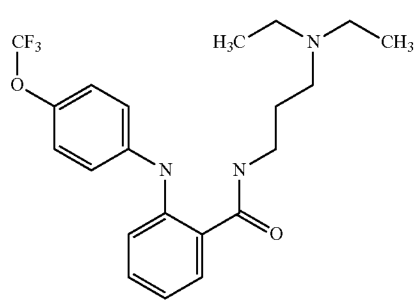 [SMILES: CCN(CC)CCCNC(=O)c1ccccc1Nc1ccc(OC(F)(F)F)cc1] | 409.4555 | C21H26F3N3O2 | N-(2-Diethylamino-propyl)-2-(4-trifluoromethoxyphenylamino)-benzamide |

TABLE 1-continued

| Compound | Structure | MW | Structure | Compound |
|---|---|---|---|---|
| C33 | 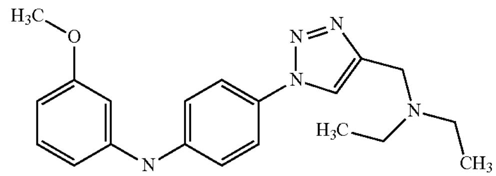 | 351.4552 | C20H25N5O | (N-Diethylamino)-{1-[4-(3-Methoxy-phenylamino)-phenyl]-1H-1,2,3-triazol-4-yl}-methylamine |
| C34 | 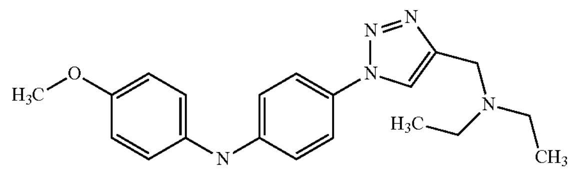 | 351.4552 | C20H25N5O | (N-Diethylamino)-{1-[4-(4-Methoxy-phenylamino)-phenyl]-1H-1,2,3-triazol-4-yl}-methylamine |
| C35 | 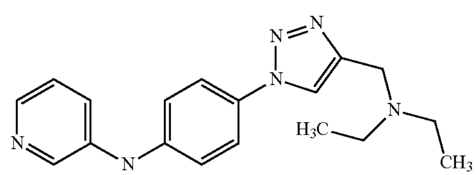 | 322.4162 | C18H22N6 | (N-Diethylamino)-{1-[4-(pyridin-3-ylamino)-phenyl]-1H-1,2,3-triazol-4-yl}-methylamine |
| C36 | 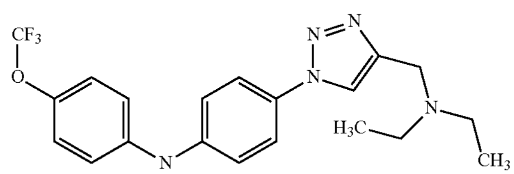 | 405.4264 | C20H22F3N5O | (N-Diethylamino)-{1-[4-(4-trifluoromethoxy-phenylamino)-phenyl]-1H-1,2,3-triazol-4-yl]-methylamine |
| C37 | 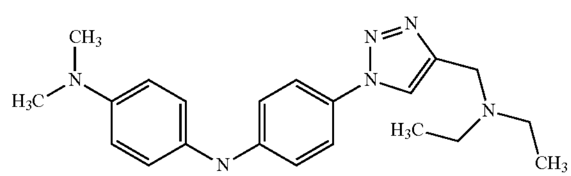 | 364.4975 | C21H28N6 | (N-Diethylamino)-{1-[4-(4-Ndimethylaminophenylamino)-phenyl]-1H-1,2,3-triazol-4-yl}-methylamine |

TABLE 1-continued

| Compound | Structure | MW | Structure | Compound |
|---|---|---|---|---|
| C38 | 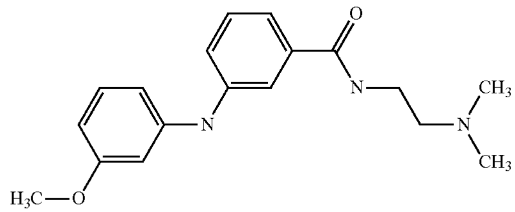 | 313.4029 | C18H23N3O2 | N-(2-Dimethylamino-ethyl)-3-(3-methoxy-phenylamino)-benzamide |
| C39 | 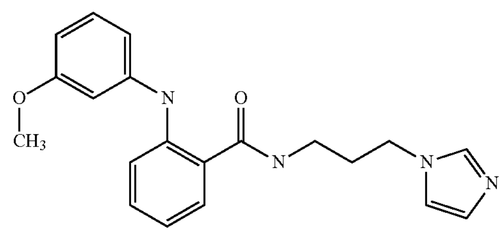 [SMILES: COc1cccc(Nc2ccccc2C(=O)NCCCn2ccnc2)c1] | 350.4239 | C20H22N4O2 | N-(3-Imidazol-1-yl-propyl)-2-(3-methoxy-phenylamino)-benzamide |
| C40 | 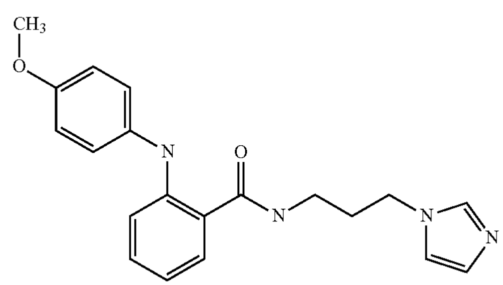 [SMILES: COc1ccc(Nc2ccccc2C(=O)NCCCn2ccnc2)cc1] | 350.4239 | C20H22N4O2 | N-(3-Imidazol-1-yl-propyl)-2-(4-methoxy-phenylamino)-benzamide |
| C41 | 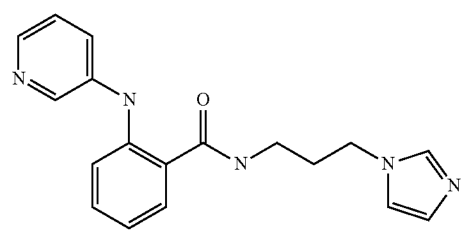 [SMILES: O=C(NCCCn1ccnc1)c1ccccc1Nc1cccnc1] | 321.385 | C18H19N5O | N-(3-Imidazol-1-yl-propyl)-2-(pyriidn-3-ylamino)-benzamide |

TABLE 1-continued

| Compound | MW | Structure | Compound |
|---|---|---|---|
| C42 | 404.3952 | C20H19F3N4O2 | N-(3-Imidazol-1-yl-propyl)-2-(4-trifluoromethoxyphenylamino)-benzamide |
| C43 | 363.4663 | C21H25N5O | 2-(4-Dimethylaminophenylamino)-N-(3-imidazol-1-yl-propyl)-benzamide |
| C44 | 335.4093 | C20H21N3O2 | 2-(1-{4-[(E)-2-(4-Methoxyphenyl)-vinyl]-phenyl}-1H-1,2,3-triazol-4-yl)-propan-2-ol |

TABLE 1-continued

| Compound | Structure | MW | Structure | Compound |
|---|---|---|---|---|
| C45 | 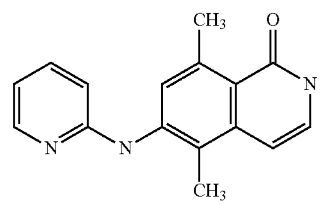 [SMILES: Cc1c(Nc2ccccn2)cc(C)c2c(=O)[nH]ccc12] | 265.3175 | C16H15N3O | 5,8-Dimethyl-6-(pyridin-2-ylamino)-2H-isoquinolin-1-one |
| C46 | 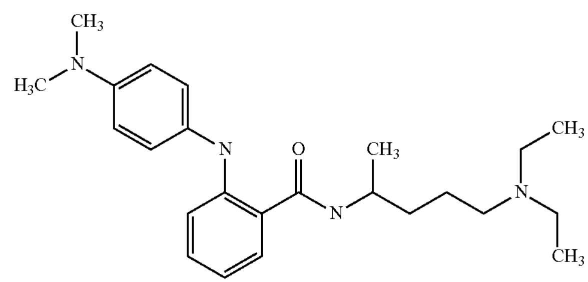 [SMILES: CCN(CC)CCCC(C)NC(=O)c1ccccc1Nc1ccc(N(C)C)cc1] | 396.5807 | C24H36N4O | N-(4-Diethylamino-1-methylbutyl)-2-(4-dimethylaminophenylamino)-benzamide |
| C47 | 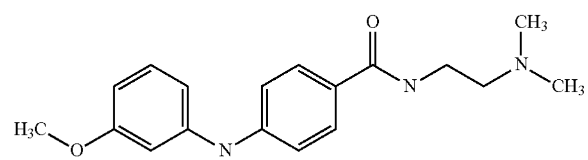 | 313.4029 | C18H23N3O2 | N-(2-Dimethylamino-ethyl)-4-(3-methoxy-phenylamino)-benzamide |
| C48 | 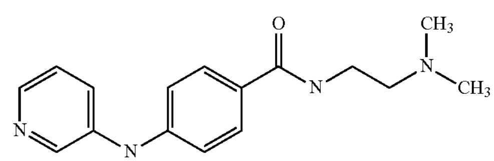 [SMILES: CN(C)CCNC(=O)c1ccc(Nc2cccnc2)cc1] | 284.364 | C16H20N4O | N-(2-Dimethylamino-ethyl)-4-(pyridin-3-ylamino)-benzamide |
| C49 | 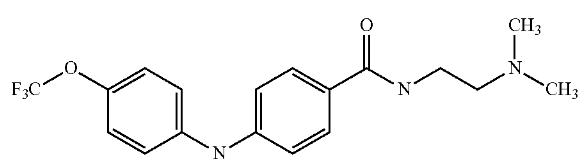 [SMILES: CN(C)CCNC(=O)c1ccc(Nc2ccc(OC(F)(F)F)cc2)cc1] | 367.3742 | C18H20F3N3O2 | N-(2-Dimethylamino-ethyl)-4-(4-trifluoromethoxyphenylamino)-benzamide |

TABLE 1-continued

| Compound | Structure | MW | Structure | Compound |
|---|---|---|---|---|
| C50 | 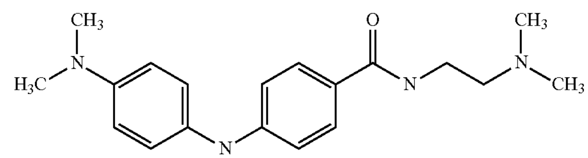 | 326.4453 | C19H25N4O | N-(4-Dimethylamino-ethyl)-4-(4-dimethylaminophenylamino)-benzamide |
| C51 | 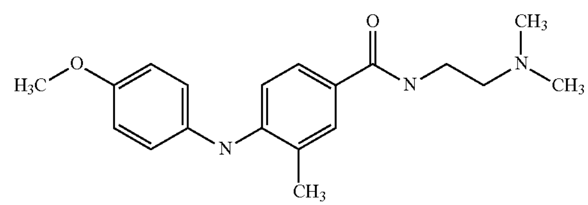 | 327.43 | C19H25N3O2 | N-(2-Dimethylamino-ethyl)-4-(4-methoxy-phenylamino)-3-methyl-benzamide |
| C52 | 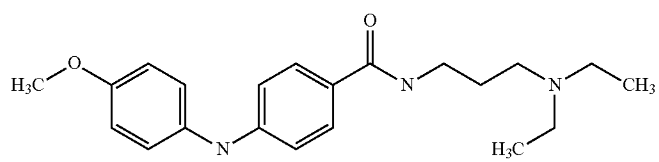 [SMILES: CCN(CC)CCCNC(=O)c1ccc(Nc2ccc(OC)cc2)cc1] | 355.4842 | C21H29N3O2 | N-(3-Diethylamino-propyl)-4-(4-methoxy-phenylamino)-benzamide |
| C53 | 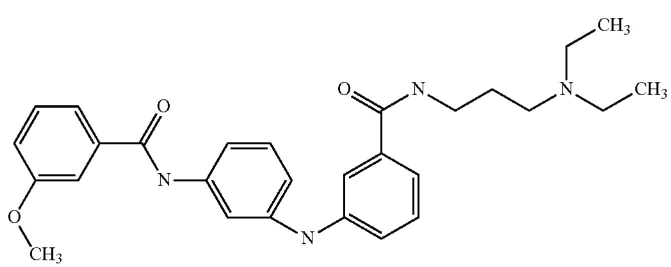 [SMILES: CCN(CC)CCCNC(=O)c1cccc(Nc2cccc(NC(=O)c3cccc(OC)c3)c2)c1] | 474.6082 | C28H34N4O3 | N-(3-Diethylamino-propyl)-3-[3-(3-methoxybenzamideo)-phenylamino]-benzamide |

TABLE 1-continued

| Compound | Structure | MW | Structure | Compound |
|---|---|---|---|---|
| C54 | 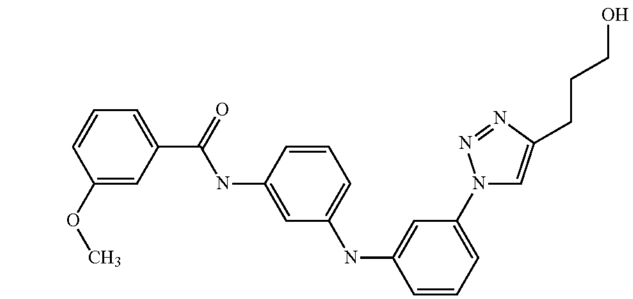 [SMILES: COc1cccc(C(=O)Nc2cccc(Nc3cccc(-n4cc(CCCO)nn4)c3)c2)c1] | 443.5097 | C25H25N5O3 | 3-(1-{3-[3-methoxybenzamido)-phenylamino]-phenyl}-1H-1,2,3-triazol-4-yl)-propan-1-ol |
| C55 | 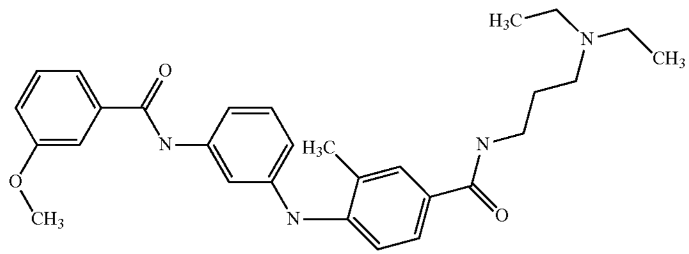 [SMILES: CCN(CC)CCCNC(=O)c1ccc(Nc2cccc(NC(=O)c3cccc(OC)c3)c2)c(C)c1] | 488.6353 | C29H36N4O3 | N-(3-Diethylamino-propyl)-3-methyl-4-[3-(3-methoxybenzamido)-phenylamino]-benzamide |
| C56 | 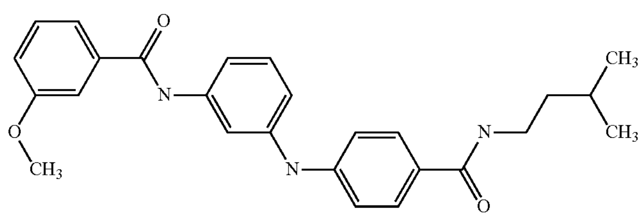 [SMILES: COc1cccc(C(=O)Nc2cccc(Nc3ccc(C(=O)NCCC(C)C)cc3)c2)c1] | 431.5393 | C26H29N3O3 | N-(3-Methyl-butyl)-4-[3-(3-methoxybenzamido)-phenylamino]-benzamide |
| C57 | 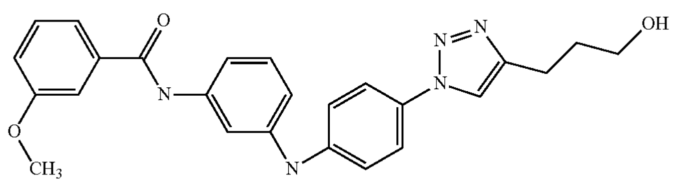 | 443.5097 | C25H25N5O3 | 3-(1-{4-[3-methoxybenzamido)-phenylamino]-phenyl}-1H-1,2,3-triazol-4-yl)-propan-1-ol |

TABLE 1-continued

| Compound | Structure | MW | Structure | Compound |
|---|---|---|---|---|
| C58 | 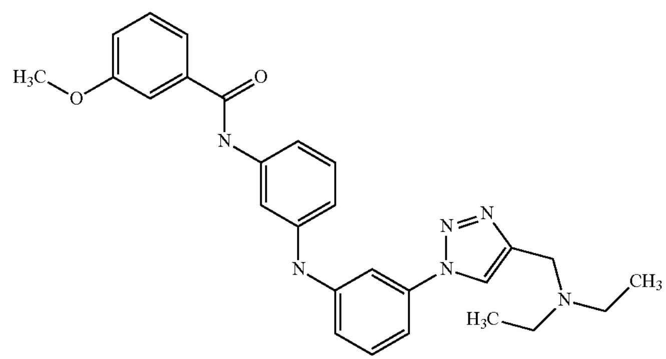 [SMILES: CCN(CC)Cc1cn(-c2cccc(Nc3cccc(NC(=O)c4cccc(OC)c4)c3)c2)nn1] | 479.5797 | C27H30N6O2 | (N-diethylamino)-3-(1-{3-[3-methoxybenzamido)-phenylamino]-phenyl}-1H-1,2,3-triazol-4-yl)-methylamine |
| C59 | 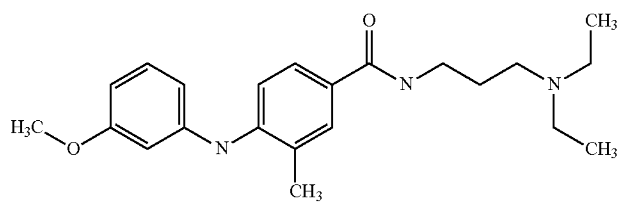 [SMILES: CCN(CC)CCCNC(=O)c1ccc(Nc2cccc(OC)c2)c(C)c1] | 369.5113 | C22H31N3O2 | N-(3-Diethylamino-propyl)-4-(3-methoxy-phenylamino)-3-methyl-benzamide |
| C60 | 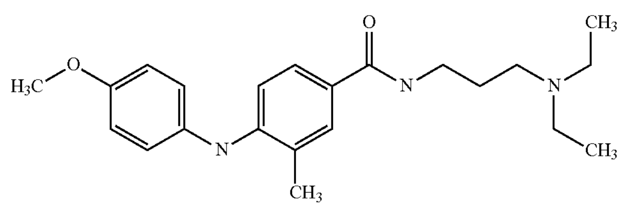 [SMILES: CCN(CC)CCCNC(=O)c1ccc(Nc2ccc(OC)cc2)c(C)c1] | 369.5113 | C22H31N3O2 | N-(3-Diethylamino-propyl)-4-(4-methoxy-phenylamino)-3-methyl-benzamide |
| C61 | 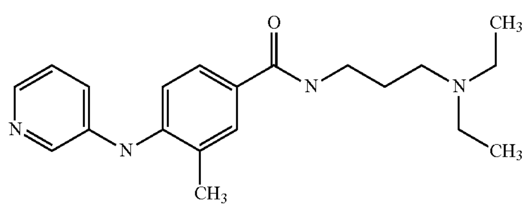 [SMILES: CCN(CC)CCCNC(=O)c1ccc(Nc2cccnc2)c(C)c1] | 340.4724 | C20H28N4O | N-(3-Diethylamino-propyl)-3-methyl-4-(pyridin-3-ylamino)-benzamide |

TABLE 1-continued

| Compound | Structure | MW | Structure | Compound |
|---|---|---|---|---|
| C62 | 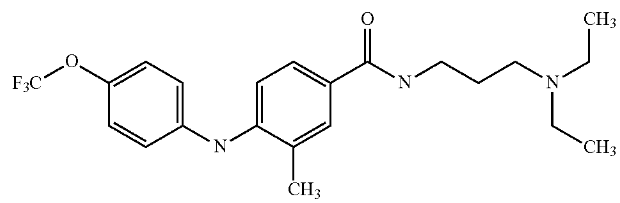 [SMILES: CCN(CC)CCCNC(=O)c1ccc(Nc2ccc(OC(F)(F)F)cc2)c(C)c1] | 423.4826 | C22H28F3N3O2 | N-(3-Diethylamino-propyl)-3-methyl-4-(4-trifluoromethoxyphenylamino)-benzamide |
| C63 | 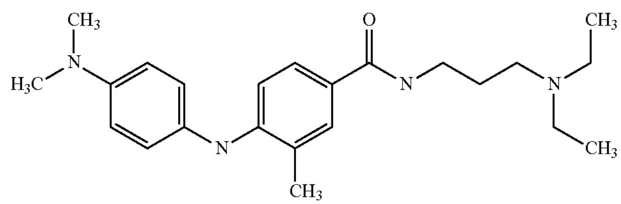 [SMILES: CCN(CC)CCCNC(=O)c1ccc(Nc2ccc(N(C)C)cc2)c(C)c1] | 382.5536 | C23H34N4O | N-(3-Diethylamino-propyl)-4-(4-dimethylaminophenylamino)-3-methylbenzamide |
| C64 | 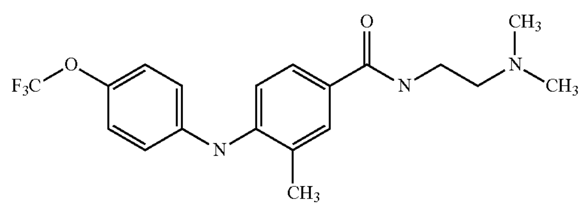 | 381.4013 | C19H22F3N3O2 | N-(2-Dimethylamino-ethyl)-3-methyl-4-(4-trifluoromethoxyphenylamino)-benzamide |
| C65 | 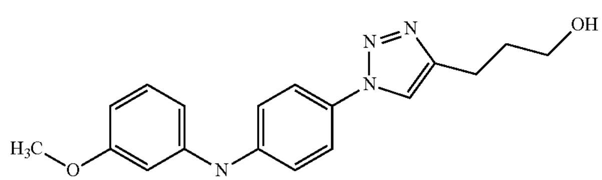 [SMILES: COc1cccc(Nc2ccc(-n3cc(CCCO)nn3)cc2)c1] | 324.3857 | C18H20N4O2 | 3-{1-[4-(3-Methoxyphenylamino)-phenyl]-1H-1,2,3-triazol-4-yl}-propan-1-ol |
| C66 | 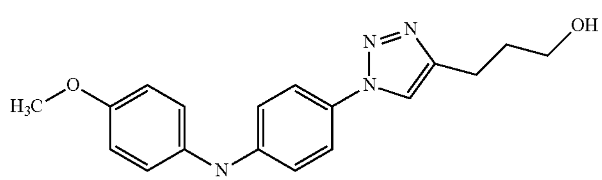 [SMILES: COc1ccc(Nc2ccc(-n3cc(CCCO)nn3)cc2)cc1] | 324.3857 | C18H20N4O2 | 3-{1-[4-(4-Methoxyphenylamino)-phenyl]-1H-1,2,3-triazol-4-yl}-propan-1-ol |

TABLE 1-continued

| Compound | Structure | MW | Structure | Compound |
|---|---|---|---|---|
| C67 | 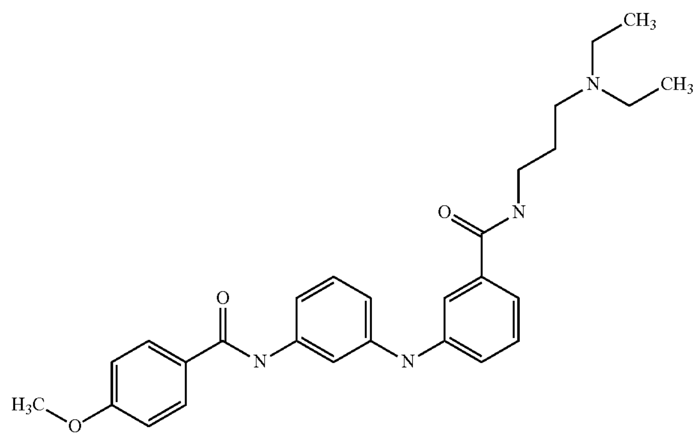 [SMILES: CCN(CC)CCCNC(=O)c1cccc(Nc2cccc(NC(=O)c3ccc(OC)cc3)c2)c1] | 474.6082 | C28H34N4O3 | N-(3-Diethylamino-propyl)-3-[3-(3-methoxybenzamido)-phenylamino]-benzamide |
| C68 | 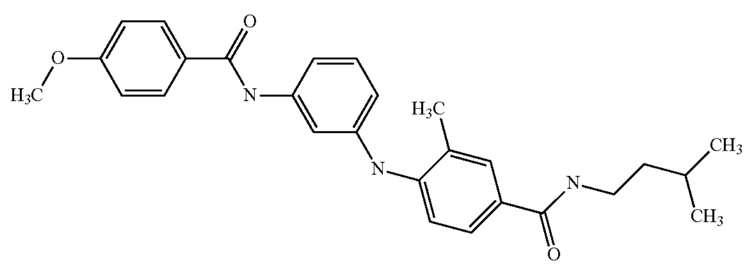 [SMILES: COc1ccc(C(=O)Nc2cccc(Nc3ccc(C(=O)NCCC(C)C)cc3C)c2)cc1] | 445.5664 | C27H31N3O3 | N-(3-Methyl-butyl)-3-methyl-4-[3-(4-methoxybenzamido)-phenylamino]-benzamide |
| C69 | 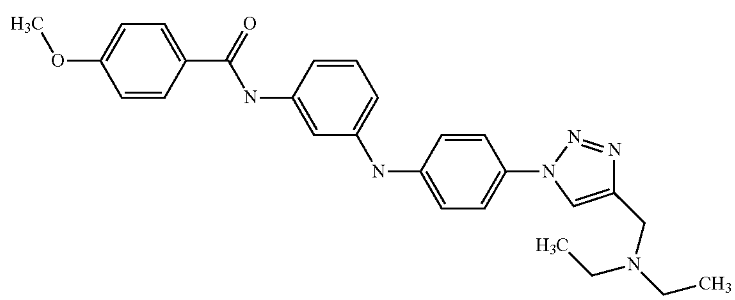 [SMILES: CCN(CC)Cc1cn(-c2ccc(Nc3cccc(NC(=O)c4ccc(OC)cc4)c3)cc2)nn1] | 470.5792 | C27H30N6O2 | (N-Diethylamino)-3-(1-{3-[(4-methoxybenzamido)-phenylamino]-phenyl}-1H-1,2,3-triazol-4-yl)-methylamine |

TABLE 1-continued

| Compound | Structure | MW | Structure | Compound |
|---|---|---|---|---|
| C70 | 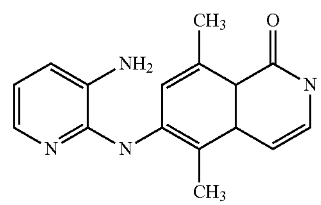 [SMILES: CC1=CC(Nc2ncccc2N)=C(C)C2C=CNC(=O)C12] | 282.3481 | C16H18N4O | 6-(3-Amino-pyridin-2-ylamino)-5,8-dimethyl-4a,8adihydro-2H-isoquinolin-1-one |
| C71 | 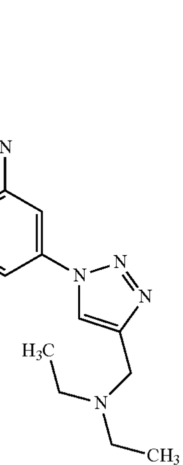 | 351.4552 | C20H25N5O | (N-diethylamino)-{1-[3-(4-Methoxy-phenylamino)-phenyl]-1H-1,2,3-triazol-4-yl}-methylamine |
| C72 | 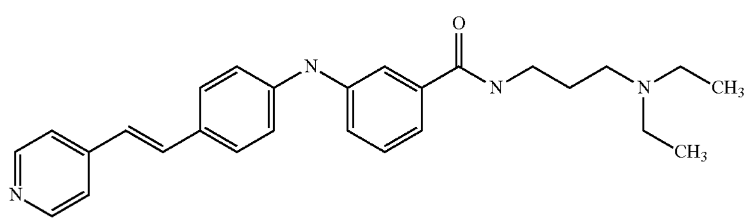 [SMILES: CCN(CC)CCCNC(=O)c1cccc(Nc2ccc(/C=C/c3ccncc3)cc2)c1] | 428.5823 | C27H32N4O | N-(3-Diethylamino-propyl)-3-[4-((E)-2-pyridin-4-yl-vinyl)-phenylamino]-benzamide |

TABLE I-continued

| Compound | Structure | MW | Structure | Compound |
|---|---|---|---|---|
| C73 | 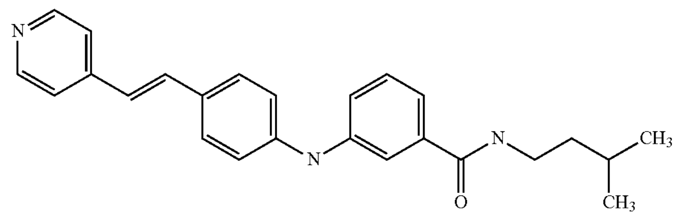 [SMILES: CC(C)CCNC(=O)c1cccc(Nc2ccc(/C=C/c3ccncc3)cc2)c1] | 385.5134 | C25H27N3O | N-(3-Methyl-butyl)-3-[4-((E)-2-pyridin-4-yl-vinyl)-phenylamino]-benzamide |
| C74 | 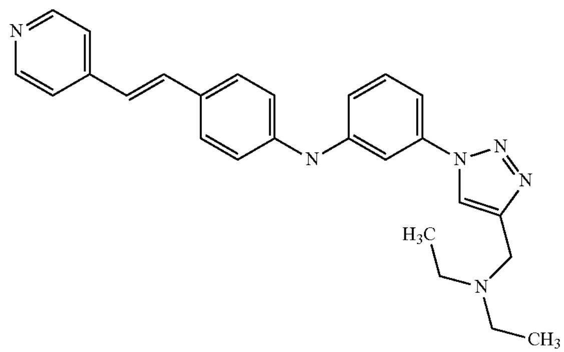 [SMILES: CCN(CC)Cc1cn(-c2cccc(Nc3ccc(/C=C/c4ccncc4)cc3)c2)nn1] | 424.5533 | C26H28N6 | (N-Diethylamino)-3-(1-{3-[4-((E)-2-Pyridin-4-yl-vinyl)-phenylamino]-phenyl}-1H-1,2,3-triazol-4-yl)-methylamine |
| C75 | 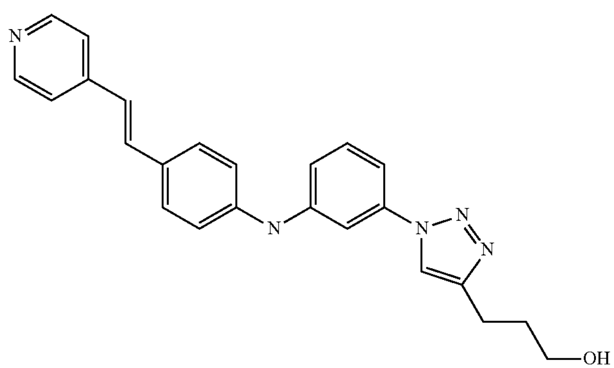 [SMILES: OCCCc1cn(-c2cccc(Nc3ccc(/C=C/c4ccncc4)cc3)c2)nn1] | 397.4838 | C24H23N5O | 3-(1-{3-[4-((E)-2-Pyridin-4-ylvinyl)-phenylamino]-phenyl}-1H-1,2,3-triazol-4-yl)-propan-1-ol |

TABLE 1-continued

| Compound | Structure | MW | Structure | Compound |
|---|---|---|---|---|
| C76 | 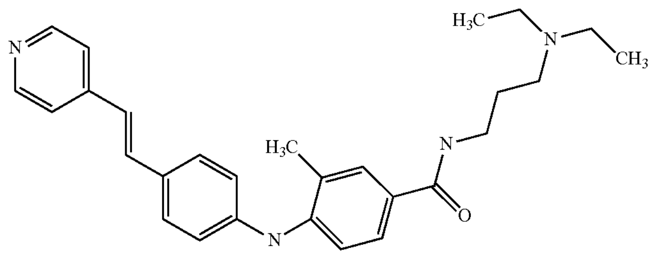 [SMILES: CCN(CC)CCCNC(=O)c1ccc(Nc2ccc(/C=C/c3ccncc3)cc2)c(C)c1] | 442.6094 | C28H34N4O | N-(3-Diethylamino-propyl)-3-methyl-4-[4-((E)-2-pyridin-4-yl-vinyl)-phenylamino]-benzamide |
| C77 | 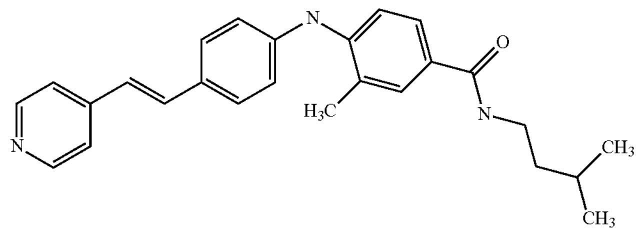 [SMILES: Cc1cc(C(=O)NCCC(C)C)ccc1Nc1ccc(/C=C/c2ccncc2)cc1] | 399.5405 | C26H29N3O | 3-Methyl-N-(3-Methyl-butyl)-4-[4-((E)-2-pyridin-4-yl-vinyl)-phenylamino]-benzamide |
| C78 | 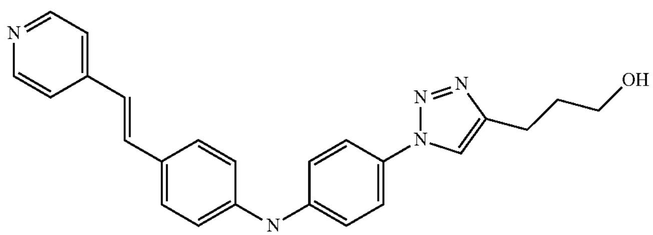 [SMILES: OCCCc1cn(-c2ccc(Nc3ccc(/C=C/c4ccncc4)cc3)cc2)nn1] | 397.4838 | C24H23N5O | 3-(1-{4-[4-((E)-2-Pyridin-ylvinyl)-phenylamino]-phenyl}-1H-1,2,3-triazol-4-yl)-propan-1-ol |
| C79 | 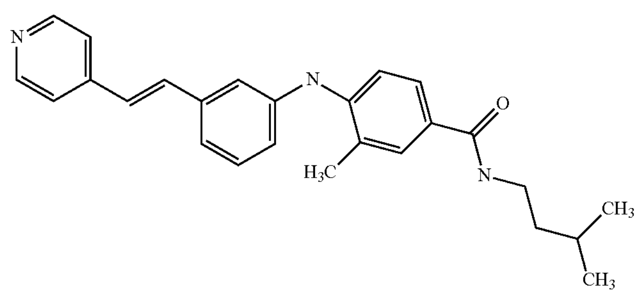 [SMILES: Cc1cc(C(=O)NCCC(C)C)ccc1Nc1cccc(/C=C/c2ccncc2)c1] | 399.5405 | C26H29N3O | 4-Methyl-N-(3-methyl-butyl)-3-[(E)-2-pyridin-4-yl-vinyl)-phenylamino]-benzamide |

TABLE 1-continued

| Compound | Structure | MW | Structure | Compound |
|---|---|---|---|---|
| C80 | 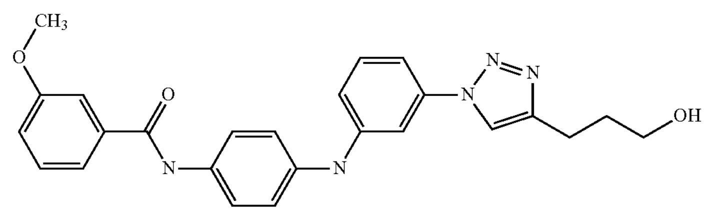 [SMILES: COc1cccc(C(=O)Nc2ccc(Nc3cccc(-n4cc(CCCO)nn4)c3)cc2)c1] | 443.5097 | C25H25N5O3 | 3-(1-{4-[3-methoxybenzamido)-phenylamino]-phenyl}-1H-1,2,3-triazol-4-yl)-propan-1-ol |
| C81 | 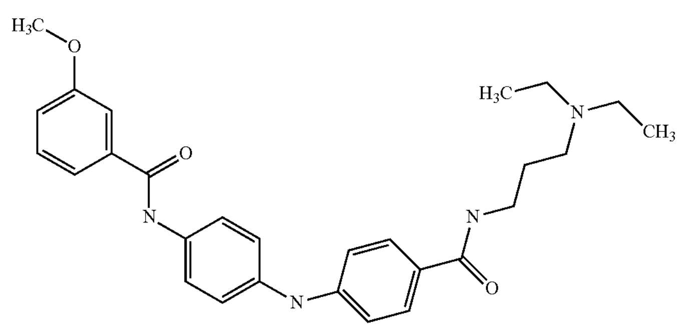 [SMILES: CCN(CC)CCCNC(=O)c1ccc(Nc2ccc(NC(=O)c3cccc(OC)c3)cc2)cc1] | 474.6082 | C28H34N4O3 | N-(3-Diethylamino-propyl)-4-(3-methoxybenzamido)-phenylamino]-benzamide |
| C82 | 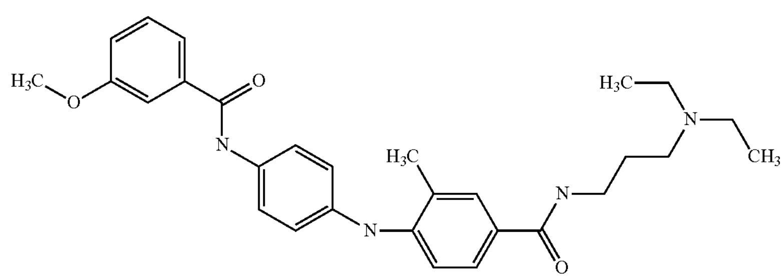 [SMILES: CCN(CC)CCCNC(=O)c1ccc(Nc2ccc(NC(=O)c3cccc(OC)c3)cc2)c(C)c1] | 488.6353 | C29H36N4O3 | N-(3-Diethylamino-propyl)-3-methyl-4-[4-(3-methoxybenzamido)-phenylamino]-benzamide |

TABLE 1-continued

| Compound | Structure | MW | Structure | Compound |
|---|---|---|---|---|
| C83 | 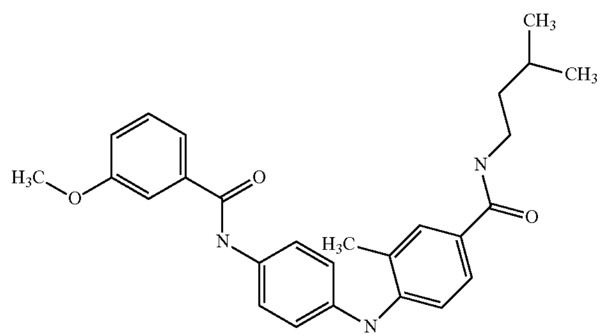 [SMILES: COc1cccc(C(=O)Nc2ccc(Nc3ccc(C(=O)NCCC(C)C)cc3C)cc2)c1] | 445.5664 | C27H31N3O3 | N-(3-methyl-butyl)-3-methyl-4-[4-(3-methoxy-benzamido)-phenylamino]-benzamide |
| C84 | 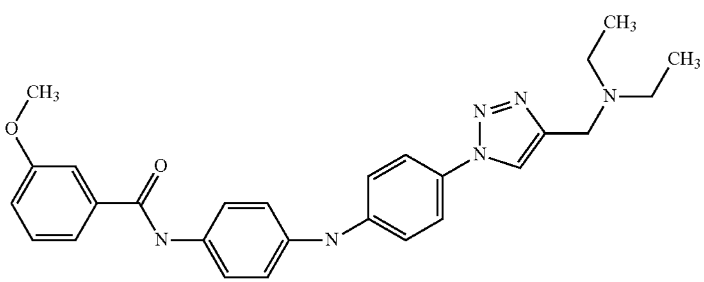 [SMILES: CCN(CC)Cc1cn(-c2ccc(Nc3ccc(NC(=O)c4cccc(OC)c4)cc3)cc2)nn1] | 470.5792 | C27H30N6O2 | (N-Diethylamino)-3-(1-{4-[4-(3-methoxybenzamido)-phenylamino]-phenyl}-1H-1,2,3-triazol-4-yl)-methylamine |
| C85 | 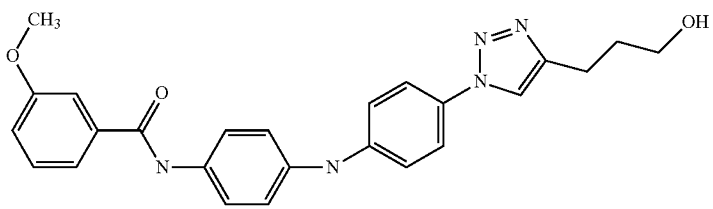 [SMILES: COc1cccc(C(=O)Nc2ccc(Nc3ccc(-n4cc(CCCO)nn4)cc3)cc2)c1] | 443.5097 | C25H25N5O3 | 3-(1-{4-[4-(3-methoxybenzamido)-phenylamino]-phenyl}-1H-1,2,3-triazol-4-yl)-propan-1-ol |

TABLE 1-continued

| Compound | Structure | MW | Structure | Compound |
|---|---|---|---|---|
| C86 | 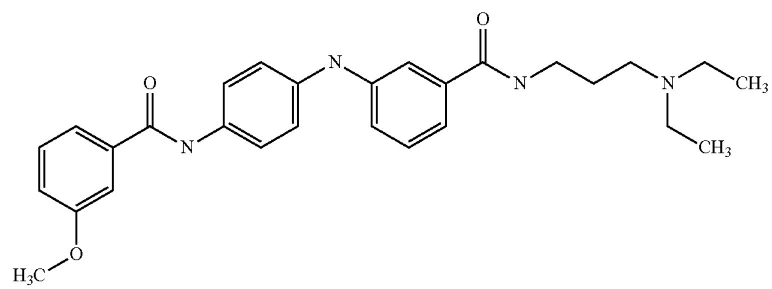 [SMILES: CCN(CC)CCCNC(=O)c1cccc(Nc2ccc(NC(=O)c3cccc(OC)c3)cc2)c1] | 474.6082 | C28H34N4O3 | N-(3-Diethylamino-propyl)-3-[4-(3-methoxybenzamido)-phenyl]-benzamide |
| C87 | 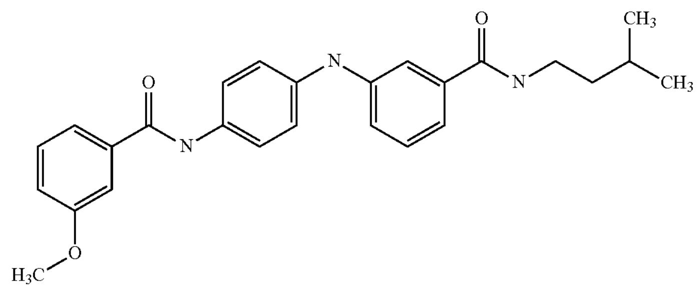 [SMILES: COc1cccc(C(=O)Nc2ccc(Nc3cccc(C(=O)NCCC(C)C)c3)cc2)c1] | 431.5393 | C26H29N3O3 | N-(3-methyl-butyl)-3-[4-(3-methoxybenzamido)-phenylamino]-benzamide |
| C88 | 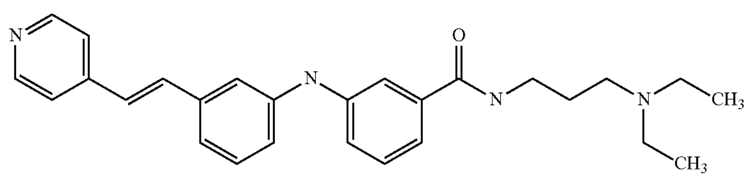 [SMILES: CCN(CC)CCCNC(=O)c1cccc(Nc2cccc(/C=C/c3ccncc3)c2)c1] | 428.5823 | C27H32N4O | N-(3-Diethylamino-propyl)-3-[3-((E)-2-pyridin-4-yl-vinyl)-phenylamino]-benzamide |
| C89 | 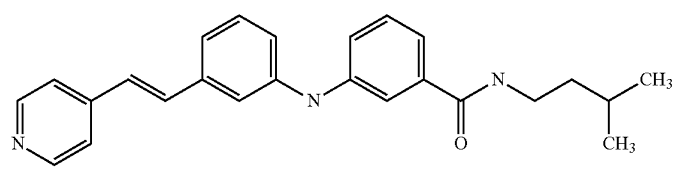 [SMILES: CC(C)CCNC(=O)c1cccc(Nc2cccc(/C=C/c3ccncc3)c2)c1] | 385.5134 | C25H27N3O | N-(3-Methyl-butyl)-3-[3-((E)-2-pyridin-4-yl-vinyl)-phenylamino]-benzamide |

TABLE 1-continued

| Compound | Structure | MW | Structure | Compound |
|---|---|---|---|---|
| C90 | 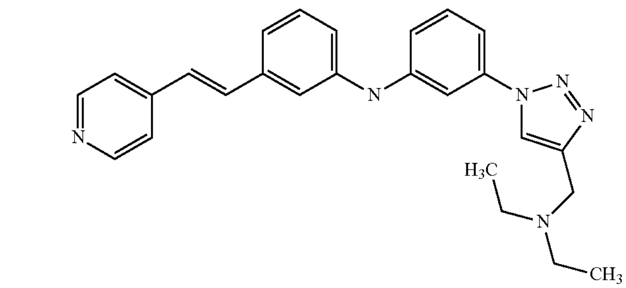 [SMILES: CCN(CC)Cc1cn(-c2cccc(Nc3cccc(/C=C/c4ccncc4)c3)c2)nn1] | 426.5533 | C26H28N6 | (N-diethylamino)-3-(1-{3-[3-((E)-2-Pyridin-4-yl-vinyl)-phenylamino]-phenyl}-1H-1,2,3-triazol-4-yl)-methylamine |
| C91 | 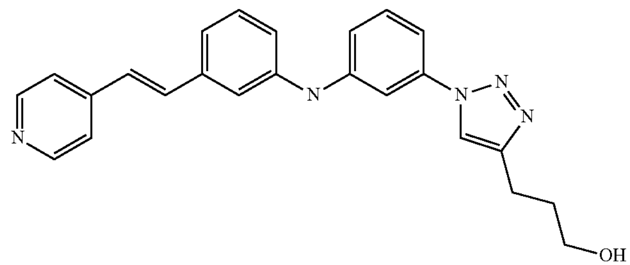 [SMILES: OCCCc1cn(-c2cccc(Nc3cccc(/C=C/c4ccncc4)c3)c2)nn1] | 397.4838 | C24H23N5O | 3-(1-{3-[3-((E)-2-Pyridin-4-ylvinyl)-phenylamino]-phenyl}-1H-1,2,3-triazol-4-yl)-propan-1-ol |
| C92 | 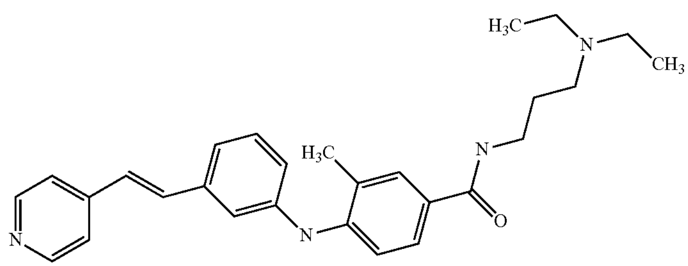 [SMILES: CCN(CC)CCCNC(=O)c1ccc(Nc2cccc(/C=C/c3ccncc3)c2)c(C)c1] | 442.6094 | C28H34N4O | N-(3-Diethylamino-propyl)-3-methyl-4-[3-((E)-2-pyridin-4-yl-vinyl)-phenylamino]-benzamide |
| C93 | 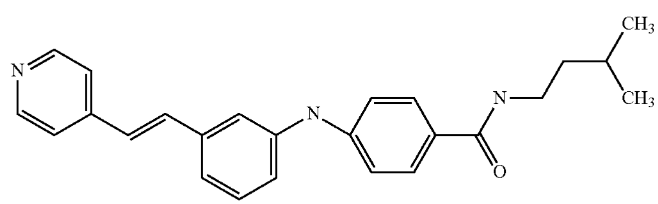 [SMILES: CC(C)CCNC(=O)c1ccc(Nc2cccc(/C=C/c3ccncc3)c2)cc1] | 385.5134 | C25H37N3O | N-(3-Methyl-butyl)-4-[3-((E)-2-pyridin-4-yl-vinyl)-phenylamino]-benzamide |

TABLE 1-continued

| Compound | Structure | MW | Structure | Compound |
|---|---|---|---|---|
| FMB008 | 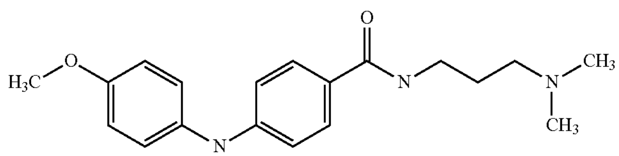 | 327.43 | C19H25N3O2 | N-(3-Dimethylamino-propyl)-4-(4-methoxy-phenylamino)-benzamide Formula V |
| FMB080 | 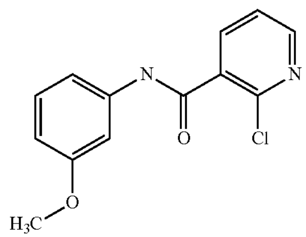 [SMILES: COc1cccc(NC(=O)c2cccnc2Cl)c1] | 262.6978 | C13H11ClN2O2 | 2-Chloro-N-(3-methoxy-phenyl)-nicotinamide Formula III |
| FMB085 | 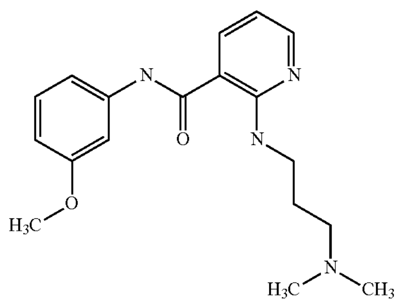 | 328.4176 | C18H24N4O2 | 2-(3-Dimethylamino-propylamino)-N-(3-methoxy-phenyl)-nicotinamide Formula III |
| FMB103 | 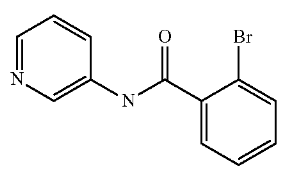 [SMILES: O=C(Nc1cccnc1)c1ccccc1Br] | 277.1223 | C12H9BrN2O | 2-Bromo-N-pyridin-3-yl-benzamide Formula II |

TABLE 1-continued

| Compound | Structure | MW | Structure | Compound |
|---|---|---|---|---|
| FMB104 | 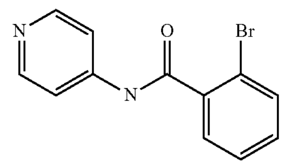 [SMILES: O=C(Nc1ccncc1)c1ccccc1Br] | 277.1223 | C12H9BrN2O | 2-Bromo-N-pyridin-4-yl-benzamide<br>Formula III |
| MB228 | 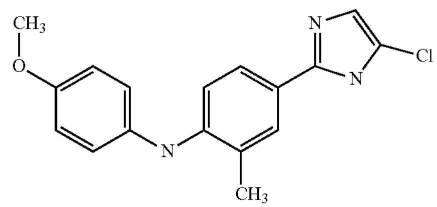 | 313.7896 | C17H16ClN3O | [4-(5-Chloro-1H-imidazol-2-yl)-2-methyl-phenyl]-(4-methoxy-phenyl)-amine<br>Formula IV |
| MB260 | 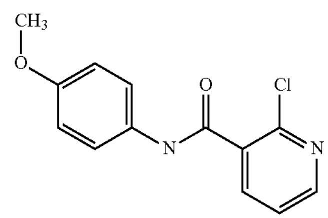 [SMILES: COc1ccc(NC(=O)c2cccnc2Cl)cc1] | 262.6978 | C13H11ClN2O2 | 2-Chloro-N-(4-methoxy-phenyl)-nicotinamide<br>Formula II |
| MB261 | 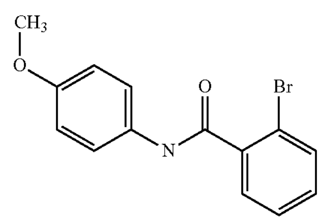 [SMILES: COc1ccc(NC(=O)c2ccccc2Br)cc1] | 306.1612 | C14H12BrNO2 | 2-Bromo-N-(4-methoxy-phenyl)-benzamide<br>Formula II |
| MB262 | 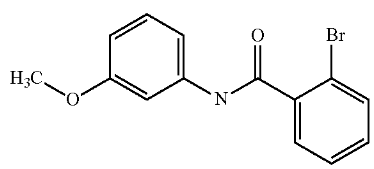 [SMILES: COc1cccc(NC(=O)c2ccccc2Br)c1] | 306.1612 | C14H12BrNO2 | 2-Bromo-N-(3-methoxy-phenyl)-benzamide<br>Formula III |

TABLE 1-continued

| Compound | Structure | MW | Structure | Compound |
|---|---|---|---|---|
| MB265 | 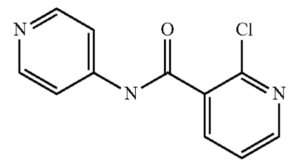 [SMILES: O=C(Nc1ccncc1)c1cccnc1Cl] | 233.6589 | C11H8ClN3O | 2-Chloro-N-pyridin-4-yl-nicotinamide Formula III |
| MB266 | 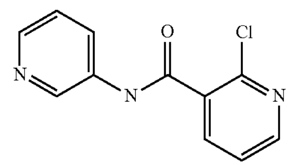 [SMILES: O=C(Nc1cccnc1)c1cccnc1Cl] | 233.6589 | C11H8ClN3O | 2-Chloro-N-pyridin-3-yl-nicotinamide Formula II |
| MB273 | 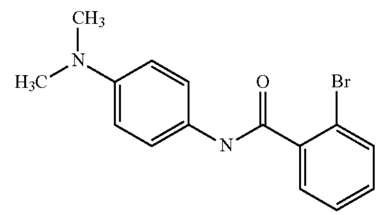 [SMILES: CN(C)c1ccc(NC(=O)c2ccccc2Br)cc1] | 319.2036 | C15H11BrN2O | 2-Bromo-N-(4-dimethylamino-phenyl)-benzamide Formula I |
| MB274 | 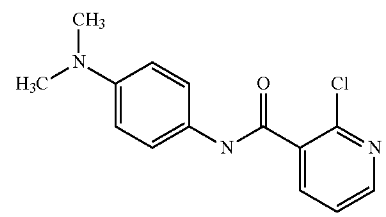 [SMILES: CN(C)c1ccc(NC(=O)c2cccnc2Cl)cc1] | 275.7402 | C14H14ClN3O | 2-Chloro-N-(4-dimethylamino-phenyl)-nicotinamide Formula I |
| FMMB15.1 | 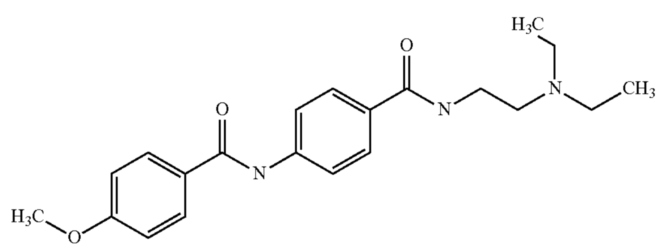 [SMILES: CCN(CC)CCNC(=O)c1ccc(NC(=O)c2ccc(OC)cc2)cc1] | 369.4676 | C21H27N3O3 | Formula I |

TABLE 1-continued

| Compound | Structure | MW | Structure | Compound |
|---|---|---|---|---|
| FMMB15.4 | 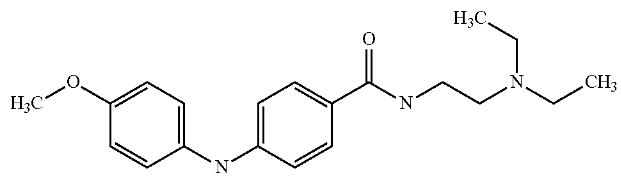 [SMILES: CCN(CC)CCNC(=O)c1ccc(Nc2ccc(OC)cc2)cc1] | 341.4571 | C20H27N3O2 | N-(2-Diethylamino-ethyl)-4-(4-methoxy-phenylamino)-benzamide Formula IV |
| FMMB17.1 | 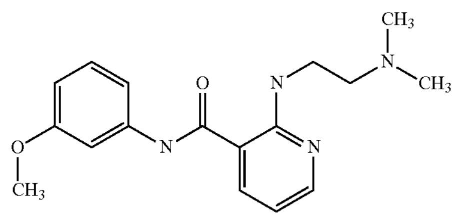 [SMILES: COc1cccc(NC(=O)c2cccnc2NCCN(C)C)c1] | 314.3905 | C17H22N4O2 | 2-(2-Dimethylamino-ethylamino)-N-(3-methoxy-phenyl)-nicotinamide Formula III |
| FMMB17.2 | 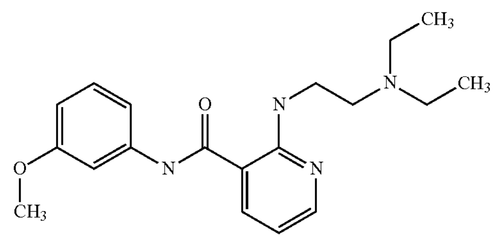 [SMILES: CCN(CC)CCNc1ncccc1C(=O)Nc1cccc(OC)c1] | 342.4447 | C19H26N4O2 | 2-(2-Diethylamino-ethylamino)-N-(3-methoxy-phenyl)-nicotinamide Formula III |
| FMMB17.3 | 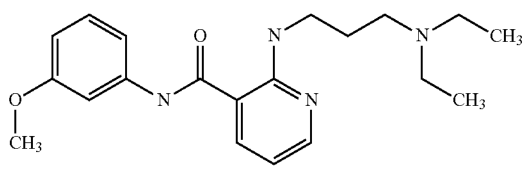 [SMILES: CCN(CC)CCCNc1ncccc1C(=O)Nc1cccc(OC)c1] | 356.4718 | C20H28N4O2 | 2-(3-Diethylamino-propylamino)-N-(3-methoxy-phenyl)-nicotinamide Formula III |
| FMMB17.4 | 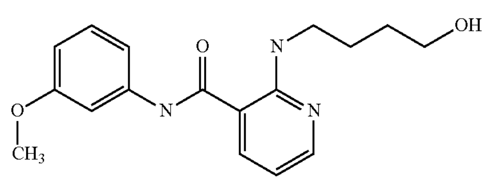 [SMILES: COc1cccc(NC(=O)c2cccnc2NCCCCO)c1] | 315.3752 | C17H21N3O3 | 2-(4-Hydroxy-butylamino)-N-(3-methoxy-phenyl)-nicotinamide Formula III |

TABLE 1-continued

| Compound | Structure | MW | Structure | Compound |
|---|---|---|---|---|
| FMMB17.5 | 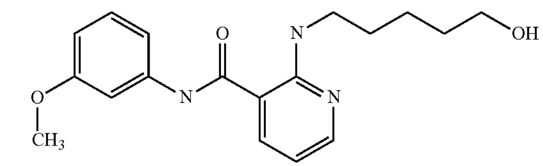 [SMILES: COc1cccc(NC(=O)c2cccnc2NCCCCCO)c1] | 329.4023 | C18H23N3O3 | 2-(5-Hydroxy-pentylamino)-N-(3-methoxy-phenyl)-nicotinamide Formula III |
| FMMB17.6 | 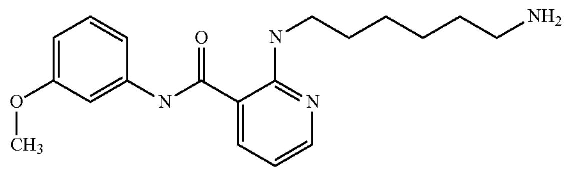 [SMILES: COc1cccc(NC(=O)c2cccnc2NCCCCCCN)c1] | 342.4447 | C19H26N4O2 | 2-(6-Amino-hexylamino)-N-(3-methoxy-phenyl)-nicotinamide Formula III |
| FMMB17.7 | 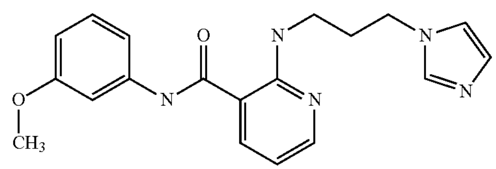 [SMILES: COc1cccc(NC(=O)c2cccnc2NCCCn2ccnc2)c1] | 351.4115 | C19H21N5O2 | 2-(3-Imidazol-1-yl-propylamino)-N-(3-methoxy-phenyl)-nicotinamide Formula III |
| FMMB21.1 | 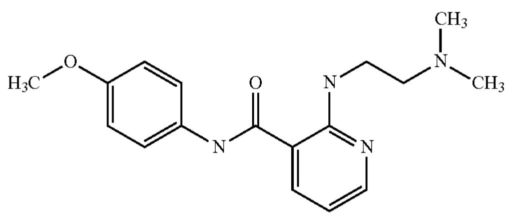 | 314.3905 | C17H22N4O2 | 2-(2-Dimethylamino-ethylamino)-N-(4-methoxy-phenyl)-nicotinamide Formula I |
| FMMB22.1 | 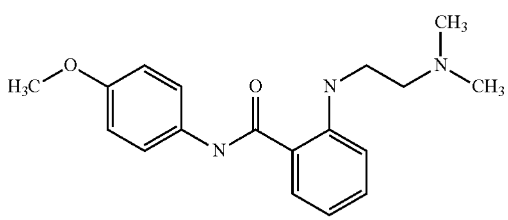 | 313.4029 | C18H23N3O2 | 2-(2-Dimethylamino-ethylamino)-N-(4-methoxy-phenyl)-benzamide Formula I |

TABLE 1-continued

| Compound | Structure | MW | Structure | Compound |
|---|---|---|---|---|
| FMMB22.2 | 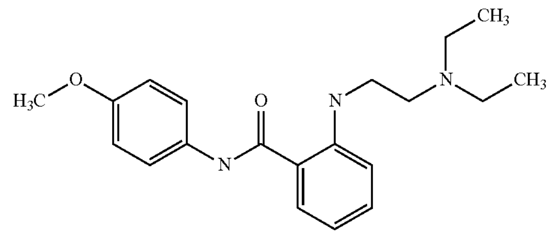 [SMILES: CCN(CC)CCNc1ccccc1C(=O)Nc1ccc(OC)cc1] | 341.4571 | C20H27N3O2 | 2-(3-Diethylamino-ethylamino)-N-(4-methoxy-phenyl)-benzamide Formula I |
| FMMB22.3 | 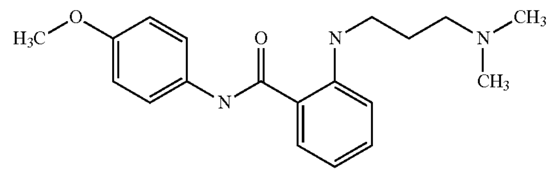 | 327.43 | C19H25N3O2 | 2-(3-Dimethylamino-propylamino)-N-(4-methoxy-phenyl)-benzamide Formula I |
| FMMB22.5 | 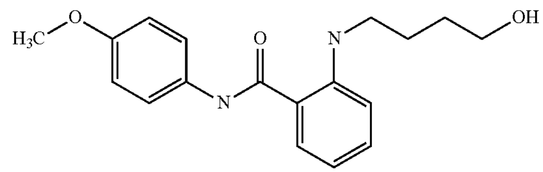 [SMILES: COc1ccc(NC(=O)c2ccccc2NCCCCO)cc1] | 314.3876 | C18H22N2O3 | 2-(4-Hydroxy-butylamino)-N-(4-methoxy-phenyl)-benzamide Formula I |
| FMMB22.7 | 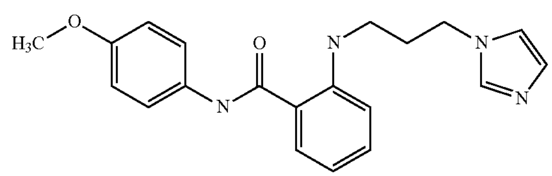 [SMILES: COc1ccc(NC(=O)c2ccccc2NCCCn2ccnc2)cc1] | 350.4239 | C20H22N4O2 | 2-(3-Imidazol-1-yl-propylamino)-N-(4-methoxy-phenyl)-benzamide Formula I |
| FMMB22.9 | 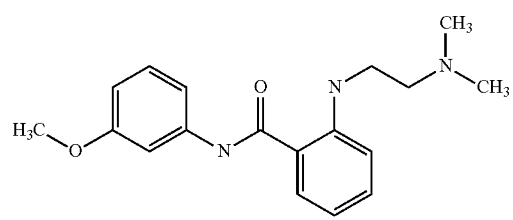 | 313.4029 | C18H23N3O2 | 2-(2-Dimethylamino-ethylamino)-N-(3-methoxy-phenyl)-benzamide Formula III |

TABLE 1-continued

| Compound | Structure | MW | Structure | Compound |
|---|---|---|---|---|
| FMMB22.10 | 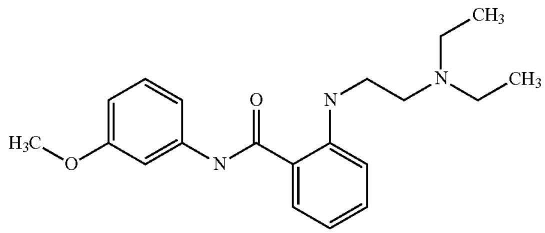 [SMILES: CCN(CC)CCNc1ccccc1C(=O)Nc1cccc(OC)c1] | 341.4571 | C20H27N3O2 | 2-(2-Diethylamino-ethylamino)-N-(3-methoxy-phenyl)-benzamide Formula III |
| FMMB22.11 | 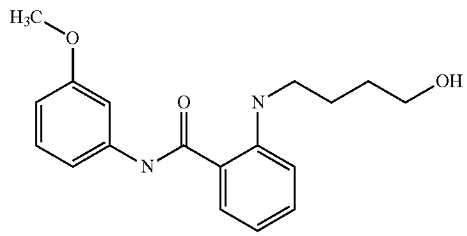 [SMILES: COc1cccc(NC(=O)c2ccccc2NCCCCO)c1] | 314.3876 | C18H22N2O3 | 2-(4-Hydroxy-butylamino)-N-(3-methoxy-phenyl)-benzamide Formula III |
| FMMB22.13 | 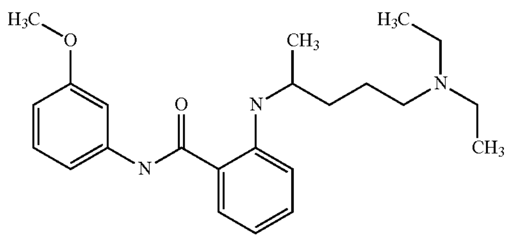 [SMILES: CCN(CC)CCCC(C)Nc1ccccc1C(=O)Nc1cccc(OC)c1] | 383.5384 | C23H33N3O2 | 2-(4-Diethylamino-1-methyl-butylamino)-N-(3-methoxy-phenyl)-benzamide Formula III |
| FMMB22.16 | 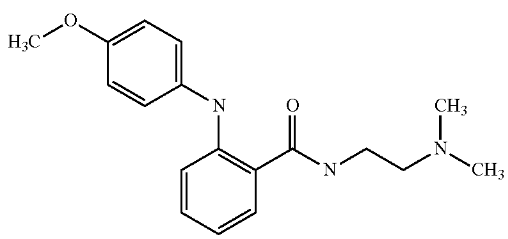 | 313.4029 | C18H23N3O2 | N-(2-Dimethylamino-ethyl)-2-(4-methoxy-phenylamino)-benzamide Formula IV |

TABLE 1-continued

| Compound | Structure | MW | Structure | Compound |
|---|---|---|---|---|
| FMMB23.4 | 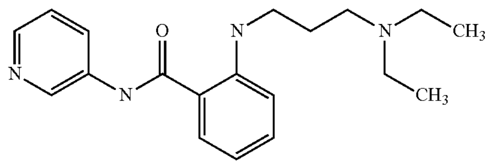 [SMILES: CCN(CC)CCCNc1ccccc1C(=O)Nc1cccnc1] | 326.4453 | C19H26N4O | 2-(3-Diethylamino-propylamino)-N-pyridin-3-yl-benzamide Formula II |
| FMMB23.10 | 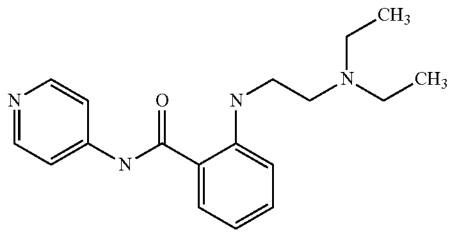 [SMILES: CCN(CC)CCNc1ccccc1C(=O)Nc1ccncc1] | 312.4182 | C18H24N4O | 2-(2-Diethylamino-ethylamino)-N-pyridin-4-yl-benzamide Formula III |
| FMMB23.11 | 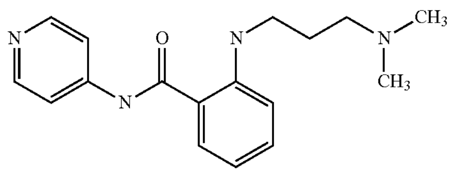 [SMILES: CN(C)CCCNc1ccccc1C(=O)Nc1ccncc1] | 298.3911 | C17H22N4O | 2-(2-Diethylamino-ethylamino)-N-pyridin-4-yl-benzamide Formula III |
| FMMB23.12 | 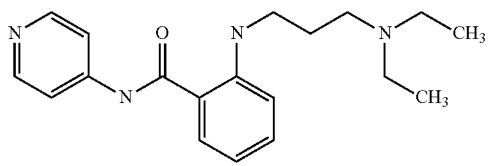 [SMILES: CCN(CC)CCCNc1ccccc1C(=O)Nc1ccncc1] | 326.4453 | C19H26N4O | 2-(3-Diethylamino-propylamino)-N-pyridin-4-yl-benzamide Formula III |
| FMMB23.15 | 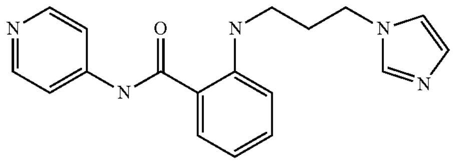 [SMILES: O=C(Nc1ccncc1)c1ccccc1NCCCn1ccnc1] | 321.385 | C18H19N5O | 2-(3-Imidazol-1-yl-propylamino)-N-pyridin-4-yl-benzamide Formula III |

TABLE 1-continued

| Compound | Structure | MW | Structure | Compound |
|---|---|---|---|---|
| FMMB25.3 | 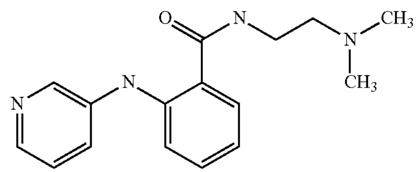 [SMILES: CN(C)CCNC(=O)c1ccccc1Nc1cccnc1] | 284.364 | C16H20N4O | N-(2-Dimethylamino-ethyl)-2-(pyridin-3-ylamino)-benzamide<br>Formula V |
| FMB139 | 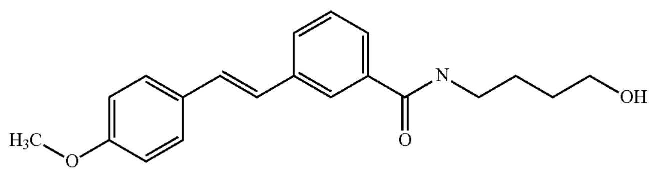 [SMILES: COc1ccc(/C=C/c2cccc(C(=O)NCCCCO)c2)cc1] | 325.4112 | C20H23NO3 | N-(4-Hydroxy-butyl)-3-[2-(4-methoxy-phenyl)-vinyl]-benzamide<br>Formula VII |
| FMMB15.3 | 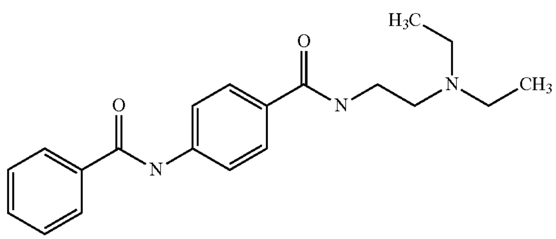 [SMILES: CCN(CC)CCNC(=O)c1ccc(NC(=O)c2ccccc2)cc1] | 339.4412 | C20H25N3O2 | 4-Benzoylamino-N-(2-diethylamino-ethyl)-benzamide<br>Formula I |
| MB317 | 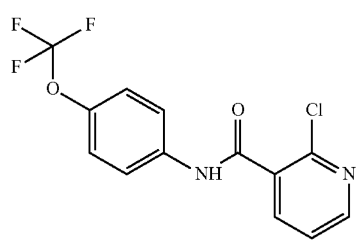 [SMILES: O=C(Nc1ccc(OC(F)(F)F)cc1)c1cccnc1Cl] | 316.6691 | C13H8ClF3N2O2 | 2-Chloro-N-(4-trifluoromethoxy-phenyl)-nicotinamide<br>Formula I |

TABLE 1-continued

| Compound | Structure | MW | Structure | Compound |
|---|---|---|---|---|
| MB318 | 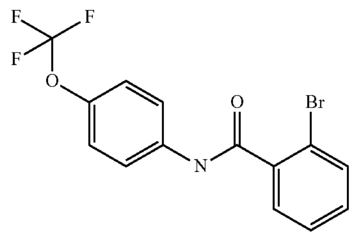 [SMILES: O=C(Nc1ccc(OC(F)(F)F)cc1)c1ccccc1Br] | 360.1325 | C14H9BrF3NO2 | 2-Bromo-N-(4-trifluoromethoxy-phenyl)-benzamide Formula I |
| FMMB31.11 | 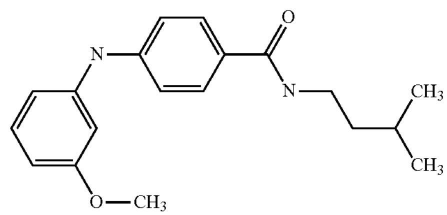 | 312.4153 | C19H24N2O2 | 4-(3-Methoxy-phenylamino)-N-(3-methyl-butyl)-benzamide Formula VI |
| FMMB31.12 | 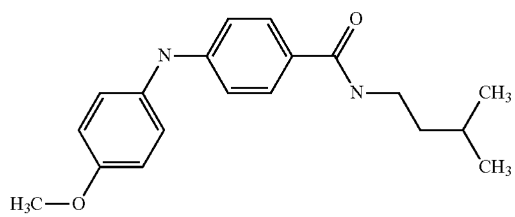 | 312.4153 | C19H24N2O2 | 4-(4-Methoxy-phenylamino)-N-(3-methyl-butyl)-benzamide Formula IV |
| FMMB31.15 | 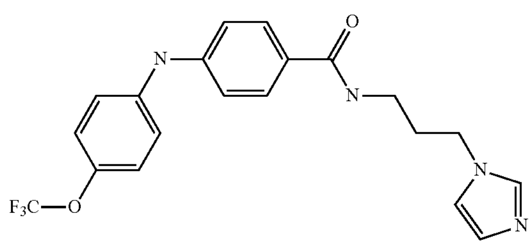 [SMILES: O=C(NCCCn1ccnc1)c1ccc(Nc2ccc(OC(F)(F)F)cc2)cc1] | 404.3952 | C20H19F3N4O2 | N-(3-Imidazol-1-yl-propyl)-4-(4-trifluoromethoxy-phenylamino)-benzamide Formula IV |

TABLE 1-continued

| Compound | Structure | MW | Structure | Compound |
|---|---|---|---|---|
| FMMB32.7 | 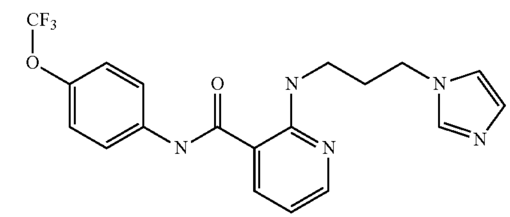 [SMILES: O=C(Nc1ccc(OC(F)(F)F)cc1)c1cccnc1NCCCn1ccnc1] | 405.3828 | C19H18F3N5O2 | 2-(3-Imidazol-1-yl-propylamino)-N-(4-trifluoromethoxy-phenyl)-nicotinamide Formula I |
| FMMB32.10 | 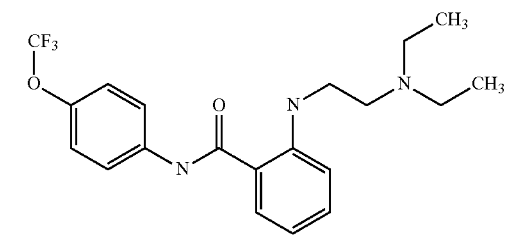 [SMILES: CCN(CC)CCNc1ccccc1C(=O)Nc1ccc(OC(F)(F)F)cc1] | 395.4284 | C20H24F3N3O2 | 2-(2-Diethylamino-ethylamino)-N-(4-trifluoromethoxy-phenyl)-benzamide Formula I |
| FMMB32.11 | 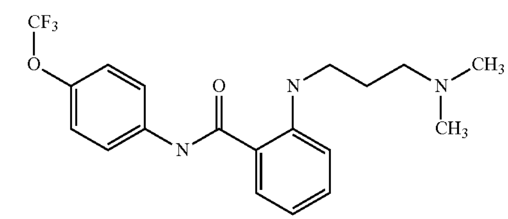 [SMILES: CN(C)CCCNc1ccccc1C(=O)Nc1ccc(OC(F)(F)F)cc1] | 381.4013 | C19H22F3N3O2 | 2-(3-Dimethylamino-propylamino)-N-(4-trifluoromethoxy-phenyl)-benzamide Formula I |
| FMMB32.12 | 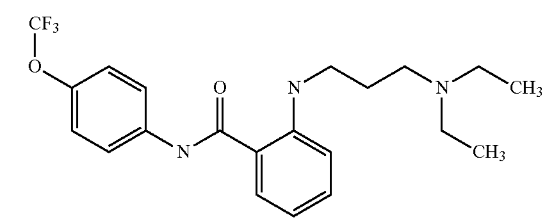 [SMILES: CCN(CC)CCCNc1ccccc1C(=O)Nc1ccc(OC(F)(F)F)cc1] | 409.4555 | C21H26F3N3O2 | 2-(3-Diethylamino-propylamino)-N-(4-trifluoromethoxy-phenyl)-benzamide Formula I |

TABLE 1-continued

| Compound | Structure | MW | Structure | Compound |
|---|---|---|---|---|
| FMMB32.13 | 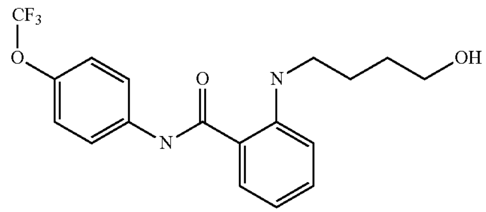 [SMILES: O=C(Nc1ccc(OC(F)(F)F)cc1)c1ccccc1NCCCCO] | 368.3589 | C18H19F3N2O3 | 2-(4-Hydroxy-butylamino)-N-(4-trifluoromethoxy-phenyl)-benzamide Formula I |
| FMMB32.14 | 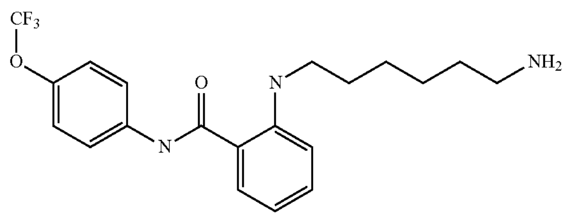 [SMILES: NCCCCCCNc1ccccc1C(=O)Nc1ccc(OC(F)(F)F)cc1] | 395.4284 | C20H24F3N3O2 | 2-(6-Amino-hexylamino)-N-(4-trifluoromethoxy-phenyl)-benzamide Formula I |
| FMMB32.15 | 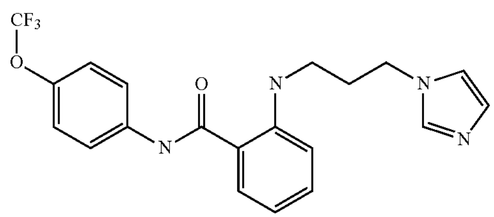 [SMILES: O=C(Nc1ccc(OC(F)(F)F)cc1)c1ccccc1NCCCn1ccnc1] | 404.3952 | C20H19F3N4O2 | 2-(3-Imidazol-1-yl-propylamino)-N-(4-trifluoromethoxy-phenyl)-benzamide Formula I |
| FMMB32.16 | 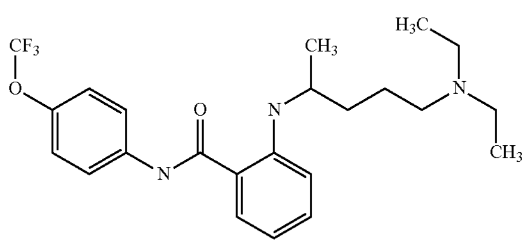 [SMILES: CCN(CC)CCCC(C)Nc1ccccc1C(=O)Nc1ccc(OC(F)(F)F)cc1] | 437.5097 | C23H30F3N3O2 | 2-(4-Diethylamino-1-methyl-butylamino)-N-(4-trifluoromethoxy-phenyl)-benzamide Formula I |

TABLE 1-continued

| Compound | Structure | MW | Structure | Compound |
|---|---|---|---|---|
| FMMB33.2 | 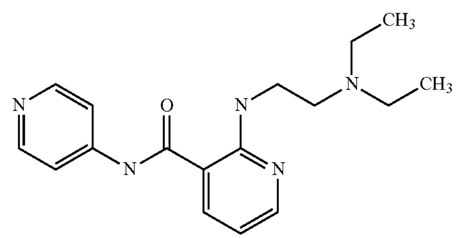 [SMILES: CCN(CC)CCNc1ncccc1C(=O)Nc1ccncc1] | 313.4058 | C17H23N5O | 2-(2-Diethylamino-ethylamino)-N-pyridin-4-yl-nicotinamide Formula III |
| FMMB33.3 | 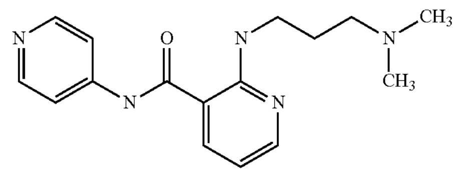 [SMILES: CN(C)CCCNc1ncccc1C(=O)Nc1ccncc1] | 299.3787 | C16H21N5O | 2-(3-Dimethylamino-propylamino)-N-pyridin-4-yl-nicotinamide Formula III |
| FMMB34.1 | 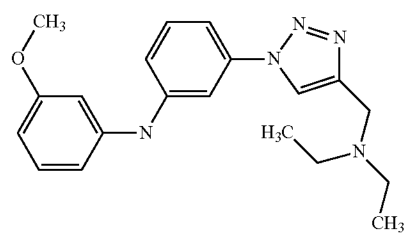 [SMILES: CCN(CC)Cc1cn(-c2cccc(Nc3cccc(OC)c3)c2)nn1] | 351.4552 | C20H25N5O | [3-(4-Diethylaminomethyl-[1,2,3]triazol-1-yl)-phenyl]-(3-methoxy)-phenylamine Formula VI |
| FMMB34.10 | 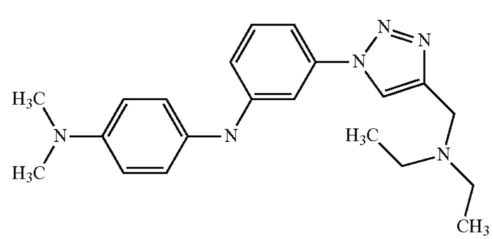 [SMILES: CCN(CC)Cc1cn(-c2cccc(Nc3ccc(N(C)C)cc3)c2)nn1] | 364.4975 | C21H28N6 | [3-(4-Diethylaminomethyl-[1,2,3]triazol-1-yl)-phenyl]-(4-dimethylamino)-phenylamine Formula IV |

TABLE 1-continued

| Compound | Structure | MW | Structure | Compound |
|---|---|---|---|---|
| FMMB25.6 | 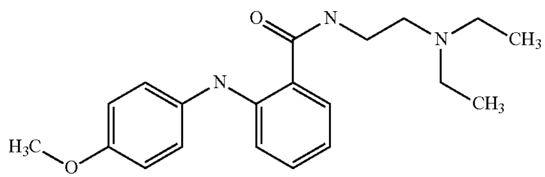 [SMILES: CCN(CC)CCNC(=O)c1ccccc1Nc1ccc(OC)cc1] | 341.4571 | C20H27N3O2 | N-(2-Diethylamino-ethyl)-2-(4-methoxy-phenylamino)-benzamide Formula IV |
| FMMB25.15 | 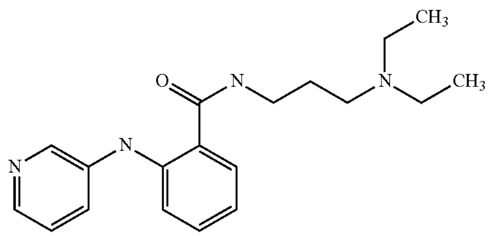 [SMILES: CCN(CC)CCCNC(=O)c1ccccc1Nc1cccnc1] | 326.4453 | C19H26N4O | N-(3-Diethylamino-propyl)-2-(pyridin-3-ylamino)-benzamide Formula V |
| FMMB39.15 | 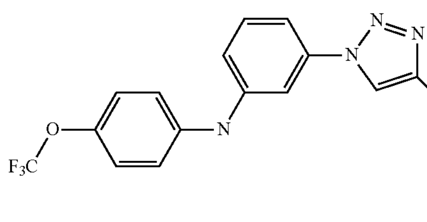 | 378.357 | C18H17F3N4O2 | 3-{1-[3-(4-Trifluoromethoxy-phenylamino)-phenyl]-1H-[1,2,3]triazol-4-yl}-propan-1-ol Formula IV |
| FMMB39.16 | 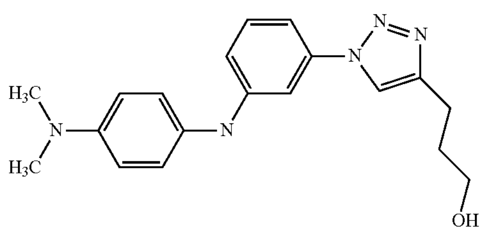 [SMILES: CN(C)c1ccc(Nc2cccc(-n3cc(CCCO)nn3)c2)cc1] | 337.4281 | C19H23N5O | 3-{1-[3-(4-Dimethylamino-phenylamino)-phenyl]-1H-[1,2,3]triazol-4-yl}-propan-1-ol Formula IV |

TABLE 1-continued

| Compound | Structure | MW | Structure | Compound |
|---|---|---|---|---|
| FMMB41.2 | (structure shown) | 431.5393 | C26H29N3O3 | N-(3-Methyl-butyl)-3-[3-(4-methoxy-benzoylamino)-phenylamino]-benzamide Formula I |
| FMMB41.3 | (structure shown) | 470.5792 | C27H30N6O2 | N-{3-[3-(4-Diethylaminomethyl-[1,2,3]triazol-1-yl)-phenylamino]-phenyl}-4-methoxy-benzamide Formula I |

TABLE 1-continued

| Compound | Structure | MW | Structure | Compound |
|---|---|---|---|---|
| FMMB41.4 | 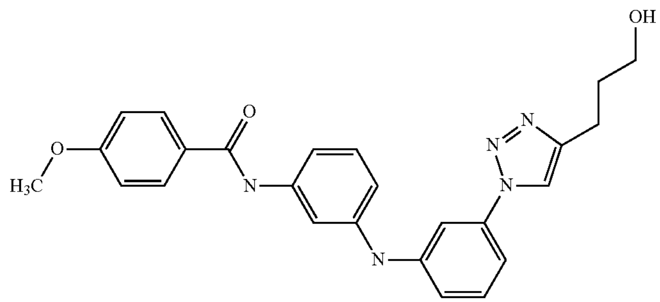 [SMILES: COc1ccc(C(=O)Nc2cccc(Nc3cccc(-n4cc(CCCO)nn4)c3)c2)cc1] | 443.5097 | C25H25N5O3 | N-(3-{4-[4-(3-Hydroxy-propyl)-[1,2,3]triazol-1-yl]-phenylamino}-phenyl)-4-methoxy-benzamide Formula I |
| FMMB41.8 | 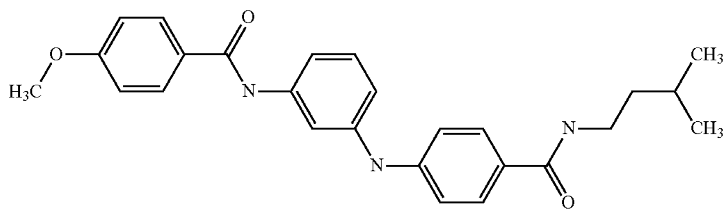 [SMILES: COc1ccc(C(=O)Nc2cccc(Nc3ccc(C(=O)NCCC(C)C)cc3)c2)cc1] | 431.5393 | C26H29N3O3 | N-(3-Methyl-butyl)-4-[3-(4-methoxybenzamido)-phenylamino]-benzamide Formula I |
| FMMB44.1 | 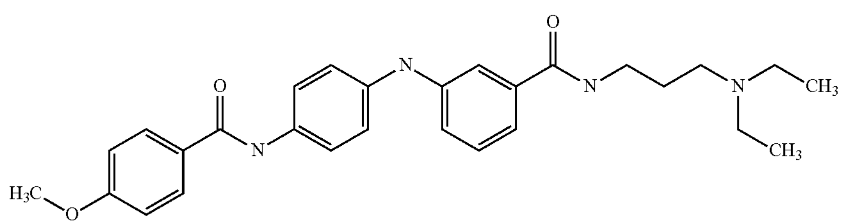 [SMILES: CCN(CC)CCCNC(=O)c1cccc(Nc2ccc(NC(=O)c3ccc(OC)cc3)cc2)c1] | 474.6082 | C28H34N4O3 | N-(3-Diethylamino-propyl)-3-[4-(4-methoxy-benzoylamino)-phenylamino]-3-methyl-benzamide Formula VI |

TABLE 1-continued

| Compound | MW | Structure | Compound |
|---|---|---|---|
| FMMB44.2 | 431.5393 | C26H29N3O3 | N-(3-Methyl-butyl)-3-[4-(4-methoxy-benzoylamino)-phenylamino]-benzamide Formula VI |
| FMMB44.3 | 470.5792 | C27H30N6O2 | (N-Diethylamino)-3-(1-{4-[4-(4-methoxybenzamido)-phenylamino]-phenyl}-1H-1,2,3-triazol-4-yl)-methylamine Formula VI |

TABLE 1-continued

| Compound | MW | Structure | Compound |
|---|---|---|---|
| FMMB44.4 | 443.5097 | C25H25N5O3 | 3-(1-{4-[(4-methoxybenzamido)-phenylamino]-phenyl}-1H-1,2,3-triazol-4-yl)-propan-1-ol<br>Formula VI |
| FMMB44.6 | 488.6353 | C29H36N4O3 | N-(3-Diethylamino-propyl)-4-[4-(4-methoxy-benzoylamino)-phenylamino]-3-methyl-benzamide<br>Formula VI |
| FMMB44.8 | 431.5393 | C26H29N3O3 | N-(3-Methyl-butyl)-4-[4-(4-methoxy-benzoylamino)-phenylamino]-benzamide<br>Formula VI |

TABLE 1-continued

| Compound | Structure | MW | Structure | Compound |
|---|---|---|---|---|
| FMMB55.1 | 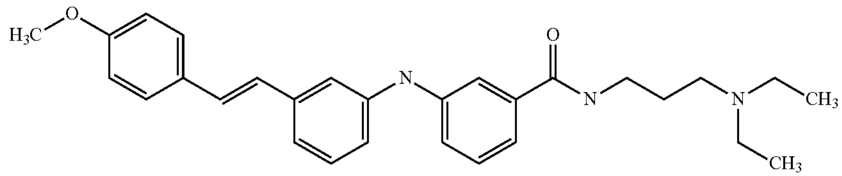 [SMILES: CCN(CC)CCCNC(=O)c1cccc(Nc2cccc(/C=C/c3ccc(OC)cc3)c2)c1] | 457.6212 | C29H35N3O2 | N-(3-Diethylaminol-propyl)-3-[3-((E)-(4-methoxy-styryl)-phenylamino]-benzamide Formula IX |
| FMMB55.2 | 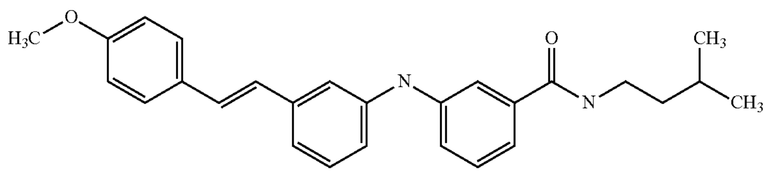 [SMILES: COc1ccc(/C=C/c2cccc(Nc3cccc(C(=O)NCCC(C)C)c3)c2)cc1] | 414.5524 | C27H30N2O2 | N-(3-Methyl-butyl)-3-[3-((E)-(4-methoxy-styryl)-phenylamino]-benzamide Formula IX |
| FMMB55.6 | 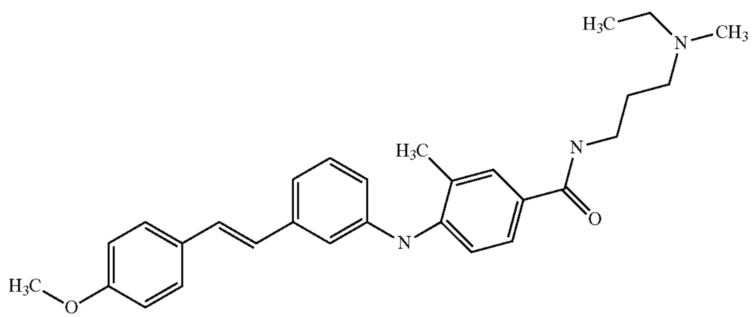 | 417.6483 | C30H37N3O2 | N-(3-Diethylaminol-propyl)-3-methyl-4-[3-((E)-(4-methoxy-styryl)-phenylamino]-benzamide Formula IX |
| FMMB55.7 | 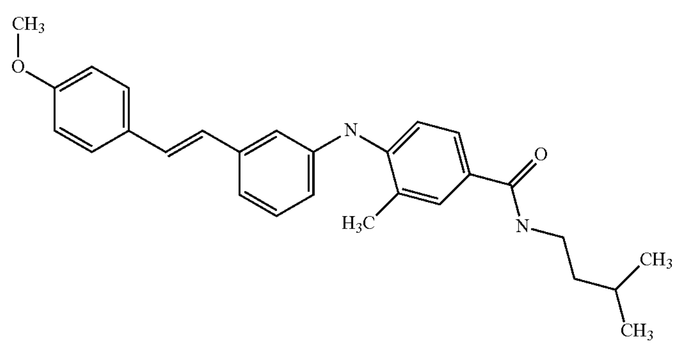 [SMILES: COc1ccc(/C=C/c2cccc(Nc3ccc(C(=O)NCCC(C)C)cc3C)c2)cc1] | 428.5794 | C28H32N2O2 | N-(3-Methyl-butyl)-3-methyl-4-[3-((E)-(4-methoxy-styryl)-phenylamino]-benzamide Formula IX |

TABLE 1-continued

| Compound | Structure | MW | Structure | Compound |
|---|---|---|---|---|
| FMMB55.8 | 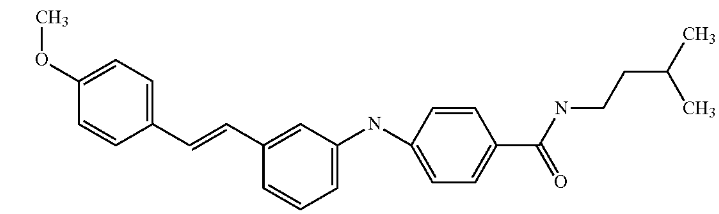 [SMILES: COc1ccc(/C=C/c2cccc(Nc3ccc(C(=O)NCCC(C)C)cc3)c2)cc1] | 414.5524 | C27H30N2O2 | N-(3-Methyl-butyl)-4-[3-((E)-(4-methoxy-styryl)-phenylamino]-benzamide<br>Formula IX |
| FMMB57.1 | 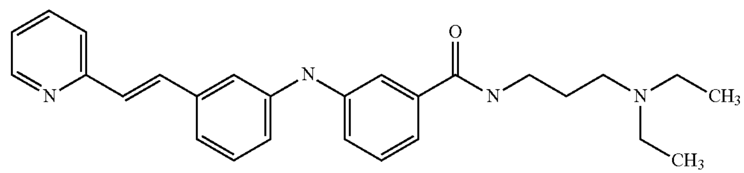 [SMILES: CCN(CC)CCCNC(=O)c1cccc(Nc2cccc(/C=C/c3ccccn3)c2)c1] | 428.5823 | C27H32N4O | N-(3-Diethylamino-propyl)-3-[3-((E)-2-pyridin-2-yl-vinyl)-phenylamino]-benzamide<br>Formula IX |
| FMMB57.2 | 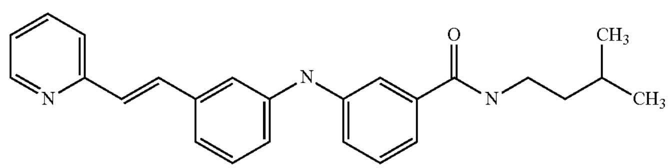 [SMILES: CC(C)CCNC(=O)c1cccc(Nc2cccc(/C=C/c3ccccn3)c2)c1] | 385.5134 | C25H27N3O | N-(3-Methyl-butyl)-3-[3-((E)-2-pyridin-2-yl-vinyl)-phenylamino]-benzamide<br>Formula IX |
| FMMB57.4 | 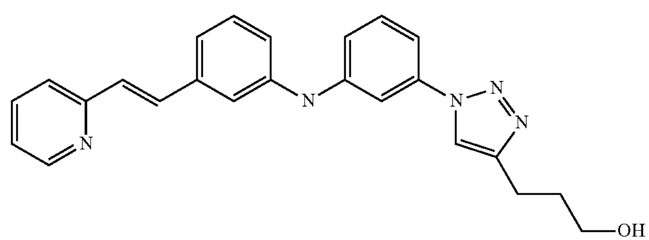 [SMILES: OCCCc1cn(-c2cccc(Nc3cccc(/C=C/c4ccccn4)c3)c2)nn1] | 397.4838 | C24H23N5O | 3-(1-{3-[4-((E)-2-Pyridin-4-ylvinyl)-phenylamino]-phenyl}-1H-1,2,3-triazol-4-yl)-propan-1-ol<br>Formula IX |

TABLE 1-continued

| Compound | Structure | MW | Structure | Compound |
|---|---|---|---|---|
| FMMB57.5 | 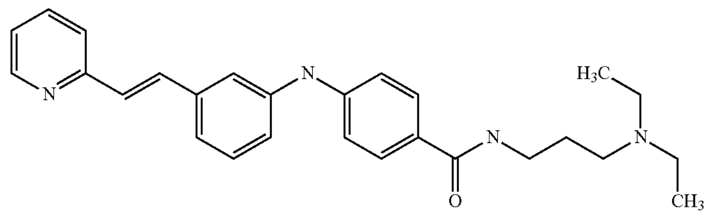 [SMILES: CCN(CC)CCCNC(=O)c1ccc(Nc2cccc(/C=C/c3ccccn3)c2)cc1] | 428.5823 | C27H32N4O | N-(3-Diethylamino-propyl)-4-[3-((E)-2-pyridin-2-yl-vinyl)-phenylamino]-benzamide Formula IX |
| FMMB57.7 | 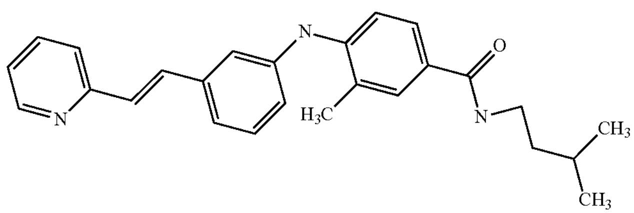 [SMILES: Cc1cc(C(=O)NCCC(C)C)ccc1Nc1cccc(/C=C/c2ccccn2)c1] | 399.5405 | C26H29N3O | N-(3-Methyl-butyl)-3-methyl-4-[3-((E)-2-pyridin-2-yl-vinyl)-phenylamino]-benzamide Formula IX |
| FMMB57.10 | 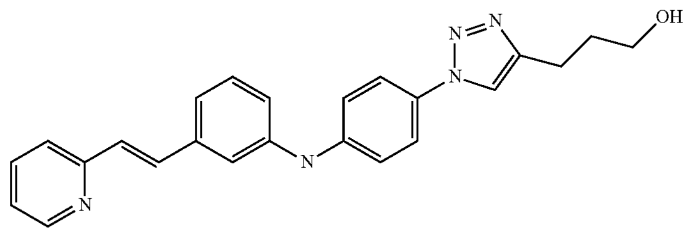 [SMILES: OCCCc1cn(-c2ccc(Nc3cccc(/C=C/c4ccccn4)c3)cc2)nn1] | 397.4838 | C24H23N5O | 3-(1-{3-[(E)-2-Pyridin-2-ylvinyl)-phenylamino]-phenyl}-1H-1,2,3-triaozl-4-yl)-propan-1-ol Formula IX |
| FMMB53.1 | 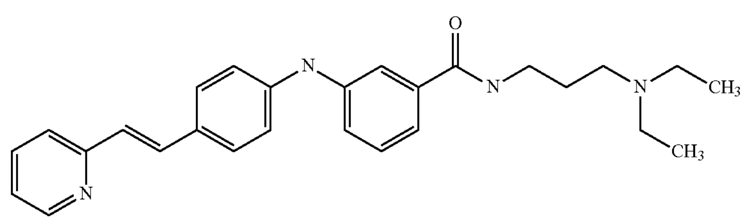 [SMILES: CCN(CC)CCCNC(=O)c1cccc(Nc2ccc(/C=C/c3ccccn3)cc2)c1] | 428.5823 | C27H32N4O | N-(3-Diethylamino-propyl)-3-[4-((E)-2-pyridin-2-yl-vinyl)-phenylamino]-benzamide Formula VII |

TABLE 1-continued

| Compound | Structure | MW | Structure | Compound |
|---|---|---|---|---|
| FMMB53.2 | 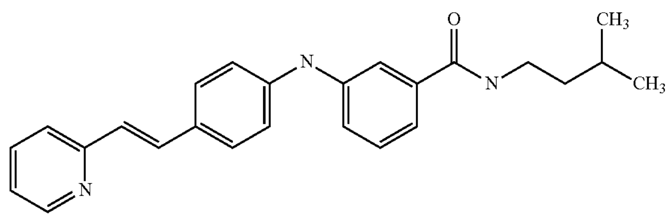 [SMILES: CC(C)CCNC(=O)c1cccc(Nc2ccc(/C=C/c3ccccn3)cc2)c1] | 385.5134 | C25H27N3O | N-(3-Methyl-butyl)-3-[4-((E)-2-pyridin-2-yl-vinyl)-phenylamino]-benzamide Formula VII |
| FMMB53.5 | 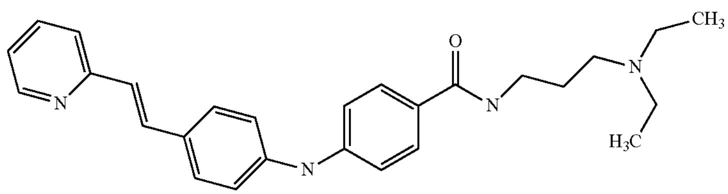 [SMILES: CCN(CC)CCCNC(=O)c1ccc(Nc2ccc(/C=C/c3ccccn3)cc2)cc1] | 428.5823 | C27H32N4O | N-(3-Diethylamino-propyl)-4-[4-((E)-2-pyridin-2-yl-vinyl)-phenylamino]-benzamide Formula VII |
| FMMB53.8 | 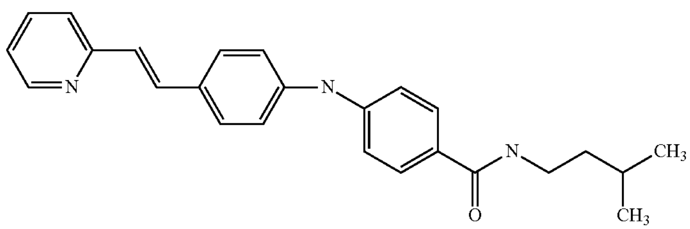 [SMILES: CC(C)CCNC(=O)c1ccc(Nc2ccc(/C=C/c3ccccn3)cc2)cc1] | 385.5134 | C25H27N3O | N-(3-Methyl-butyl)-4-[4-((E)-2-pyridin-2-yl-vinyl)-phenylamino]-benzamide Formula VII |
| FMMB53.10 | 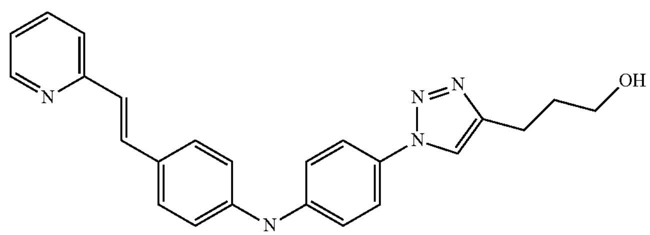 [SMILES: OCCCc1cn(-c2ccc(Nc3ccc(/C=C/c4ccccn4)cc3)cc2)nn1] | 397.4838 | C24H23N5O | 3-(1-{3-[4-((E)-2-Pyridin-2-ylvinyl)-phenylamino]phenyl}-1H-1,2,3-triazol-4-yl)-propan-1-ol Formula VII |

TABLE 1-continued

| Compound | Structure | MW | Structure | Compound |
|---|---|---|---|---|
| FMMB59.2 | 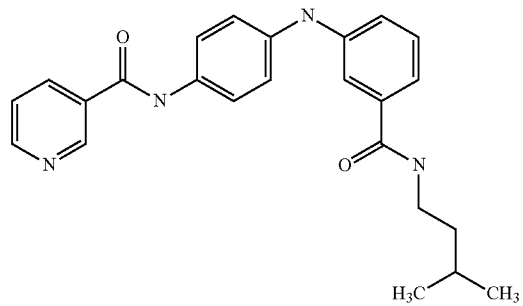 [SMILES: CC(C)CCNC(=O)c1cccc(Nc2ccc(NC(=O)c3cccnc3)cc2)c1] | 402.5004 | C24H26N4O2 | N-{4-[3-(3-Methyl-butylcarbamoyl)-phenylamino]-phenyl}-nicotinamide Formula VI |
| FMMB59.10 | 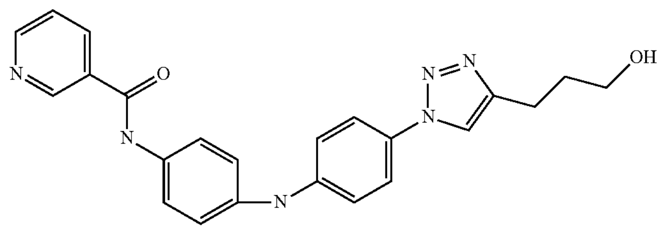 [SMILES: O=C(Nc1ccc(Nc2ccc(-n3cc(CCCO)nn3)cc2)cc1)c1cccnc1] | 414.4708 | C23H22N6O2 | N-{3-[3-(3-Diethylamino-propylcarbamoyl)-phenylamino]-phenyl}-nicotinamide Formula V |
| FMMB46.1 | 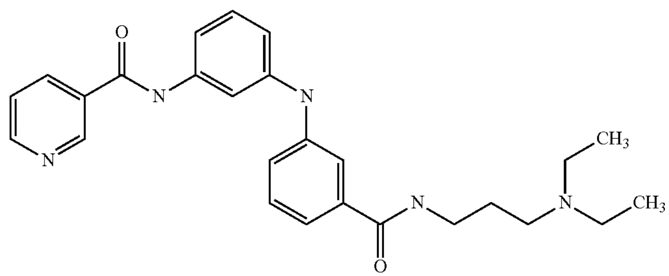 [SMILES: CCN(CC)CCCNC(=O)c1cccc(Nc2cccc(NC(=O)c3cccnc3)c2)c1] | 445.5693 | C26H31N5O2 | N-(3-Diethylamino-propyl)-3-[3-(pyridoyl)-phenylamino]-benzamide Formula V |

TABLE 1-continued

| Compound | Structure | MW | Structure | Compound |
|---|---|---|---|---|
| FMMB46.2 | 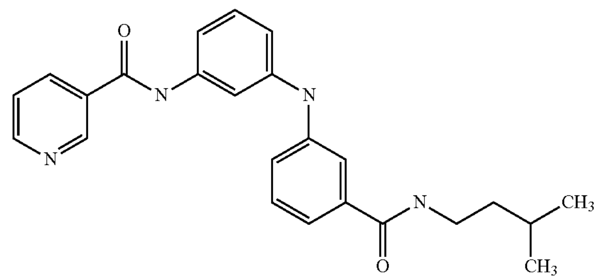 [SMILES: CC(C)CCNC(=O)c1cccc(Nc2cccc(NC(=O)c3cccnc3)c2)c1] | 402.5004 | C24H26N4O2 | N-{3-[3-(3-Methyl-butylcarbamoyl)-phenylamino]-phenyl}-nicotinamide Formula V |
| FMMB46.3 | 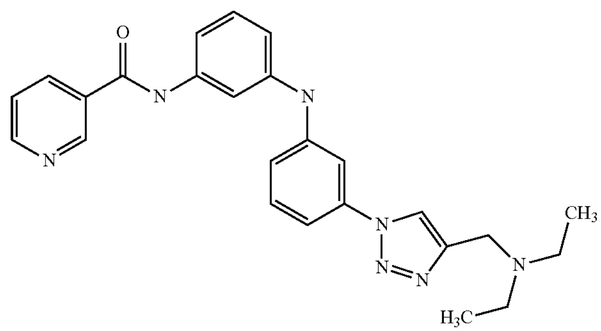 [SMILES: CCN(CC)Cc1cn(-c2cccc(Nc3cccc(NC(=O)c4cccnc4)c3)c2)nn1] | 441.5402 | C25H27N7O | N-{3-[3-(4-Diethylaminomethyl-[1,2,3]triazol-1-yl)-phenylamino]-phenyl}-nicotinamide Formula V |
| FMMB46.5 | 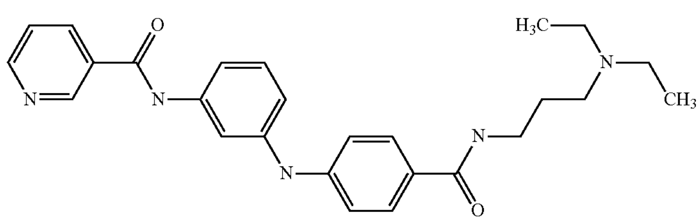 [SMILES: CCN(CC)CCCNC(=O)c1ccc(Nc2cccc(NC(=O)c3cccnc3)c2)cc1] | 445.5693 | C26H31N5O2 | N-{3-[4-(3-Diethylamino-propyl)carbamoyl)-phenylamino]-phenyl}-nicotinamide Formula V |

TABLE 1-continued
| Compound | Structure | MW | Structure | Compound |
|---|---|---|---|---|
| FMMB25.11 | 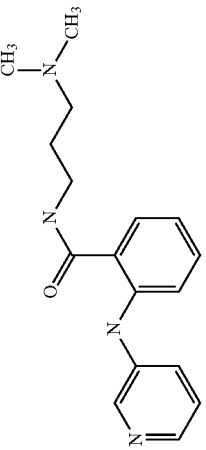 | 298.3911 | C17H22N4O | N-(3-Dimethylamino propyl)-2-(pyridin-3-ylamino)benzamide Formula V |
| FMMB25.14 | 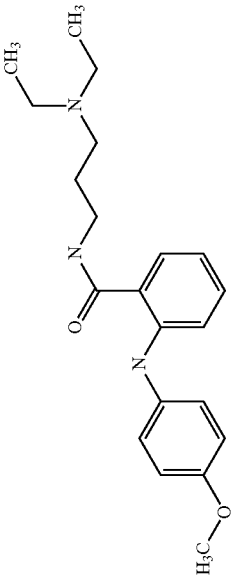 | 355.4842 | C21H29N3O2 | N-(3-Dimethylamino propyl)-2-(4-methoxy-phenylamino)-benzamide Formula V |

Synthesis of the compounds described in table I is described below.

Synthesis of Stilbene (Olefin) Compounds

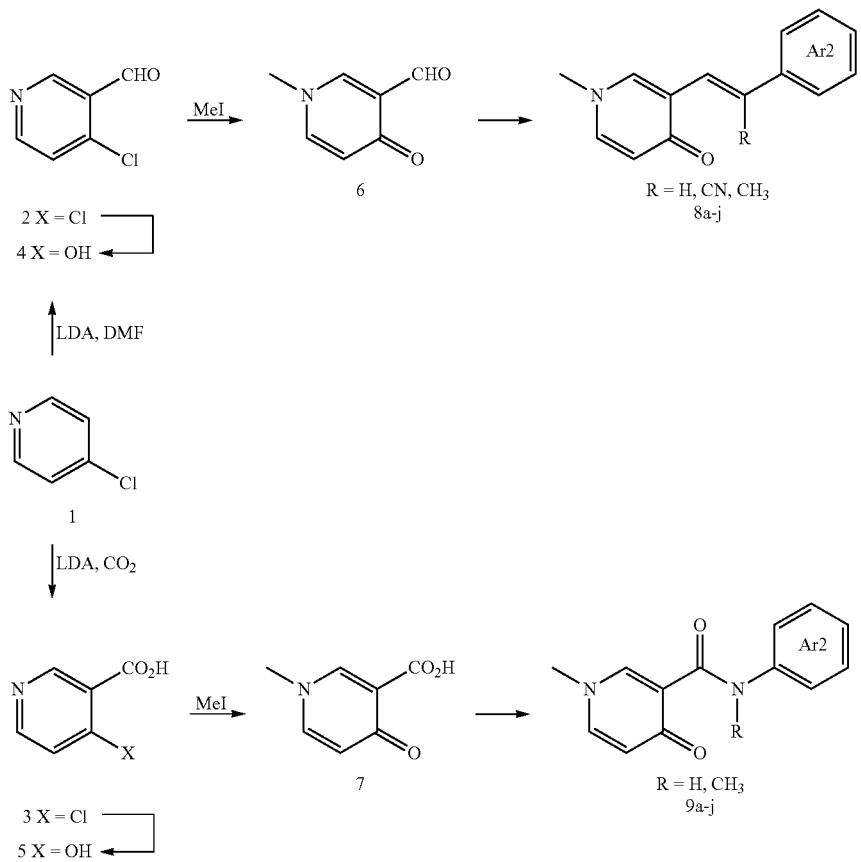

4-Chloropyridine 1 is obtained by neutralization of 4-chloropyridine hydrochloride with 10% NaOH as described in SCHMID & WOLKOFF (*Canadian Journal of Chemistry*, vol. 50, p. 1181-1187, 1972). 4-Chloropyridine 1 (15 mmol) is reacted in THF (250 ml) at −78° C. (nitrogen atmosphere) with 1.2 equivalents of lithium diisopropylamide (1.5 M solution in hexanes containing one equivalent of THF, ALDRICH) (THRASHER et al., *Heterocycles*, vol. 67, p. 543-547, 2006).

Reaction of the resulting anion with either an excess of anhydrous DMF or an excess of methyl formate allows the formation of 4-chloropyridine-3-carboxaldehyde 2, isolated in the form of a colorless solid (60-70%).

Following the procedure described in MARSAIS et al. (*J. Het. Chem.*, vol. 25, p. 81-87, 1988), compound 2 is heated for 6 h in an aqueous solution of 3 N HCl containing several drops of 3% $H_2O_2$, in order to obtain 4-hydroxypyridine-3-carboxaldehyde 4 as a colorless solid (>80%).

Following the procedure described in DI MARCO (*Eur. J. Inorg. Chem.*, p. 1284-1293, 2006), pyridine aldehyde 4 is reacted with an excess of methyl iodide for 2 h in DMF at 100° C. in order to obtain compound 6 isolated in the form of a colorless solid.

NMR and mass spectra data for compounds 2, 4 and 6 correspond to values found in the literature.

Finally, compound 6 serves as a skeleton for the synthesis of stilbene analogues of IDC16, notably compounds 8a-j.

This reaction involves placing compound 6, under the classic conditions of the WITTIG reaction (see for example GOPAL-SAMY et al., *J. Med. Chem.*, vol. 47, p. 1893-1899, 2004), in contact with the required phosphonium salts obtained either commercially or prepared by reacting the required bromide derivative with triphenylphosphine. For all of the compounds 8a-j, the presence of E double bond geometry is deduced from the values of the 400 MHz $^1$H NMR spectrum.

Synthesis of Amide Compounds

As above, 4-chloropyridine 1 is obtained by neutralization of 4-chloropyridine hydrochloride with 10% NaOH as described in SCHMID & WOLKOFF (Canadian Journal of Chemistry, vol. 50, p. 1181-1187, 1972). 4-Chloropyridine 1 (15 mmol) is reacted in THF (250 ml) at −78° C. (nitrogen atmosphere) with 1.2 equivalents of lithium diisopropylamide (1.5 M solution in hexanes containing one equivalent of THF, ALDRICH) (THRASHER et al., *Heterocycles*, vol. 67, p. 543-547, 2006).

Reaction of the resulting anion with dry $CO_2$ allows the formation of 4-chloropyridine-3-carboxylic acid 3 (4-chloronicotinic acid), isolated as a colorless solid with a yield of 60-80% (see GUILLIER et al., *J. Org. Chem.*, vol. 60, p. 292-296, 1995).

Compound 3 is heated in water (see ROSS, *J. Chem. Soc.* (C), p. 1816-1821, 1966) to obtain 4-hydroxypyridine-3-carboxylic acid 5 as a colorless solid (>80%).

Acid 5 is reacted in the presence of an excess of methyl iodide in DMF at 1000° C. for 2 h. Compound 7 is then isolated as a colorless solid.

NMR and mass spectra data for compounds 3, 5 and 7 correspond to values found in the literature.

Finally, compound 7 serves as a skeleton for the synthesis of amide analogues of IDC16, notably compounds 9a-j. This reaction involves placing compound 7 in contact with the required aromatic and heteroaromatic amines under classical conditions for forming peptide bonds. Typically, compound 7 in solution in DMF containing N-methylmorpholine is reacted with isobutyl chloroformate (0° C. or room temperature, 1 hour), and compounds 9a-j are then isolated as colorless solids with yields of 60-90%. These compounds are finally characterized by mass spectroscopy and $^1$H NMR (400 MHz).

Preparation of IDC16 Analogues 13a-j and 14a-j

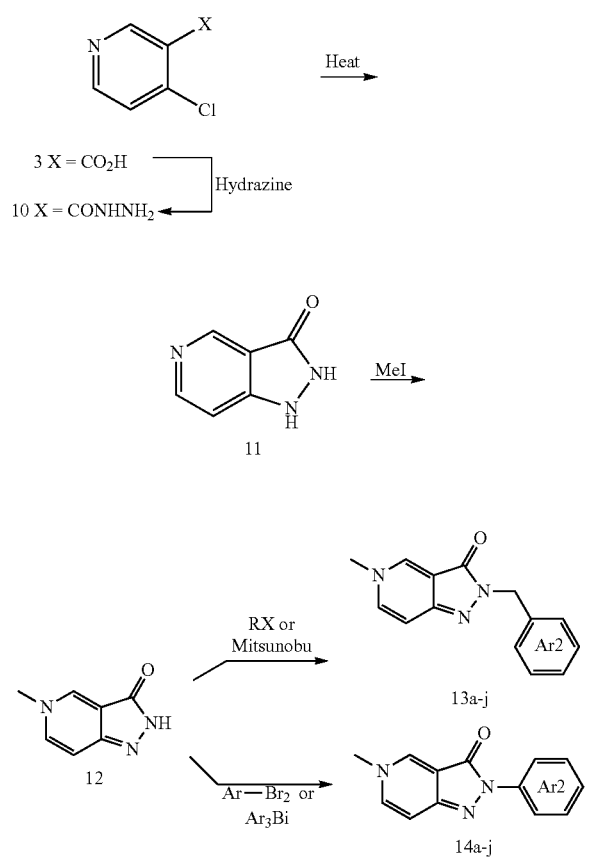

4-Chloropyridine-3-carboxylic acid 3 is reacted under classical peptide coupling conditions with isobutylchloroformate (1.3 equivalents) and N-methyl morpholine (1.3 equivalents) in DMF at room temperature and the active ester intermediate is then treated with a solution of anhydrous hydrazine (1 equivalent; 1.0 M solution in THF; ALDRICH) stirred constantly overnight (*Intl. J. Pepetide & Protein Res.*, vol. 11, p. 297, 1978). The mixture containing hydrazide 10 is then filtered to eliminate solids and heated at 100° C. for 2-4 hours to form a ring and to obtain compound 11.

Compound 11 is reacted in the presence of an excess of methyl iodide in DMF at 1000° C. for 2 h. Compound 12 is then isolated as a colorless solid.

Compound 12 is alkylated to obtain compounds 13a-j and 14a-j according to techniques well known to those skilled in the art (see in particular STARKOV, *Tet. Letters*, vol. 48, p. 1155-1157, 2007).

Preparation of IDC16 Analogues 19a-j and 20a-j

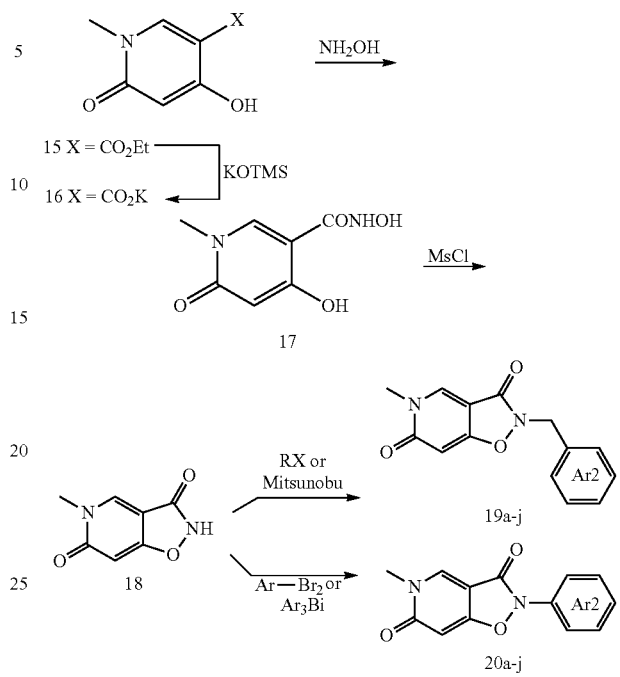

4-Hydroxy-1-methyl-6-oxo-1,6-dihydropyridine-3-carboxylate 15 is prepared according to the protocol described in WALLACE et al. (*J. Med. Chem.*, vol. 49, p. 441-444, 2006), then reacted with potassium trimethylsilanolate in THF for 4-5 hours at 20° C. (MOTORINA et al., *J. Am. Chem. Soc.*, vol. 23, p. 8-17, 2001), and the corresponding potassium salt 16 of the acid obtained after vacuum concentration is resuspended in DMF and reacted with isobutyl chloroformate and N-methyl morpholine (2 eq.) at room temperature, and then hydroxylamine in MeOH is added to the mixture (REDDY, *Tet. Letters*, vol. 41, p. 6285-6288, 2000). Hydroxamic acid intermediate derivative 17 is then resuspended in $CH_2Cl_2$ containing isopropylethylamine and treated with mesyl chloride (1 eq.) and stirred at room temperature for 24 h. The desired product with a closed ring 18 is produced by allowing the reaction to proceed, and then the solvent is eliminated by vacuum drying.

Compound 18 is alkylated to obtain compounds 19a-j and 20a-j again according to techniques well known to those skilled in the art (see notably STARKOV, *Tet. Letters*, vol. 48, p. 1155-1157, 2007).

Preparation of Azabenzimidazoles

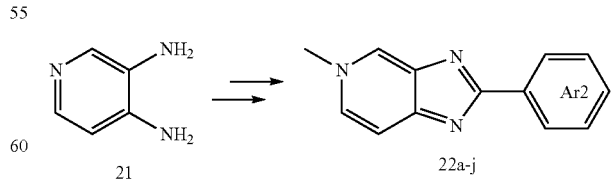

Numerous compounds of formula 22 are already well known (approximately 1,500 compounds identified in SciFinder). Said compounds can be simply obtained from 3,4-daminopyridine.

Example 3

Selective Inhibition of HIV-1 mRNA Splicing Ex Vivo by Compounds According to the Present Invention The efficiency of the compounds described in example 2 was tested using pΔPSP plasmid (JACQUENET et al., *J. Biol. Chem.*, vol. 276, p. 40464-40475, 2001), which contains the proviral HIV-1 genome with a deletion of nucleotides 1511 to 4550. This pΔPSP plasmid contains all HIV-1 splicing sites and the relative use of these various sites appears similar to that of the wild virus.

HeLa cells were cultivated in RPMI 1640 medium (GIBCO) supplemented with fetal calf serum on plates 3 cm in diameter (NUNC) to a confluence of 70-80%. These cells were then transfected with the pΔPSP plasmid as described in JACQUENET et al. (2001).

The HeLa cells transfected with pΔPSP were then treated with various concentrations (1.5 µM or 3 µM) of the compounds described in example 2 or of IDC16 as a positive control. As a negative control, cells transfected with pΔPSP, but without subsequent treatment, were included (Clt).

Total cellular RNA was then extracted with the RNeasy kit (QIAGEN) while following the manufacturer's instructions. 4 µg of total RNA then underwent reverse transcription using the OMNISCRIPT REVERSE TRANSCRIPTASE kit (QIAGEN) while following the manufacturer's instructions. The mixture obtained was then aliquotted in 96-well plates and subjected to amplification using BSS sense primers (5'-GGCTTGCTGAAGCGCGCACGGCAAGAGG-3'; SEQ ID NO: 1), SJ4.7A anti-sense primers (5'-TTGGGAG-GTGGGTTGCTTTGATAGAG-3'; SEQ ID NO: 2) and primers to amplify GAPDH as an internal control. BSS and SJ4.7A primers make it possible to amplify several isoforms resulting from various splices coding for viral proteins Nef, Rev, and Tat (JACQUENET et al., cited above, 2001). The PCR products were then analyzed by polyacrylamide gel electrophoresis after standardization with GAPDH (SORET et al., *Proc. Natl. Acad. Sci. U.S.A.*, vol. 102, p. 8764-8769, 2005).

FIG. 1 shows the detail of a polyacrylamide gel obtained presenting the various isoforms obtained (Nef2, Rev1, Rev2, Nef3, Nef4, Nef5, Tat1 and Tat2) for the untreated cells (Clt) or treated with the compounds IDC16, C48, C49, C55 or C56.

The results show a dose-dependent reduction in the level of HIV-1 splicing products for the cells treated with compounds C48, C49, C55 and C56, a reduction comparable to that obtained in the presence of compound IDC16.

Consequently, the results thus show that compounds C48, C49, C55 and C56 inhibit HIV-1 splicing with an efficiency comparable to compound IDC16.

Example 4

Inhibition of HIV-1 Production in Infected Peripheral Blood Mononuclear Cells (PBMCs)

The first determination is that of the concentration of compound that exhibits the fewest side effects in terms of cell viability and progression of the cell cycle.

Within this framework, the peripheral blood mononuclear cells (PBMCs) of healthy donors are isolated by centrifugation on a FICOLL gradient. The cells are then cultivated to a density of $2.5 \times 10^6$ cells/ml with RPMI medium supplemented with 1% inactivated human AB serum, then incubated at 37° C., 5% $CO_2$ for an additional hour. The peripheral blood mononuclear cells are then recovered and cultivated for two days in RPMI medium supplemented with 10% fetal calf serum.

Part of the peripheral blood mononuclear cells (PBMC) is then cultivated for 72 hours in the presence of tritiated thymidine and phytohemagglutinin A (PHA) and in the presence or absence of the compounds described in example 2. Cell proliferation in the presence of the compounds of example 2 is finally measured by determining the incorporation of tritiated thymidine in the cellular DNA of the treated cells.

Another part of the peripheral blood mononuclear cells (PBMCs) that is activated (stimulated for 2 days with PHA and IL-2) is infected with HIV strains NL4.3 or Ada-M R5. The cells are then cultivated for 14 days in the presence of the compounds described in example 2. Viral replication is finally determined by quantifying protein p24 by the ELISA method. In parallel, cell viability is measured by exclusion with trypan blue in comparison with that of the untreated cells.

Example 5

Inhibition of HIV-1 Production in Infected Macrophages

In order to generalize the HIV-1 replication effect of the molecules described in example 2 to other cell types, we examined various steps of the viral cycle in cells treated with the various drug at a concentration of 5M and submitted to one-round infection.

For such experiences, macrophages can be infected by the Ada-M R5HIV strain and treated for 18 hours with various concentrations of the compounds described in example 2. The culture medium is then eliminated and the cells washed with an abundance of PBS. The cells are then cultivated under normal conditions. The culture medium and the cells are then collected at days 4, 7 and 14. Finally, virus replication is measured indirectly by determining the level of p24 antigen in both the culture supernatant and the cellular lysate by the ELISA method. In parallel, cell viability of the macrophages in the presence of the compounds of example 2 is measured as before.

For this purpose, we exposed HOS-CD4$^+$-CCR5$^+$ cells to defective virions obtained by cotransfecting 293T cells with a plasmid encoding the R5 envelope of the AD8 strain and another plasmid containing the entire HIV-1 genome mutated in the envelope gene and harbouring a luciferase marker gene fused to nef (Connor R I, Chen B K, Choe S, Landau N R. (1995) Vpr is required for efficient replication of human immunodeficiency virus type-1 in mononuclear phagocytes. Virology 206: 935-944). The amounts of luciferase activity in cells infected with these virions reflect both the number of integrated proviruses and expression of multiply spliced species encoding nef/luc. Two days post-infection, luciferase activity in HOS-CD4+-CCR5+ infected cells was measured. Of note, the inhibitory effect could be smaller in this one-round infection assay than in other assays where several rounds of infection were carried out. Among the compounds of the example 2 tested, 12 show a luciferase inhibitory effect ranging between 30% up to 52%, which compound are listed in table II.

TABLE II

| Compound (5 μm) | Structure | Compound | % of luciferase inhibition |
|---|---|---|---|
| FMMB17.6 | 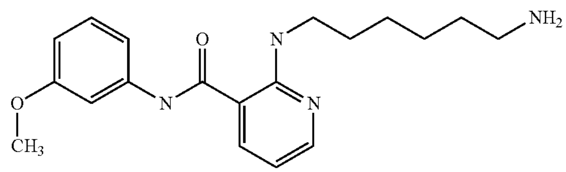 [SMILES: COc1cccc(NC(=O)c2cccnc2NCCCCCCN)c1] | 2-(6-Amino-hexylamino)-N-(3-methoxy-phenyl)-nicotinamide | 45 |
| FMMB17.7 | 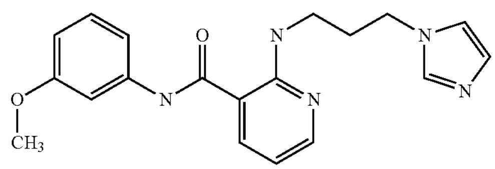 [SMILES: COc1cccc(NC(=O)c2cccnc2NCCCn2ccnc2)c1] | 2-(3-Imidazol-1-yl-propylamino)-N-(3-methoxy-phenyl)-nicotinamide | 41 |
| MMB31.12 | 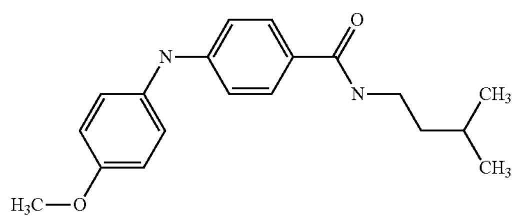 [SMILES: COc1ccc(Nc2ccc(C(=O)NCCC(C)C)cc2)cc1] | 4-(4-Methoxy-phenylamino)-N-(3-methyl-butyl)-benzamide | 44 |
| FMMB32.15 | 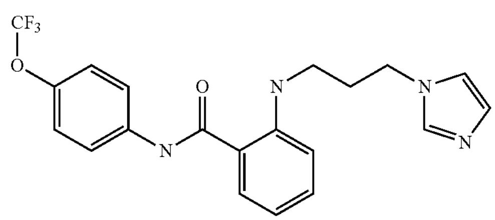 [SMILES: O=C(Nc1ccc(OC(F)(F)F)cc1)c1ccccc1NCCCn1ccnc1] | 2-(3-Imidazol-1-yl-propylamino)-N-(4-trifluoromethoxy-phenyl)-benzamide | 41 |
| FMMB41.2 | 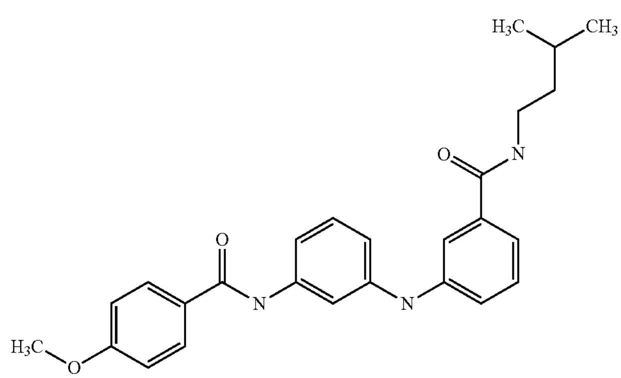 [SMILES: COc1ccc(C(=O)Nc2cccc(Nc3cccc(C(=O)NCCC(C)C)c3)c2)cc1] | N-(3-Methyl-butyl)-3-[3-(4-methoxy-benzoylamino)-phenylamino]-benzamide | 35 |
| FMMB41.4 | 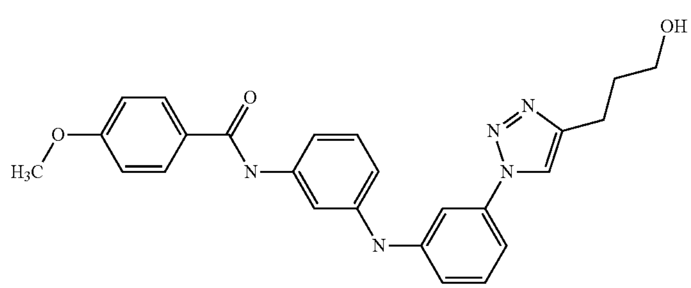 [SMILES: COc1ccc(C(=O)Nc2cccc(Nc3cccc(-n4cc(CCCO)nn4)c3)c2)cc1] | N-(3-{4-[4-(3-Hydroxy-propyl)-[1,2,3]triazol-1-yl]-phenylamino}-phenyl)-4-methoxy-benzamide | 31 |

TABLE II-continued

| Compound (5 µm) | Structure | Compound | % of luciferase inhibition |
|---|---|---|---|
| FMMB44.1 | 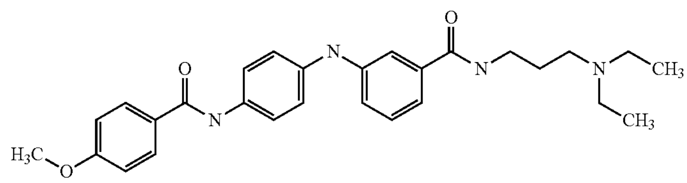 [SMILES: CCN(CC)CCCNC(=O)c1cccc(Nc2ccc(NC(=O)c3ccc(OC)cc3)cc2)c1] | N-(3-Diethylamino-propyl)-3-[4-(4-methoxy-benzoylamino)-phenylamino]-3-methyl-benzamide | 57 |
| FMMB44.2 | 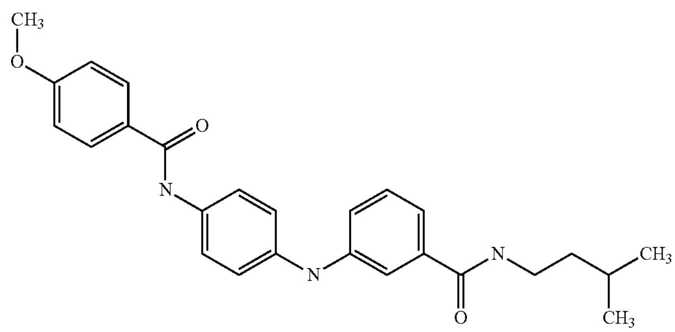 [SMILES: COc1ccc(C(=O)Nc2ccc(Nc3cccc(C(=O)NCCC(C)C)c3)cc2)cc1] | N-(3-Methyl-butyl)-3-[4-(4-methoxy-benzoylamino)-phenylamino]-benzamide | 32 |
| FMMB44.4 | 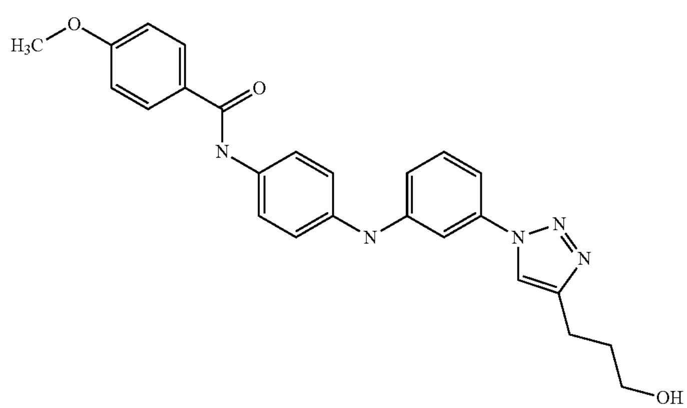 [SMILES: COc1ccc(C(=O)Nc2ccc(Nc3cccc(-n4cc(CCCO)nn4)c3)cc2)cc1] | 3-(1-{4-[(4-methoxybenzamido)-phenylamino]-phenyl}-1H-1,2,3-triazol-4-yl)-propan-1-ol | 33 |
| FMMB44.6 | 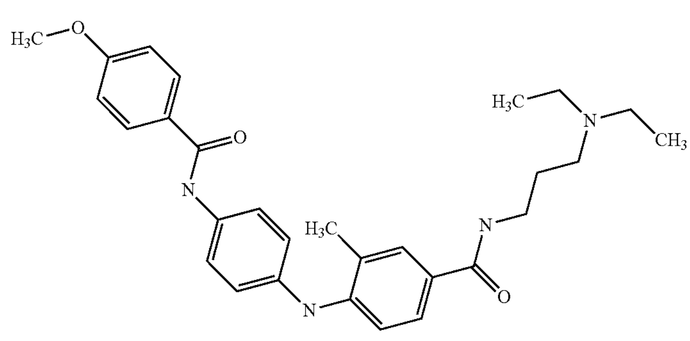 [SMILES: CCN(CC)CCCNC(=O)c1ccc(Nc2ccc(NC(=O)c3ccc(OC)cc3)cc2)c(C)c1] | N-(3-Diethylamino-propyl)-4-[4-(4-methoxy-benzoylamino)-phenylamino]-3-methyl-benzamide | 46 |
| FMMB44.8 | 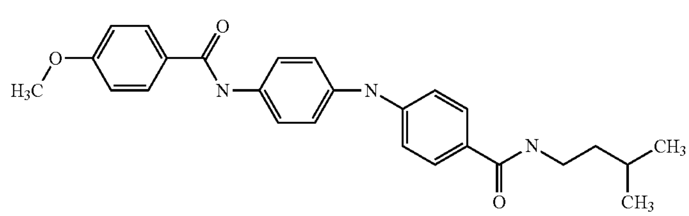 [SMILES: COc1ccc(C(=O)Nc2ccc(Nc3ccc(C(=O)NCCC(C)C)cc3)cc2)cc1] | N-(3-Methyl-butyl)-4-[4-(4-methoxy-benzoylamino)-phenylamino]-benzamide | 52 |

TABLE II-continued

| Compound (5 μm) | Structure | Compound | % of luciferase inhibition |
|---|---|---|---|
| FMMB53.8 | 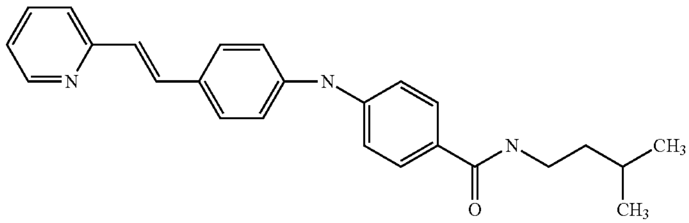 [SMILES: CC(C)CCNC(=O)c1ccc(Nc2ccc(/C=C/c3ccccn3)cc2)cc1] | N-(3-Methyl-butyl)-4-[4-((E)-2-pyridin-2-yl-vinyl)-phenylamino]-benzamide | 33 |
| Control (AZT 50 μm) | — | 3'-azido-3'-deoxythymidine, zidovudine | 39.5 |

Only compounds that demonstrated less than 10% toxicity are shown.

The results established that compared to Azidothymidine (AZT, 3'-azido-3'-deoxythymidine, zidovudine) which is the first nucleoside reverse transcriptase inhibitor (NRTI) approved for HIV-1 therapy, our compounds are 10 times more efficient than AZT. In fact, a concentration of 50 μM of AZT is required to achieve 32% inhibition of luciferase under the same conditions.

Example 6

Absence of Inhibition of Splicing of Cellular Genes

In order to identify the effect of the compounds of example 2 on the splicing of endogenous genes, 96 isoforms obtained after alternative splicing and covering a variety of apoptotic genes were selected.

Peripheral blood mononuclear cells are treated or not treated with the compounds of example 2 and IDC16 as a positive control as described in example 3. Preparation of total RNA for each culture condition followed by preparation of cDNA for each RNA sample is then carried out as described in example 3.

The mixture obtained is then aliquotted in 96-well plates and subjected to amplification using for each well a pair of sense and anti-sense primers specific to each isoform.

The level of expression of each isoform for the cells treated with the compounds of example 2 is then compared with that obtained for the cells treated with IDC16 and for the untreated cells.

Example 7

Identification of Effective Compounds to Treat Metastatic Breast Cancers

By alternative splicing the RON proto-oncogene generates two protein isoforms with distinct properties: 1) RON is a tyrosine kinase receptor involved in tissue dissociation, cell mobility and invasion of the extracellular matrix, 2) the truncated isoform of the RON receptor is constitutively active due to the elimination of exon 11 sequences. This truncated isoform is expressed strongly in breast cancer cells with high metastatic capacity and its expression is sufficient to activate epithelial-mesenchymal transition.

To test the effectiveness of the compounds described above in treating metastatic breast cancer, cells preferentially expressing the truncated RON isoform were treated with various concentrations of the compounds described in example 2. The effectiveness of said compounds is then measured by determining the level of expression of the truncated RON isoform in the treated or untreated cells, with effective compounds corresponding to those that lower the level of expression of said isoform.

Other protocols are available for testing the effectiveness of the compounds described above in treating metastatic cancer. One of these protocols corresponds to the wound Healing assay protocol testing cell migration.

To mimics cell migration during wound healing in vivo, we have used the wound-healing assay to study directional cell migration in vitro (Rodriquer et al., Methods Mol Biol, 2005). A cell monolayer of seed Breast cancer cells (MDA-MB231 Luc D3H2LN) is treated with 5 μM of indicated molecules for 48 h before a "wound" is created, images were then captured at the beginning and at regular intervals during cell migration to close the wound. Images were compared to control untreated cells or to compounds that have no effect on cell migration. Wounds can heal in as little as 12-24 hours for highly metastatic cells, or may take up to 72 hours for less metastatic cells. Images of the same field at 0, 2, 4, 6, 8, 10, 12, 18 and 24 hours until the closure of the entire wound using phase-contrast light microscopy (10× magnifications).

Figure 2:
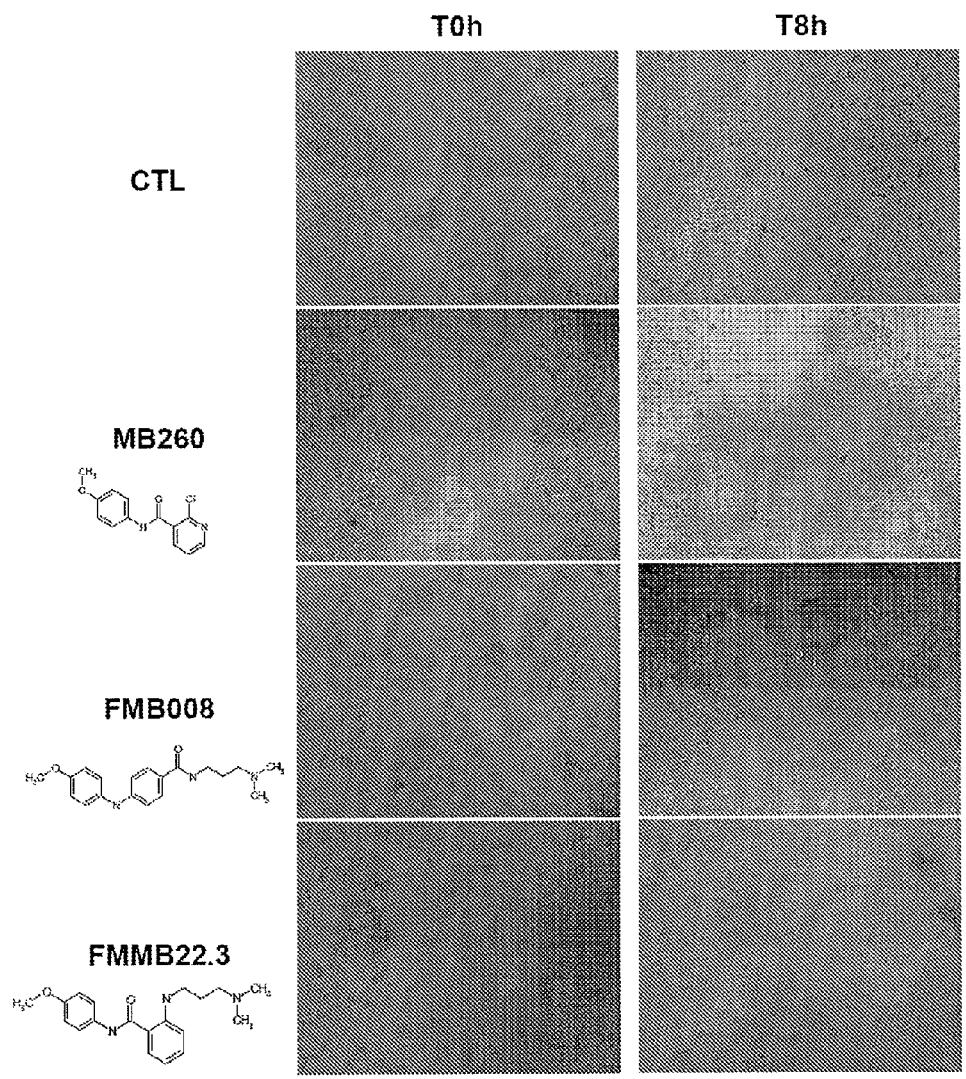
FIG. 2 shows that the compounds MB260, FMB008 and FMMB22.3 strongly inhibit cell migration compared to negative control (CTL).

The FIG. 2 shows that the compounds MB260, FMB008 and FMMB22.3 strongly inhibit cell migration compared to negative control (CTL).

Example 8

Identification of Effective Compounds for Treating Duchenne Muscular Dystrophy

As target for gene therapy, Duchenne muscular dystrophy (DMD) presents many obstacles but also unparalleled prospect for correction by alternative splicing. Duchenne muscular dystrophy results from mutations in the dystrophin gene, leading to the absence of its expression or to the expression of truncated proteins. More specifically, the majority of mutations in the dystrophin gene occur in the region encoding the spectrin-like central rod domain (see dia 1), which is largely dispensable. Exon 51 is one of the most mutated exon of encoding the spectrin-like central rod domain in DMD patients. The skipping of exon 51 can generate a shortened but in-frame transcript, permitting translation of a partially functional dystrophin protein.

To test the inventive compounds, an animal model of Duchenne muscular dystrophy can be used, namely the mdx mouse. More specifically, mdx mice carry a stop codon mutation in exon 23 of the dystrophin gene which is responsible for completely extinguishing dystrophin expression. Thus, mdx mice can be treated with various concentrations of the compounds described in example 2 and then myoblast samples are taken from these mice to test these compounds for their capacity to induce exon 23 skipping in these cells.

Presently, we have tested this idea using stable cell lines expressing a luciferase reporter in which exon 51 and flanking introns were inserted in the middle of the luciferase cDNA. Because exon 51 was constitutively included between luciferase halves no luciferase activity was detected in these stable cell lines. In contrast in the presence of AAV vectors harbouring U7 antisens designed to promote skipping of exon 51, luciferase activity was restored. We have used this system to screen molecules able to potentiate the efficacy of AAV vectors. The compounds of example 2 have been tested (5 µm) in this system and the results for the most efficient molecules are disclosed in Table III.

TABLE III

| Compound (5 µm) | Structure | Compound | % of Activity luciferase* |
|---|---|---|---|
| FMMB21.1 | 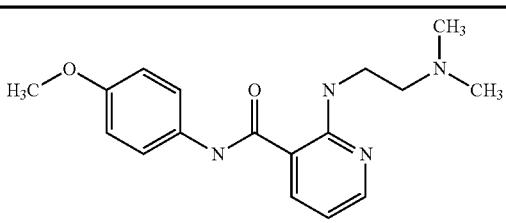 | 2-(2-Dimethylamino-ethylamino)-N-(4-methoxy-phenyl)-nicotinamide | 220 |
| FMMB22.1 | 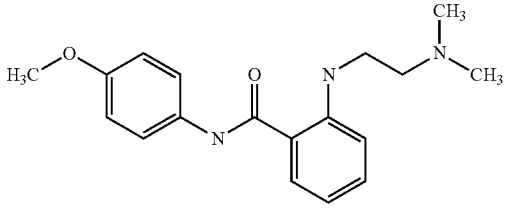 | 2-(2-Dimethylamino-ethylamino)-N-(4-methoxy-phenyl)-benzamide | 220 |
| FMB080 | 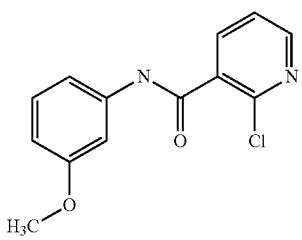 | 2-Chloro-N-(3-methoxy-phenyl)-nicotinamide | 150 |
| MB228 | 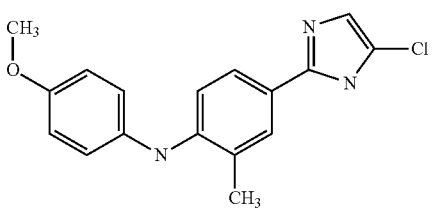 [SMILES: COc1ccc(Nc2ccc(-c3ncc(Cl)[nH]3)cc2C)cc1] | 4-(5-Chloro-1H-imidazol-2-yl)-2-methyl-phenyl]-(4-methoxy-phenyl)-amine | 180 |
| MB260 | 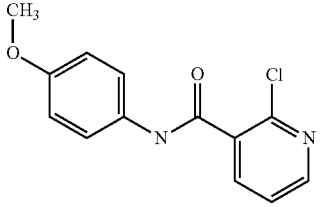 [SMILES: COc1ccc(NC(=O)c2cccnc2Cl)cc1] | 2-Chloro-N-(4-methoxy-phenyl)-nicotinamide | 200 |
| MB261 | 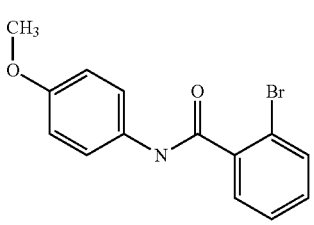 [SMILES: COc1ccc(NC(=O)c2ccccc2Br)cc1] | 2-Bromo-N-(4-methoxy-phenyl)-benzamide | 220 |

TABLE III-continued

| Compound (5 μm) | Structure | Compound | % of Activity luciferase* |
|---|---|---|---|
| MB262 | H₃C-O-C₆H₄-NH-C(O)-C₆H₄-Br (2-bromo) | 2-Bromo-N-(3-methoxy-phenyl)-benzamide | 180 |

*luciferase activity reflect exon skipping induced by 5000 MOI of AAV vector harbouring an anti-sens sequence of exon 51 of Dystrophin gene Among the compounds of example 2 tested 7 showed a two fold increase of luciferase activity compared to AAV vector alone. These molecules are, therefore, potent therapeutic agent for DMD treatment.

Example 9

Identification of Effective Compounds for Treating Early-Aging Syndrome (Progeria)

Progeria is a rare (prevalence of approximately one in four to eight million births) and very severe developmental disorder characterized by the early appearance of certain pathologies usually developed during physiological aging, such as atherosclerosis, insulin resistant type II diabetes, cataracts, osteoporosis and aging of the skin. Analysis of this pathology has shown that it results from abnormal expression of the LMNA gene associated with its abnormal splicing. Astonishingly, this same aberrant splicing of the LMNA gene has been found in healthy elderly subjects not carrying the mutation.

It could be shown that certain compounds acting on splicing are able to increase the use of the normal LMNA gene splicing site while that of the aberrant splicing site decreases. To test the effectiveness of the compounds described in example 2 in treating progeria, cells carrying a mutation of the LMNA gene causing its abnormal splicing were treated or not treated with various concentrations of said compounds. The effectiveness of said compounds is then measured by determining the level of expression of the abnormal isoform in the treated or untreated cells, with the effective compounds corresponding to those that lower the level of expression of said isoform.

What is claimed is:

1. A compound selected from the group consisting of:
   N-(3-Dimethylamino-propyl)-3-(4-trifluoromethoxy-phenylamino)-benzamide;
   4-(4-Methoxy-phenylamino)-3-methyl-N-(3-methyl-butyl)-benzamide;
   3-Methyl-N-(3-methyl-butyl)-4-(4-trifluoromethoxy-phenylamino)-benzamide;

N-(2-Dimethylamino-ethyl)-2-(4-trifluoromethoxy-phenylamino)-benzamide;
N-(2-Diethylamino-ethyl)-2-(4-trifluoromethoxyphenylamino)-benzamide;
N-(2-Diethylamino-propyl)-2-(4-trifluoromethoxy-phenylamino)-benzamide;
(N-Diethylamino)-{1-[4-(4-Methoxy-phenylamino)-phenyl]-1H-1,2,3-triazol-4-yl}-methylamine;
(N-Diethylamino)-{1-[4-(4-trifluoromethoxyphenylamino)-phenyl]-1H-1,2,3-triazol-4-yl}-methylamine;
(N-Diethylamino)-{1-[4-(4-N-dimethylamino-phenylamino)-phenyl]-1H-1,2,3-triazol-4-yl}-methylamine;
N-(3-Imidazol-1-yl-propyl)-2-(4-methoxy-phenylamino)-benzamide;
N-(3-Imidazol-1-yl-propyl)-2-(4-trifluoromethoxy-phenylamino)-benzamide;
2-(4-Dimethylamino-phenylamino)-N-(3-imidazol-1-yl-propyl)-benzamide;
N-(4-Diethylamino-1-methyl-butyl)-2-(4-dimethylaminophenylamino)-benzamide;
N-(2-Dimethylamino-ethyl)-4-(4-trifluoromethoxy-phenylamino)-benzamide;
N-(2-Dimethylamino-ethyl)-4-(4-dimethylamino-phenylamino)-benzamide;
N-(2-Dimethylamino-ethyl)-4-(4-methoxy-phenylamino)-3-methyl-benzamide;
N-(3-Diethylamino-propyl)-4-(4-methoxy-phenylamino)-3-methyl-benzamide;
N-(3-Diethylamino-propyl)-3-methyl-4-(4-trifluoromethoxy-phenylamino)-benzamide;
N-(3-Diethylamino-propyl)-4-(4-dimethylamino-phenylamino)-3-methyl-benzamide;
N-(2-Dimethylamino-ethyl)-3-methyl-4-(4-trifluoromethoxy-phenylamino)-benzamide;
3-{1-[4-(4-Methoxy-phenylamino)-phenyl]-1H-1,2,3-triazol-4-yl}-propan-1-ol;
(N-diethylamino)-{1-[3-(4-Methoxy-phenylamino)-phenyl]-1H-1,2,3-triazol-4-yl}-methylamine;
[4-(5-Chloro-1H-imidazol-2-yl)-2-methyl-phenyl]-(4-methoxy-phenyl)-amine;
N-(2-Diethylamino-ethyl)-4-(4-methoxy-phenylamino)-benzamide;
N-(2-Dimethylamino-ethyl)-2-(4-methoxy-phenylamino)-benzamide;
4-(4-Methoxy-phenylamino)-N-(3-methyl-butyl)-benzamide;
N-(3-Imidazol-1-yl-propyl)-4-(4-trifluoromethoxy-phenylamino)-benzamide;
[3-(4-Diethylaminomethyl-[1,2,3]triazol-1-yl)-phenyl]-(4-dimethylamino)-phenylamine;
N-(2-Diethylamino-ethyl)-2-(4-methoxy-phenylamino)-benzamide;
3-{1-[3-(4-Trifluoromethoxy-phenylamino)-phenyl]-1H-[1,2,3]triazol-4-yl}-propan-1-ol;
3-{1-[3-(4-Dimethylamino-phenylamino)-phenyl]-1H-[1,2,3]triazol-4-yl}-propan-1-ol;
N-(3-Diethylamino-propyl)-2-(4-methoxy-phenylamino)-benzamide; and
pharmaceutically acceptable salts thereof.

2. A pharmaceutical composition, comprising at least one compound of claim 1 and a pharmaceutically acceptable support.

* * * * *

```
SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct-amorce PCR

<400> SEQUENCE: 1
ggcttgctga agcgcgcacg gcaagagg                                28

<210> SEQ ID NO 2
<211> LENGTH: 26
<212> TYPE: DNA
<213> ORGANISM: Artificial Sequence
<220> FEATURE:
<223> OTHER INFORMATION: Synthetic Construct-amorce PCR

<400> SEQUENCE: 2
ttgggaggtg ggttgctttg atagag                                  26
```